United States Patent
Choo et al.

(10) Patent No.: US 9,334,324 B2
(45) Date of Patent: May 10, 2016

(54) PODOCALYXIN-LIKE-PROTEIN-1 BINDING ANTIBODY MOLECULE

(75) Inventors: Boon Hwa Andre Choo, Singapore (SG); Vai Tak Victor Wong, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 50 days.

(21) Appl. No.: 13/577,104

(22) PCT Filed: Feb. 1, 2011

(86) PCT No.: PCT/SG2011/000047
§ 371 (c)(1),
(2), (4) Date: Aug. 3, 2012

(87) PCT Pub. No.: WO2011/096894
PCT Pub. Date: Aug. 11, 2011

(65) Prior Publication Data
US 2012/0301899 A1    Nov. 29, 2012

Related U.S. Application Data

(60) Provisional application No. 61/301,262, filed on Feb. 4, 2010.

(51) Int. Cl.
*C07K 16/00* (2006.01)
*C07K 16/28* (2006.01)

(52) U.S. Cl.
CPC ............. *C07K 16/28* (2013.01); *C07K 2317/53* (2013.01); *C07K 2317/54* (2013.01); *C07K 2317/55* (2013.01); *C07K 2317/622* (2013.01); *C07K 2317/626* (2013.01); *C07K 2317/73* (2013.01); *C07K 2319/73* (2013.01)

(58) Field of Classification Search
None
See application file for complete search history.

(56) References Cited

FOREIGN PATENT DOCUMENTS

| WO | 2007/102787 A1 | 9/2007 |
| WO | 2010/033084 A1 | 3/2010 |

OTHER PUBLICATIONS

Paul, Fundamental Immunology, (textbook), 1999, under the heading Immunoglobulins: Structure and Function, , pp. 37, 43, 58, 59.*
Rudikoff et al ., Proc Natl Acad Sci USA 1982 vol. 79 p. 1979.*
Knappik et al ( Journal of Molecular Biology, 2000.*
Ellis et al ( Ellis et al., J of Immunology, 1995, V.155, pp. 925-937.*
Casset et al. (2003) BBRC 307, 198-205.*
Choo et al., "Selection Against Undifferentiated Human Embryonic Stem Cells by a Cytotoxic Antibody Recognizing Podocalyxin-Like Protein-1", Stem Cells, 2008:26:1454-1463.
Kuhara et al., "Magnetic Separation of Human Podocalyxin-like Protein 1 (hPCLP1)-Positive Cells from Peripheral Blood and Umbilical Cord Blood Using Anti-hPCLP1 Monoclonal Antibody and Protein A Expressed on Bacterial Magnetic Particles", Cell Structure and Function, 34:23-30 (2009).
Lim et al., "Cytotoxic antibody fragments for eliminating undifferentiated human embryonic stem cells", Journal of Biotechnology, Mar. 30, 2011.
Ng et al., "Engineering of antibody fragments from mAb84, a cytotoxic antibody targeting undifferentiated human embryonic stem cells", RAFT VIII, Poster 15, Nov. 8-11, 2009.
Pluckthun et al., "New protein engineering approaches to multivalent and bispecific antibody fragments", Immunotechnology, 3 (1997) 83-105.
Tan et al., "Cytotoxic Antibody that Kills Undifferentiated Human Embryonic Stem Cells via Oncosis", Stem Cells, 2009;27:1792-1801.
International Search Report for PCT/SG2011/000047 dated Aug. 1, 2011.
Written Opinion for PCT/SG2011/000047 dated Aug. 1, 2011.

* cited by examiner

*Primary Examiner* — Michail Belyavskyi
(74) *Attorney, Agent, or Firm* — Choate, Hall & Stewart LLP; Charles E. Lyon; Michael L. Vetter

(57) ABSTRACT

The disclosure relates to novel markers of pluripotent stem cells and uses thereof, and particularly, though not exclusively, to antibody molecules based on fragments of mAb84 which bind to undifferentiated pluripotent stem cells via podocalyxin-like protein-1 (PODXL).

18 Claims, 23 Drawing Sheets

Cell Size

| Primer Name | Primer Sequence |
|---|---|
| c547t-F | 5' tctaaatacattcaaatatgtatccgcttatgaattaattcttagaaaaactcatcg 3' |
| c547t-R | 5' cgatgagttttctaagaattaattcataagcggatacatatttgaatgtatttaga 3' |
| c1422t-F | 5' ctgtttatgtaagcagacagttttattgtttatgaccaaaatcccctt 3' |
| c1422t-R | 5' aagggatttggtcataaacaataaaactgtctgcttacataaacag 3' |
| c4845t-F | 5' gccgaaacaagcgcttatgagcccgaagtgg 3' |
| c4845t-R | 5' ccacttcgggctcataagcgcttgtttcggc 3' |
| scFv84-NcoI_VH_F 1 | 5' gcccagccggccatggcccaggttcagctgcagcagag 3' |
| scFv84-VH_linker_R 2 | 5' cgatccgccaccgccagagccacctccgcctgaaccgcctccacc gctgctaacggtcacggtggtgcc 3' |
| scFv84-linker_VL_F 3 | 5' ggtggaggcggttcaggcggaggtggctctggcggtggcggatcg gatattgaactgacccagagccc 3' |
| scFv84-VL_NotI_R 4 | 5' gtgatgtgcggccgcacgtttgatttccagtttgg 3' |
| F(ab')2-84-VH_AgeI_F | 5' ccggaaccggtgaccgtgag 3' |
| F(ab')2-84-VH_30nt_AvrII_R | 5' tagcagcctaggttattaatgatgatgatgatgatgcgccgccgccgggcacggcgggcaggtatgggttttatc acagcttttcggttccactttttatc 3' |
| F(ab)2-(CPP)3_F | 5' gccgtgcccgccgtgcgcggcggcgc 3' |
| F(ab)2-(CPP)3_R | 5' gcgccgccgcgcacggcgggcacggc 3' |
| scFv-5_F | 5' cgtgaccgttagcagcggtggaggcggttcagatattgaactgacccagagcccggc 3' |
| scFv-5_R | 5' gccgggctctgggtcagttcaatatctgaaccgcctccaccgctgctaacggtcacg 3' |
| scFv-10_F | 5' ggtggaggcggttcaggcggaggtggctctgatattgaactgacccagagcccggc 3' |
| scFv-10_R | 5' gccgggctctgggtcagttcaatatcagagccacctccgcctgaaccgcctccacc 3' |
| scFv-0_VH_F | 5' gccggccatggcccaggttcagctgcagcagagc 3' |
| scFv-0_VHVL_R | 5' ggtcagttcaatatcgctgctaacggtcacg 3' |
| scFv-0_VL_R (same primer as scFv84-VL_NotI_R 4) | 5' gtgatgtgcggccgcacgtttgatttccagtttgg 3' |

Figure 9 scFv84

*Amino acid* qvqlqqsggglvqpggsmklscvasgftfsnywmnwvrqspekglewvaeirlksnnyathyaesvkgrftisrddskss
vylqmnnlraedtgiyyctgerawgqgttvtvssggggsggggsggggsdieltqspaimsaspgekvtmtcsasssvn
ymywyqqkpgssprlliydtsnlasgvpvrfsgsgsgtsysltisrmeaedaatyycqqwssypytfgggtkleikr
(SEQ ID NO: 1)

*Nucleotide*

Caggttcagctgcagcagagcggtggcggcctggtgcagccgggcggtagcatgaaactgagctgcgtggcgagcggt
tttacctttagcaactattggatgaattgggtgcgccagagcccggaaaaaggcctggaatgggtggcggaaattcgtctga
aaagcaataactatgcgacccattatgccgaaagcgtgaaaggtcgctttaccattagccgcgatgatagcaaaagcagc
gtgtatctgcagatgaacaatctgcgcgcggaagataccggcatttattattgcaccggcgaacgcgcgtggggccaggg
caccaccgtgaccgttagcagcggtggaggcggttcaggcggaggtggctctggcggtggcggatcggatattgaactg
acccagagcccggccattatgagcgcgagcccgggcgaaaaagtgaccatgacctgcagcgcgagcagcagcgtga
actatatgtattggtatcagcagaaaccgggcagcagcccgcgcctgctgatttatgataccagcaacctggccagcggtg
tgccggtgcgctttagcggtagcggcagcggcaccagctatagcctgaccattagccgtatggaagcggaagatgcggc
gacctattattgccagcagtggagcagctatccgtatacctttggcggtggcaccaaactggaaatcaaacgt
(SEQ ID NO: 13)

Figure 10 scFv84 Amino acid sequences

VH
qvqlqqsggglvqpggsmklscvasgftfsnywmnwvrqspekglewvaeirlksnnyathyaesvkgrftisrddskss
vylqmnnlraedtgiyyctgerawgqgttvtvss
(SEQ ID NO: 9)

Glysine-serine linker
ggggsggggsggggs
(SEQ ID NO: 12)

VL
dieltqspaimsaspgekvtmtcsasssvnymywyqqkpgssprliiydtsnlasgvpvrfsgsgsgtsysltisrmeaed
aatyycqqwssypytfgggtkleikr[aaa]
(SEQ ID NO: 8)

[optional sequence encoded by optional NotI site for cloning]

Murine IgG3 hinge
pkpstppgss
(SEQ ID NO: 10)

HTH with His-tag
geleellkhlkellkgprkgeleellkhlkellkggsggaphhhhhh
(SEQ ID NO: 11)

Figure 11 scFv84 Nucleotide sequences

VH
caggttcagctgcagcagagcggtggcggcctggtgcagccgggcggtagcatgaaactgagctgcgtggcgagcggtt
ttaccttagcaactattggatgaattgggtgcgccagagcccggaaaaaggcctggaatgggtggcggaaattcgtctga
aaagcaataactatgcgacccattatgccgaaagcgtgaaaggtcgctttaccattagccgcgatgatagcaaaagcagc
gtgtatctgcagatgaacaatctgcgcgcggaagataccggcatttattattgcaccggcgaacgcgcgtggggccaggg
caccaccgtgaccgttagcagc
(SEQ ID NO: 15)

Glysine-serine linker
ggtggaggcggttcaggcggaggtggctctggcggtggcggatcg
(SEQ ID NO: 18)

VL
gatattgaactgacccagagcccggccattatgagcgcgagcccgggcgaaaaagtgaccatgacctgcagcgcgag
cagcagcgtgaactatatgtattggtatcagcagaaaccgggcagcagcccgcgcctgctgatttatgataccagcaacct
ggccagcggtgtgccggtgcgctttagcggtagcggcagcggcaccagctatagcctgaccattagccgtatggaagcg
gaagatgcggcgacctattattgccagcagtggagcagctatccgtataccttggcggtggcaccaaactggaaatcaaa
cgt[gcggccgca]
(SEQ ID NO: 14)

[optional NotI site for cloning]

Murine IgG3 hinge
ccgaaaccgagcacccccgccgggcagcagc
(SEQ ID NO: 16)

HTH with His-tag and stop codon
ggcgaactggaagaactgctgaaacatctgaaagaactgctgaaaggcccgcgtaaaggcgaattagaggaactgctg
aaacacttaaaagaattactgaaaggcggcagcggtggagcaccacatcatcatcatcatcattaataa
(SEQ ID NO: 17)

Figure 12

Fab84 Amino acid sequences

Heavy chain
VH
qvqlqqsggglvqpggsmklscvasgftfsnywmnwvrqspekglewvaeirlksnnyathyaesvkgrftisrddskss
vylqmnnlraedtgiyyctgerawgqgttvtvss
(SEQ ID NO: 9)

CH1
astkgpsvfplapssksts ggtaalgclvkdyfpepvtvswnsgaltsgvhtfpavlqssglyslssvvtvpssslgtqtyicnv
nhkpsntkvdkkvepksc
(SEQ ID NO: 24)

Short hinge with CPP
dkthtcppcppc
(SEQ ID NO: 25)

His-tag
aaahhhhhh
(SEQ ID NO: 26)

Light chain
VL
dieltqspaimsaspgekvtmtcsasssvnymywyqqkpgssprlliydtsnlasgvpvrfsgsgsgtsysltisrmeaed
aatyycqqwssypytfgggtkleikr
(SEQ ID NO: 8)

CL
tvaapsvfifppsdeqlksgtasvvcllnnfypreakvqwkvdnalqsgnsqesvteqdskdstyslsstltlskadyekhkv
yacevthqglsspvtksfnrgec
(SEQ ID NO: 27)

Figure 13

Fab84 Nucleotide sequences

Heavy chain
VH
caggttcagctgcagcagagcggtggcggcctggtgcagccgggcggtagcatgaaactgagctgcgtggcgagcggtt
ttaccttagcaactattggatgaattgggtgcgccagagcccggaaaaaggcctggaatgggtggcggaaattcgtctga
aaagcaataactatgcgacccattatgccgaaagcgtgaaaggtcgctttaccattagccgcgatgatagcaaaagcagc
gtgtatctgcagatgaacaatctgcgcgcggaagataccggcatttattattgcaccggcgaacgcgcgtggggccaggg
caccaccgtgaccgttagcagc
(SEQ ID NO: 15)

CH1
gccagcaccaaaggtccgagcgtgtttccgctggccccgagcagcaaaagcaccagcggcggtaccgcggcgctggg
ctgtctggtgaaagattattttccggaaccggtgaccgtgagctggaatagcggtgccctgaccagcggtgttcatacctttcc
ggccgtgctgcagagcagcggcctgtatagcctgagcagcgtggtgaccgtgccgagcagcagcctgggcacccagac
ctatatctgcaatgttaatcataaaccgagcaacaccaaagttgataaaaaagtggaaccgaaaagctgt
(SEQ ID NO: 28)

His-tag
gcggcggcgcatcatcatcatcatcat
(SEQ ID NO: 29)

Light chain
VL
gatattgaactgacccagagcccggccattatgagcgcgagcccgggcgaaaaagtgaccatgacctgcagcgcgag
cagcagcgtgaactatatgtattggtatcagcagaaaccgggcagcagcccgcgcctgctgatttatgataccagcaacct
ggccagcggtgtgccggtgcgctttagcggtagcggcagcggcaccagctatagcctgaccattagccgtatggaagcg
gaagatgcggcgacctattattgccagcagtggagcagctatccgtatacctttggcggtggcaccaaactggaaatcaaa
cgt
(SEQ ID NO: 14)

CL
accgttgcggcgccgagcgtgtttatttcccgccgagcgatgaacagctgaaaagcggcaccgcgagcgtggtgtgcct
gctgaataattttatccgcgcgaagccaaagtgcagtggaaagtggataatgcgctgcagagcggcaatagccaggaa
agcgtgaccgaacaggatagcaaagatagcacctatagcctgagcagcaccctgaccctgagcaaagccgattatgaa
aaacataaagtgtatgcgtgtgaagtgacccatcagggcctgagcagcccggttaccaaaagctttaaccgtggtgaatg
c
(SEQ ID NO: 30)

Figure 14

Sequence for heavy chain of Fab84 with leucine zipper extension

QVQLQQSGGGLVQPGGSMKLSCVASGFTFSNYWMNWVRQSPEKGLEWVAEIRLKSN

NYATHYAESVKGRFTISRDDSKSSVYLQMNNLRAEDTGIYYCTGERAWGQGTTVTVSS

ASTKGPSVFPLAPSSKSTSGGTAALGCLVKDYFPEPVTVSWNSGALTSGVHTFPAVLQ

SSGLYSLSSVVTVPSSSLGTQTYICNVNHKPSNTKVDKKVEPKSCAAAPKPSTPPGSSR

MKQLEDKVEELLSKNYHLENEVARLKKLVGERGSGGAPHHHHHH (SEQ ID NO: 31)

Sequence for light chain of Fab84 (identical to monovalent Fab84)

DIELTQSPAIMSASPGEKVTMTCSASSSVNYMYWYQQKPGSSPRLLIYDTSNLASGVP

VRFSGSGSGTSYSLTISRMEAEDAATYYCQQWSSYPYTFGGGTKLEIKRTVAAPSVFIF

PPSDEQLKSGTASVVCLLNNFYPREAKVQWKVDNALQSGNSQESVTEQDSKDSTYSL

SSTLTLSKADYEKHKVYACEVTHQGLSSPVTKSFNRGEC (SEQ ID NO: 32)

Figure 15

SEQUENCE LISTING

```
<160> NUMBER OF SEQ ID NOS: 54

<210> SEQ ID NO 1
<211> LENGTH: 236
<212> TYPE: PRT
<213> ORGANISM: Artificial sequence
<220> FEATURE:
<223> OTHER INFORMATION: Synthetic sequence: Amino acid sequence of
      scFv84

<400> SEQUENCE: 1

Gln Val Gln Leu Gln Gln Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Gly Glu Arg Ala Trp Gly Gln Gly Thr Thr Val Thr Val
            100                 105                 110

Ser Ser Gly Gly Gly Gly Ser Gly Gly Gly Gly Ser Gly Gly Gly Gly
        115                 120                 125

Ser Asp Ile Glu Leu Thr Gln Ser Pro Ala Ile Met Ser Ala Ser Pro
    130                 135                 140

Gly Glu Lys Val Thr Met Thr Cys Ser Ala Ser Ser Ser Val Asn Tyr
```

```
                145                 150                 155                 160
Met Tyr Trp Tyr Gln Gln Lys Pro Gly Ser Ser Pro Arg Leu Leu Ile
                165                 170                 175

Tyr Asp Thr Ser Asn Leu Ala Ser Gly Val Pro Val Arg Phe Ser Gly
            180                 185                 190

Ser Gly Ser Gly Thr Ser Tyr Ser Leu Thr Ile Ser Arg Met Glu Ala
        195                 200                 205

Glu Asp Ala Ala Thr Tyr Tyr Cys Gln Gln Trp Ser Ser Tyr Pro Tyr
    210                 215                 220

Thr Phe Gly Gly Gly Thr Lys Leu Glu Ile Lys Arg
225                 230                 235

<210> SEQ ID NO 2
<211> LENGTH: 10
<212> TYPE: PRT
<213> ORGANISM: Mus musculus

<400> SEQUENCE: 2

Ser Ala Ser Ser Ser Val Asn Tyr Met Tyr
1               5                   10

<210> SEQ ID NO 3
<211> LENGTH: 7
<212> TYPE: PRT
<213> ORGANISM: Mus musculus

<400> SEQUENCE: 3

Asp Thr Ser Asn Leu Ala Ser
1               5

<210> SEQ ID NO 4
<211> LENGTH: 9
<212> TYPE: PRT
<213> ORGANISM: Mus musculus

<400> SEQUENCE: 4

Gln Gln Trp Ser Ser Tyr Pro Tyr Thr
1               5

<210> SEQ ID NO 5
<211> LENGTH: 5
<212> TYPE: PRT
<213> ORGANISM: Mus musculus

<400> SEQUENCE: 5

Asn Tyr Trp Met Asn
1               5

<210> SEQ ID NO 6
<211> LENGTH: 19
<212> TYPE: PRT
<213> ORGANISM: Mus musculus

<400> SEQUENCE: 6

Glu Ile Arg Leu Lys Ser Asn Asn Tyr Ala Thr His Tyr Ala Glu Ser
1               5                   10                  15

Val Lys Gly

<210> SEQ ID NO 7
<211> LENGTH: 3
<212> TYPE: PRT
<213> ORGANISM: Mus musculus
```

<400> SEQUENCE: 7

Glu Arg Ala
1

<210> SEQ ID NO 8
<211> LENGTH: 107
<212> TYPE: PRT
<213> ORGANISM: Mus musculus

<400> SEQUENCE: 8

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ser Val Asn Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Tyr Thr
                85                  90                  95

Phe Gly Gly Gly Thr Lys Leu Glu Ile Lys Arg
            100                 105

<210> SEQ ID NO 9
<211> LENGTH: 114
<212> TYPE: PRT
<213> ORGANISM: Mus musculus

<400> SEQUENCE: 9

Gln Val Gln Leu Gln Gln Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Gly Glu Arg Ala Trp Gly Gln Gly Thr Thr Val Thr Val
            100                 105                 110

Ser Ser

<210> SEQ ID NO 10
<211> LENGTH: 10
<212> TYPE: PRT
<213> ORGANISM: Mus sp.

<400> SEQUENCE: 10

Pro Lys Pro Ser Thr Pro Pro Gly Ser Ser
1               5                   10

<210> SEQ ID NO 11

<210> SEQ ID NO 11
<211> LENGTH: 47
<212> TYPE: PRT
<213> ORGANISM: Artificial sequence
<220> FEATURE:
<223> OTHER INFORMATION: Synthetic sequence: HTH with His-tag

<400> SEQUENCE: 11

```
Gly Glu Leu Glu Glu Leu Leu Lys His Leu Lys Glu Leu Leu Lys Gly
1               5                   10                  15

Pro Arg Lys Gly Glu Leu Glu Glu Leu Leu Lys His Leu Lys Glu Leu
            20                  25                  30

Leu Lys Gly Gly Ser Gly Gly Ala Pro His His His His His His
        35                  40                  45
```

<210> SEQ ID NO 12
<211> LENGTH: 15
<212> TYPE: PRT
<213> ORGANISM: Artificial sequence
<220> FEATURE:
<223> OTHER INFORMATION: Synthetic sequence: Glycine-serine linker

<400> SEQUENCE: 12

```
Gly Gly Gly Gly Ser Gly Gly Gly Gly Ser Gly Gly Gly Gly Ser
1               5                   10                  15
```

<210> SEQ ID NO 13
<211> LENGTH: 708
<212> TYPE: DNA
<213> ORGANISM: Artificial sequence
<220> FEATURE:
<223> OTHER INFORMATION: Synthetic sequence: Nucleotide sequence
      encoding SEQ ID NO: 1

<400> SEQUENCE: 13

```
caggttcagc tgcagcagag cggtggcggc ctggtgcagc cgggcggtag catgaaactg    60
agctgcgtgg cgagcggttt tacctttagc aactattgga tgaattgggt gcgccagagc   120
ccggaaaaag gcctggaatg ggtggcggaa attcgtctga aaagcaataa ctatgcgacc   180
cattatgccg aaagcgtgaa aggtcgcttt accattagcc gcgatgatag caaaagcagc   240
gtgtatctgc agatgaacaa tctgcgcgcg gaagataccg cgatttatta ttgcaccggc   300
gaacgcgcgt ggggccaggg caccaccgtg accgttagca gcggtggagg cggttcaggc   360
ggaggtggct ctggcggtgg cggatcggat attgaactga cccagagccc ggccattatg   420
agcgcgagcc cgggcgaaaa agtgaccatg acctgcagcg cgagcagcag cgtgaactat   480
atgtattggt atcagcagaa accgggcagc agcccgcgcc tgctgattta tgataccagc   540
aacctggcca gcggtgtgcc ggtgcgcttt agcggtagcg gcagcggcac cagctatagc   600
ctgaccatta gccgtatgga agcggaagat gcggcgacct attattgcca gcagtggagc   660
agctatccgt atacctttgg cggtggcacc aaactggaaa tcaaacgt              708
```

<210> SEQ ID NO 14
<211> LENGTH: 321
<212> TYPE: DNA
<213> ORGANISM: Mus musculus

<400> SEQUENCE: 14

```
gatattgaac tgacccagag cccggccatt atgagcgcga gcccgggcga aaaagtgacc    60
atgacctgca gcgcgagcag cagcgtgaac tatatgtatt ggtatcagca gaaaccgggc   120
agcagcccgc gcctgctgat ttatgatacc agcaacctgg ccagcggtgt gccggtgcgc   180
```

```
tttagcggta gcggcagcgg caccagctat agcctgacca ttagccgtat ggaagcggaa        240
gatgcggcga cctattattg ccagcagtgg agcagctatc cgtataccct tggcggtggc        300
accaaactgg aaatcaaacg t                                                  321
```

<210> SEQ ID NO 15
<211> LENGTH: 342
<212> TYPE: DNA
<213> ORGANISM: Mus musculus

<400> SEQUENCE: 15

```
caggttcagc tgcagcagag cggtggcggc ctggtgcagc cgggcggtag catgaaactg        60
agctgcgtgg cgagcggttt tacctttagc aactattgga tgaattgggt gcgccagagc        120
ccggaaaaag gcctggaatg gtggcggaa attcgtctga aaagcaataa ctatgcgacc         180
cattatgccg aaagcgtgaa aggtcgcttt accattagcc gcgatgatag caaaagcagc        240
gtgtatctgc agatgaacaa tctgcgcgcg gaagataccg gcatttatta ttgcaccggc        300
gaacgcgcgt ggggccaggg caccaccgtg accgttagca gc                          342
```

<210> SEQ ID NO 16
<211> LENGTH: 30
<212> TYPE: DNA
<213> ORGANISM: Mus sp.

<400> SEQUENCE: 16

```
ccgaaaccga gcaccccgcc gggcagcagc                                         30
```

<210> SEQ ID NO 17
<211> LENGTH: 147
<212> TYPE: DNA
<213> ORGANISM: Artificial sequence
<220> FEATURE:
<223> OTHER INFORMATION: Synthetic sequence: HTH with His-tag and stop
      codon

<400> SEQUENCE: 17

```
ggcgaactgg aagaactgct gaaacatctg aaagaactgc tgaaaggccc gcgtaaaggc        60
gaattagagg aactgctgaa acacttaaaa gaattactga aaggcggcag cggtggagca        120
ccacatcatc atcatcatca ttaataa                                            147
```

<210> SEQ ID NO 18
<211> LENGTH: 45
<212> TYPE: DNA
<213> ORGANISM: Artificial sequence
<220> FEATURE:
<223> OTHER INFORMATION: Synthetic sequence: Glycine-serine linker

<400> SEQUENCE: 18

```
ggtggaggcg gttcaggcgg aggtggctct ggcggtggcg gatcg                        45
```

<210> SEQ ID NO 19
<211> LENGTH: 18
<212> TYPE: PRT
<213> ORGANISM: Artificial sequence
<220> FEATURE:
<223> OTHER INFORMATION: Synthetic sequence: Oligopeptide linker

<400> SEQUENCE: 19

```
Gly Ser Thr Ser Gly Ser Gly Lys Pro Gly Ser Gly Glu Gly Ser Thr
 1               5                  10                  15

Lys Gly
```

<210> SEQ ID NO 20
<211> LENGTH: 15
<212> TYPE: PRT
<213> ORGANISM: Artificial sequence
<220> FEATURE:
<223> OTHER INFORMATION: Synthetic sequence: Oligopeptide linker

<400> SEQUENCE: 20

Arg Gly Arg Gly Arg Gly Arg Gly Arg Ser Arg Gly Gly Gly Ser
1               5                   10                  15

<210> SEQ ID NO 21
<211> LENGTH: 16
<212> TYPE: PRT
<213> ORGANISM: Artificial sequence
<220> FEATURE:
<223> OTHER INFORMATION: Synthetic sequence: self-associating helix

<400> SEQUENCE: 21

Gly Glu Leu Glu Glu Leu Leu Lys His Leu Lys Glu Leu Leu Lys Gly
1               5                   10                  15

<210> SEQ ID NO 22
<211> LENGTH: 110
<212> TYPE: PRT
<213> ORGANISM: Artificial sequence
<220> FEATURE:
<223> OTHER INFORMATION: Synthetic sequence: SEQ ID NO: 8 with an
      optional sequence encoded by a NotI restriction site, which was
      included for cloning purposes.

<400> SEQUENCE: 22

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ser Val Asn Tyr Met
                20                  25                  30

Tyr Trp Tyr Gln Gln Lys Pro Gly Ser Ser Pro Arg Leu Leu Ile Tyr
            35                  40                  45

Asp Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Tyr Thr
                85                  90                  95

Phe Gly Gly Gly Thr Lys Leu Glu Ile Lys Arg Ala Ala Ala
            100                 105                 110

<210> SEQ ID NO 23
<211> LENGTH: 330
<212> TYPE: DNA
<213> ORGANISM: Artificial sequence
<220> FEATURE:
<223> OTHER INFORMATION: Synthetic sequence: SEQ ID NO: 14 with an
      optional sequence encoded by a NotI restriction site, which was
      included for cloning purposes.

<400> SEQUENCE: 23
gatattgaac tgacccagag cccggccatt atgagcgcga gcccgggcga aaaagtgacc      60
atgacctgca gcgcgagcag cagcgtgaac tatatgtatt ggtatcagca gaaaccgggc     120 agcagccccgc gcctgctgat ttatgatacc agcaacctgg ccagcggtgt gccggtgcgc    180
tttagcggta gcggcagcgg caccagctat agcctgacca ttagccgtat ggaagcggaa    240

```
gatgcggcga cctattattg ccagcagtgg agcagctatc cgtataccct tggcggtggc    300
accaaactgg aaatcaaacg tgcggccgca                                     330
```

<210> SEQ ID NO 24
<211> LENGTH: 103
<212> TYPE: PRT
<213> ORGANISM: Mus musculus

<400> SEQUENCE: 24

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100
```

<210> SEQ ID NO 25
<211> LENGTH: 12
<212> TYPE: PRT
<213> ORGANISM: Artificial sequence
<220> FEATURE:
<223> OTHER INFORMATION: Synthetic sequence: Short hinge with CPP

<400> SEQUENCE: 25

```
Asp Lys Thr His Thr Cys Pro Pro Cys Pro Pro Cys
1               5                   10
```

<210> SEQ ID NO 26
<211> LENGTH: 9
<212> TYPE: PRT
<213> ORGANISM: Artificial sequence
<220> FEATURE:
<223> OTHER INFORMATION: Synthetic sequence: His-tag

<400> SEQUENCE: 26

```
Ala Ala Ala His His His His His His
1               5
```

<210> SEQ ID NO 27
<211> LENGTH: 106
<212> TYPE: PRT
<213> ORGANISM: Mus musculus

<400> SEQUENCE: 27

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60
```

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
            85                  90                  95

Val Thr Lys Ser Phe Asn Arg Gly Glu Cys
            100                 105

<210> SEQ ID NO 28
<211> LENGTH: 309
<212> TYPE: DNA
<213> ORGANISM: Mus musculus

<400> SEQUENCE: 28
gccagcacca aaggtccgag cgtgtttccg ctggccccga gcagcaaaag caccagcggc    60
ggtaccgcgg cgctgggctg tctggtgaaa gattattttc cggaaccggt gaccgtgagc   120
tggaatagcg gtgccctgac cagcggtgtt cataccttcc cggccgtgct gcagagcagc   180
ggcctgtata gcctgagcag cgtggtgacc gtgccgagca gcagcctggg cacccagacc   240
tatatctgca atgttaatca taaaccgagc aacaccaaag ttgataaaaa agtggaaccg   300
aaaagctgt                                                           309

<210> SEQ ID NO 29
<211> LENGTH: 27
<212> TYPE: DNA
<213> ORGANISM: Artificial sequence
<220> FEATURE:
<223> OTHER INFORMATION: Synthetic sequence: His-tag

<400> SEQUENCE: 29
gcggcggcgc atcatcatca tcatcat                                        27

<210> SEQ ID NO 30
<211> LENGTH: 318
<212> TYPE: DNA
<213> ORGANISM: Mus musculus

<400> SEQUENCE: 30
accgttgcgg cgccgagcgt gtttattttc cgccgagcg atgaacagct gaaaagcggc    60
accgcgagcg tggtgtgcct gctgaataat ttttatccgc gcgaagccaa agtgcagtgg   120
aaagtggata atgcgctgca gagcggcaat agccaggaaa gcgtgaccga acaggatagc   180
aaagatagca cctatagcct gagcagcacc ctgacccctga gcaaagccga ttatgaaaaa   240
cataaagtgt atgcgtgtga agtgacccat cagggcctga gcagcccggt taccaaaagc   300
tttaaccgtg gtgaatgc                                                 318

<210> SEQ ID NO 31
<211> LENGTH: 275
<212> TYPE: PRT
<213> ORGANISM: Artificial sequence
<220> FEATURE:
<223> OTHER INFORMATION: Synthetic sequence: Heavy chain of Fab84 with
      leucine zipper extension

<400> SEQUENCE: 31

Gln Val Gln Leu Gln Gln Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

```
Trp Met Asn Trp Val Arg Gln Ser Pro Glu Lys Gly Leu Glu Trp Val
             35                  40                  45

Ala Glu Ile Arg Leu Lys Ser Asn Asn Tyr Ala Thr His Tyr Ala Glu
 50                  55                  60

Ser Val Lys Gly Arg Phe Thr Ile Ser Arg Asp Asp Ser Lys Ser Ser
 65                  70                  75                  80

Val Tyr Leu Gln Met Asn Asn Leu Arg Ala Glu Asp Thr Gly Ile Tyr
                 85                  90                  95

Tyr Cys Thr Gly Glu Arg Ala Trp Gly Gln Gly Thr Thr Val Thr Val
                100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Ala Ala Pro Lys Pro Ser
    210                 215                 220

Thr Pro Pro Gly Ser Ser Arg Met Lys Gln Leu Glu Asp Lys Val Glu
225                 230                 235                 240

Glu Leu Leu Ser Lys Asn Tyr His Leu Glu Asn Glu Val Ala Arg Leu
                245                 250                 255

Lys Lys Leu Val Gly Glu Arg Gly Gly Ala Pro His His
            260                 265                 270

His His His
        275

<210> SEQ ID NO 32
<211> LENGTH: 213
<212> TYPE: PRT
<213> ORGANISM: Mus musculus

<400> SEQUENCE: 32

Asp Ile Glu Leu Thr Gln Ser Pro Ala Ile Met Ser Ala Ser Pro Gly
1               5                  10                  15

Glu Lys Val Thr Met Thr Cys Ser Ala Ser Ser Ser Val Asn Tyr Met
             20                  25                  30

Tyr Trp Tyr Gln Gln Lys Pro Gly Ser Ser Pro Arg Leu Leu Ile Tyr
             35                  40                  45

Asp Thr Ser Asn Leu Ala Ser Gly Val Pro Val Arg Phe Ser Gly Ser
 50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Tyr Thr
                 85                  90                  95

Phe Gly Gly Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125
```

```
Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 33
<211> LENGTH: 57
<212> TYPE: DNA
<213> ORGANISM: Artificial sequence
<220> FEATURE:
<223> OTHER INFORMATION: Synthetic sequence: Primer

<400> SEQUENCE: 33
tctaaataca ttcaaatatg tatccgctta tgaattaatt cttagaaaaa ctcatcg      57

<210> SEQ ID NO 34
<211> LENGTH: 57
<212> TYPE: DNA
<213> ORGANISM: Artificial sequence
<220> FEATURE:
<223> OTHER INFORMATION: Synthetic sequence: Primer

<400> SEQUENCE: 34
cgatgagttt ttctaagaat taattcataa gcggatacat atttgaatgt atttaga      57

<210> SEQ ID NO 35
<211> LENGTH: 47
<212> TYPE: DNA
<213> ORGANISM: Artificial sequence
<220> FEATURE:
<223> OTHER INFORMATION: Synthetic sequence: Primer

<400> SEQUENCE: 35
ctgtttatgt aagcagacag ttttattgtt tatgaccaaa atccctt                 47

<210> SEQ ID NO 36
<211> LENGTH: 47
<212> TYPE: DNA
<213> ORGANISM: Artificial sequence
<220> FEATURE:
<223> OTHER INFORMATION: Synthetic sequence: Primer

<400> SEQUENCE: 36
aagggatttt ggtcataaac aataaaactg tctgcttaca taaacag                 47

<210> SEQ ID NO 37
<211> LENGTH: 31
<212> TYPE: DNA
<213> ORGANISM: Artificial sequence
<220> FEATURE:
<223> OTHER INFORMATION: Synthetic sequence: Primer

<400> SEQUENCE: 37
gccgaaacaa gcgcttatga gcccgaagtg g                                  31
```

<210> SEQ ID NO 38
<211> LENGTH: 31
<212> TYPE: DNA
<213> ORGANISM: Artificial sequence
<220> FEATURE:
<223> OTHER INFORMATION: Synthetic sequence: Primer

<400> SEQUENCE: 38
ccacttcggg ctcataagcg cttgtttcgg c                              31

<210> SEQ ID NO 39
<211> LENGTH: 38
<212> TYPE: DNA
<213> ORGANISM: Artificial sequence
<220> FEATURE:
<223> OTHER INFORMATION: Synthetic sequence: Primer

<400> SEQUENCE: 39
gcccagccgg ccatggccca ggttcagctg cagcagag                       38

<210> SEQ ID NO 40
<211> LENGTH: 69
<212> TYPE: DNA
<213> ORGANISM: Artificial sequence
<220> FEATURE:
<223> OTHER INFORMATION: Synthetic sequence: Primer

<400> SEQUENCE: 40
cgatccgcca ccgccagagc cacctccgcc tgaaccgcct ccaccgctgc taacggtcac    60
ggtggtgcc                                                           69

<210> SEQ ID NO 41
<211> LENGTH: 68
<212> TYPE: DNA
<213> ORGANISM: Artificial sequence
<220> FEATURE:
<223> OTHER INFORMATION: Synthetic sequence: Primer

<400> SEQUENCE: 41
ggtggaggcg gttcaggcgg aggtggctct ggcggtggcg gatcggatat tgaactgacc    60
cagagccc                                                            68

<210> SEQ ID NO 42
<211> LENGTH: 35
<212> TYPE: DNA
<213> ORGANISM: Artificial sequence
<220> FEATURE:
<223> OTHER INFORMATION: Synthetic sequence: Primer

<400> SEQUENCE: 42
gtgatgtgcg gccgcacgtt tgatttccag tttgg                          35

<210> SEQ ID NO 43
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 43
ccggaaccgg tgaccgtgag                                           20

<210> SEQ ID NO 44
<211> LENGTH: 102

```
<212> TYPE: DNA
<213> ORGANISM: Artificial sequence
<220> FEATURE:
<223> OTHER INFORMATION: Synthetic sequence: Primer

<400> SEQUENCE: 44
tagcagccta ggttattaat gatgatgatg atgatgcgcc gccgccgggc acggcgggca        60
ggtatgggtt ttatcacagc ttttcggttc cactttttta tc                         102

<210> SEQ ID NO 45
<211> LENGTH: 26
<212> TYPE: DNA
<213> ORGANISM: Artificial sequence
<220> FEATURE:
<223> OTHER INFORMATION: Synthetic sequence: Primer

<400> SEQUENCE: 45
gccgtgcccg ccgtgcgcgg cggcgc                                            26

<210> SEQ ID NO 46
<211> LENGTH: 26
<212> TYPE: DNA
<213> ORGANISM: Artificial sequence
<220> FEATURE:
<223> OTHER INFORMATION: Synthetic sequence: Primer

<400> SEQUENCE: 46
gcgccgccgc gcacggcggg cacggc                                            26

<210> SEQ ID NO 47
<211> LENGTH: 57
<212> TYPE: DNA
<213> ORGANISM: Artificial sequence
<220> FEATURE:
<223> OTHER INFORMATION: Synthetic sequence: Primer

<400> SEQUENCE: 47
cgtgaccgtt agcagcggtg gaggcggttc agatattgaa ctgacccaga gcccggc          57

<210> SEQ ID NO 48
<211> LENGTH: 57
<212> TYPE: DNA
<213> ORGANISM: Artificial sequence
<220> FEATURE:
<223> OTHER INFORMATION: Synthetic sequence: Primer

<400> SEQUENCE: 48
gccgggctct gggtcagttc aatatctgaa ccgcctccac cgctgctaac ggtcacg          57

<210> SEQ ID NO 49
<211> LENGTH: 56
<212> TYPE: DNA
<213> ORGANISM: Artificial sequence
<220> FEATURE:
<223> OTHER INFORMATION: Synthetic sequence: Primer

<400> SEQUENCE: 49
ggtggaggcg gttcaggcgg aggtggctct gatattgaac tgacccagag cccggc           56

<210> SEQ ID NO 50
<211> LENGTH: 56
<212> TYPE: DNA
<213> ORGANISM: Artificial sequence
<220> FEATURE:
<223> OTHER INFORMATION: Synthetic sequence: Primer
```

```
<400> SEQUENCE: 50
gccgggctct gggtcagttc aatatcagag ccacctccgc ctgaaccgcc tccacc        56

<210> SEQ ID NO 51
<211> LENGTH: 34
<212> TYPE: DNA
<213> ORGANISM: Artificial sequence
<220> FEATURE:
<223> OTHER INFORMATION: Synthetic sequence: Primer

<400> SEQUENCE: 51
gccggccatg gcccaggttc agctgcagca gagc                                34

<210> SEQ ID NO 52
<211> LENGTH: 31
<212> TYPE: DNA
<213> ORGANISM: Artificial sequence
<220> FEATURE:
<223> OTHER INFORMATION: Synthetic sequence: Primer

<400> SEQUENCE: 52
ggtcagttca atatcgctgc taacggtcac g                                   31

<210> SEQ ID NO 53
<211> LENGTH: 35
<212> TYPE: DNA
<213> ORGANISM: Artificial sequence
<220> FEATURE:
<223> OTHER INFORMATION: Synthetic sequence: Primer

<400> SEQUENCE: 53
gtgatgtgcg gccgcacgtt tgatttccag tttgg                               35

<210> SEQ ID NO 54
<211> LENGTH: 10
<212> TYPE: PRT
<213> ORGANISM: Artificial sequence
<220> FEATURE:
<223> OTHER INFORMATION: Synthetic sequence: Sequence inserted into
      C-terminus of heavy constant region to create hinge region

<400> SEQUENCE: 54

Asp Lys Thr His Thr Cys Pro Pro Cys Pro
1               5                   10
```

PODOCALYXIN-LIKE-PROTEIN-1 BINDING ANTIBODY MOLECULE

FIELD OF THE INVENTION

The present invention relates to antibody molecules which bind to undifferentiated pluripotent stem cells and particularly, although not exclusively, to cytotoxic antibody molecules and methods for depleting such undifferentiated stem cells from a sample.

BACKGROUND TO THE INVENTION

Embryonic and other pluripotent stem cells have great potential in therapy. Such cells can be directed to differentiate into specific cell types and offer the possibility of a renewable source of replacement cells and tissues, for example, for use in regenerative medicine to repair tissues which have been damaged by disease or injury.

However, the use of embryonic stem cells in medicine is limited due to the significant ethical concerns associated with the use of embryos. Recently, the Yamanaka Lab[2] and Thomson Lab[3] demonstrated that human fibroblasts can be reprogrammed by the transient overexpression of a small number of genes into induced pluripotent stem cells (IPSCs) which functionally and phenotypically resemble embryonic stem cells (ESCs). Thus, pluripotent stem cells can be obtained without the need for the destruction of embryos.

Some IPSCs, like hESC, express Oct-4 and other cell surface markers, such as Tra-1-60/81 and SSEA-3/4. However, IPSCs are not identical to ESCs, as shown by a slower doubling time[11], differences in the global gene-expression patterns[2,3] and DNA methylation status[2]. It remains unknown whether nuclear reprogramming is complete[10], and thus whether IPSCs follow a similar pathway to hESCs during differentiation.

This important breakthrough raises the possibility that cellular therapies using patient-specific input cells may be a reality in the future. Unlike hESC where there are ethical concerns and possible issues of immune rejection, IPSCs can be generated from a donor, reprogrammed, differentiated to the appropriate cell type and transplanted back into the donor.

Prior to the publication of reports that IPSCs had been successfully generated from human cells, we described the generation of a panel of monoclonal antibodies (mAbs) against surface antigens on undifferentiated hESCs[1] in WO 2007/102787, the contents of which is hereby incorporated in this application by reference. These mAbs showed strong reactivity against undifferentiated, but not differentiated (embryoid bodies), hESC lines.

The mAbs did not cross react with mouse fibroblasts, and showed weak to no reactivity against human embryonal carcinoma cells. Thus these mAbs exhibited very high specificity binding to hESCs, and this binding was lost as the hESCs differentiated. The monoclonal antibody, mAb 84, is an IgM which specifically binds and kills undifferentiated human embryonic stem cells (hESC) (Tan, 2009, [29]). mAb 84 induced cell death of undifferentiated, but not differentiated hESC within 30 min of incubation, and immunoprecipitation of the mAb-antigen complex revealed that the antigen is podocalyxin-like protein-1 (PODXL). Importantly, the absence of tumour formation is observed when hESC were treated with mAb 84 prior to transplantation into SCID mice. This earlier data indicates that mAb84 may be useful in eliminating residual undifferentiated hESC from differentiated cell populations for clinical applications.

Although undifferentiated stem cells may be used in cell therapy, it is considered to be beneficial to use cells which have started to differentiate, or are differentiated. Methods of encouraging stem cells to differentiate into particular cell lineages are well known in the art. Once the differentiation process has started or proceeded, it is beneficial to remove or destroy undifferentiated hESCs in a sample which may otherwise form undesirable teratomas. Teratomas typically contain a mixture of differentiated or partly differentiated cell types. Despite the potential of IPSC therapy, the problem of teratoma formation by residual IPSC after differentiation remains and needs to be addressed.

Thus, mAb 84 can potentially be used for separation and removal of residual undifferentiated hESC from differentiated cell populations.

Thus, it can be seen that it is useful to identify, isolate or separate undifferentiated pluripotent stem cells (since they can be used themselves in therapy or can be encouraged to differentiate into a particular cell lineage which can be used in therapy). It is also useful to remove or destroy undifferentiated pluripotent stem cells from a mixture of cells where some of the cells have started to differentiate, or are differentiated, since these differentiated cells are useful in therapy.

SUMMARY OF THE INVENTION

The present inventors have discovered an antibody molecule, based on a fragment of mAb84, which specifically binds to podocalyxin-like protein-1 (PODXL) and is specifically cytotoxic against both undifferentiated human embryonic stem cells (hESCs) and induced pluripotent stem cells (IPSCs).

Furthermore, the inventors have shown that the cytotoxic properties of antibody molecules described herein may be influenced by the valency and flexibility of the antibody molecule, as well as ability to bind PODXL.

Accordingly, antibody molecules described herein may be useful for binding, identifying, isolating, separating, purifying, enriching or removing undifferentiated pluripotent stem cells, for example from a sample or population containing differentiated and undifferentiated hESCs and/or IPSCs. Furthermore, antibody molecules may be useful for identifying, isolating, separating, purifying, or enriching differentiated pluripotent stem cells.

Preferably, an antibody molecule described herein destroys, or is capable of destroying undifferentiated pluripotent stem cells such as undifferentiated hESCs and/or IPSCs.

An aspect of the invention provides an antibody molecule which binds PODXL and includes two monomers, each monomer including an Fv antibody fragment (and/or an Fv-containing antibody fragment) connected to a dimerizing portion, wherein the dimerizing portions interact to form the antibody molecule, wherein each Fv antibody fragment has a VH region and a VL region, and has one or more of CDR amino acid sequences (i) to (vi):

```
(i) VL CDR1:
                                  (SEQ ID NO: 2)
SASSSVNYMY;

(ii) VL CDR2:
                                  (SEQ ID NO: 3)
DTSNLAS;
```

-continued (iii) VL CDR3:
QQWSSYPYT; (SEQ ID NO: 4)

(iv) VH CDR1:
NYWMN; (SEQ ID NO: 5)

(v) VH CDR2:
EIRLKSNNYATHYAESVKG; (SEQ ID NO: 6)

(vi) VH CDR3:
ERA; (SEQ ID NO: 7)

or has a variant of one or more of (i) to (vi).

In some embodiments, an Fv antibody fragment is an scFv fragment.

A dimerizing portion of a monomer described herein may comprise a dimerization domain. A dimerization domain may, for example, be a helix-turn-helix (HTH) motif. Other dimerization domains include coiled-coil motifs, leucine zipper motifs, of hand motifs, p53 motifs or one or more CPP motifs, for example, a (CPP)$_3$ motif.

The antibody molecule may also comprise a linker which connects an antibody fragment to a dimerization domain. For example, a linker may be a linker peptide. The linker may be a flexible linker or flexible linker peptide such as an immunoglobulin hinge region.

Another aspect of the invention provides an antibody molecule which binds PODXL and includes two monomers, each monomer including an antibody fragment connected to a dimerizing portion via a flexible linker, wherein the dimerizing portions interact to form the antibody molecule, wherein each antibody fragment has a VH region and a VL region, and has one or more of CDR amino acid sequences (i) to (vi):

(i) VL CDR1:
SASSSVNYMY; (SEQ ID NO: 2)

(ii) VL CDR2:
DTSNLAS; (SEQ ID NO: 3)

(iii) VL CDR3:
QQWSSYPYT; (SEQ ID NO: 4)

(iv) VH CDR1:
NYWMN; (SEQ ID NO: 5)

(v) VH CDR2:
EIRLKSNNYATHYAESVKG; (SEQ ID NO: 6)

(vi) VH CDR3:
ERA; (SEQ ID NO: 7)

or has a variant of one or more of (i) to (vi).

In some embodiments, an antibody fragment is an Fv fragment such as an scFv fragment or a dsFv fragment. In some embodiments, an antibody fragment is an Fv-containing fragment, such as an Fab fragment.

An antibody molecule including two monomers, as described herein, may be a miniantibody. For example, an antibody molecule may be a miniantibody which comprises a first monomer joined to a second monomer via interacting dimerizing portions.

The antibody molecule may be dimeric and/or may be multimeric, i.e. it may comprise two or more monomers. A multimeric antibody molecule may comprise a dimer. The antibody molecule may, for example, be tetrameric and may comprise four monomers.

Preferably, the antibody molecule is a dimeric antibody molecule including two monomers.

Dimerizing portions of monomers may form an antibody molecule by interacting through covalent and/or non-covalent interactions: For example, the dimerizing portion of a first monomer may interact with the dimerizing portion of a second monomer through any form of non-covalent interaction such as hydrogen bonding, van der Waals forces, ionic bonding or hydrophobic interactions. Alternatively, or in addition, the dimerizing portion of a first monomer may interact with the dimerizing portion of a second monomer through covalent bonding, such as cross-linking. For example, a first monomer may be covalently bonded to a second monomer via one or more disulphide bonds.

Dimerizing portions may form an antibody molecule by interacting to form a flexible link, or a flexible interaction, between a first monomer and a second monomer.

Preferably, an antibody molecule of the invention is smaller than a whole antibody, such as a typical IgG antibody. Such antibody molecules and fragments may penetrate better into cell-clumps or tissues, for example into samples, tissues or clumps of cells containing differentiated, partially differentiated and/or undifferentiated pluripotent stem cells. For example a dimeric antibody molecule may be of less than 150 kDa. A dimeric antibody molecule may be of 140 kDa or less, 130 kDa or less, 120 kDa or less, 110 kDa or less, 100 kDa or less, 90 kDa or less, 80 kDa or less, 70 kDa or less, 60 kDa or less, 50 kDa or less. In some embodiments, a dimeric antibody molecule may be of about 65 kDa or less. The size of an antibody molecule may be expressed as an apparent molecular weight.

An antibody fragment may have a variant of one or more of (i) to (vi). For example, one or more amino acids of one or more of the CDR sequences of SEQ ID NOs: 2 to 7 may be replaced by a different amino acid, or may be deleted.

A variant of SEQ ID NO: 7 may have one amino acid of SEQ ID NO: 7 replaced (i.e. substituted) with another amino acid. For example, a variant of SEQ ID NO: 7 may have about 66% or greater sequence identity with the entire length of SEQ ID NO: 7. A substitution may be a conservative substitution. For example, in the VH CDR3 sequence ERA (SEQ ID NO: 7), E may be substituted for D; R may be substituted for K; and A may be substituted for V. The VH region of an antibody fragment may have the VH CDR3 amino acid sequence of mAb84 or a variant thereof. Preferably, the VH region of an antibody fragment has the VH CDR3 amino acid sequence (vi):

In some embodiments, a variant is an amino acid sequence having at least about 70% sequence identity, at least about 75% sequence identity, at least about 80% sequence identity, at least about 85% sequence identity, or at least about 90% sequence identity with SEQ ID NO:2, SEQ ID NO:3, SEQ ID NO:4, SEQ ID NO:5, or SEQ ID NO:6. Sequence identity may be calculated along the entire length of the given sequence, i.e. with the entire length of any of SEQ ID NOs: 2 to 6. For example, an antibody fragment may have a variant of one or more of the CDR sequences of SEQ ID NOs: 2 to 6 in which no more than about 5%, no more than about 10%, no more than about 15%, no more than about 20%, no more than about 25%, or no more than about 30% of the amino acids differ from the amino acids of SEQ ID NO:2, SEQ ID NO:3, SEQ ID NO:4, SEQ ID NO:5, or SEQ ID NO:6.

In some embodiments, an antibody fragment may have a variant of one or more of (i) to (v) in which one or two or three amino acids of one or more of (i) to (v) are replaced with another amino acid.

An Fv antibody fragment has a VH region and a VL region which may form an antigen binding site. The VH and VL regions may be connected by a linker (e.g. an scFv fragment) and/or may be connected by a disulphide link (e.g. a dsFv fragment). An antibody fragment may be a fragment containing an Fv portion of an antibody—i.e. a VH and a VL region—and may further contain one or more constant regions or parts thereof. For example, an antibody fragment may be an Fab fragment. An Fab antibody fragment has a VH region, a VL region, a CL region and a CH1 region.

An scFv antibody fragment has a VH region, a VL region and a linker, which connects the VH and VL regions. For example, the linker may be an oligopeptide linker of about 13 to about 15 amino acids, or more. In some embodiments, the scFv fragment has a $(G_4S)_3$ linker.

The VH region of an antibody fragment described herein may have the VH CDR3 amino acid sequence ERA as set out in SEQ ID NO: 7 or may have a variant VH CDR3 amino acid sequence in which one amino acid of SEQ ID NO: 7 is replaced with another amino acid. The VH region may further comprise:

```
(iv) VH CDR1:
                            (SEQ ID NO: 5)
NYWMN;

(v) VH CDR2:
                            (SEQ ID NO: 6)
EIRLKSNNYATHYAESVKG;
``` or a variant thereof in which one or two or three amino acids in one or more of the sequences (iv) to (v) are replaced with another amino acid.

The VL region of an antibody fragment may comprise:

```
(i) VL CDR1:
                            (SEQ ID NO: 2)
SASSSVNYMY;

(ii) VL CDR2:
                            (SEQ ID NO: 3)
DTSNLAS;

(iii) VL CDR3:
                            (SEQ ID NO: 4)
QQWSSYPYT;
``` or a variant thereof in which one or two or three amino acids in one or more of the sequences (i) to (iii) are replaced with another amino acid.

An antibody fragment may comprise the VH and VL CDR sequences of mAb84. For example, an antibody fragment may comprise:

```
(i) VL CDR1:
                            (SEQ ID NO: 2)
SASSSVNYMY;

(ii) VL CDR2:
                            (SEQ ID NO: 3)
DTSNLAS;

(iii) VL CDR3:
                            (SEQ ID NO: 4)
QQWSSYPYT;

(iv) VH CDR1:
                            (SEQ ID NO: 5)
NYWMN;

(v) VH CDR2:
                            (SEQ ID NO: 6)
EIRLKSNNYATHYAESVKG;
and (vi) VH CDR3:
                            (SEQ ID NO: 7)
ERA.
```

Another aspect of the invention provides a monomeric antibody molecule or a monomer which includes an antibody fragment, for example an Fv antibody fragment, connected to a dimerizing portion, wherein the antibody fragment has a VH region and a VL region, and has one or more of CDR amino acid sequences (i) to (vi):

```
(i) VL CDR1:
                            (SEQ ID NO: 2)
SASSSVNYMY;

(ii) VL CDR2:
                            (SEQ ID NO: 3)
DTSNLAS;

(iii) VL CDR3:
                            (SEQ ID NO: 4)
QQWSSYPYT;

(iv) VH CDR1:
                            (SEQ ID NO: 5)
NYWMN;

(v) VH CDR2:
                            (SEQ ID NO: 6)
EIRLKSNNYATHYAESVKG;

(vi)
VH CDR3:
``` or has a variant of one or more of (i) to (vi).

A first monomer may be capable of dimerizing with a second monomer to form an antibody molecule including two monomers, e.g. a dimeric or multimeric antibody molecule, as disclosed herein. For example, a dimerizing portion of a first monomer may be capable of interacting with a dimerizing portion of a second monomer to form an antibody molecule including two monomers as disclosed herein.

In another aspect of the invention there is provided an isolated nucleic acid which comprises a nucleotide sequence encoding an antibody molecule as described herein. For example, an isolated nucleic acid may comprise a nucleotide sequence encoding a monomer as described herein. Also provided are expression vectors comprising nucleic acids of the invention as well as host cells comprising a nucleic acid or an expression vector of the invention. Such nucleic acids, expression vectors and/or host cells may be used to express an antibody molecule of the invention.

Another aspect of the invention provides a method of binding an undifferentiated pluripotent stem cell or cells in a sample containing such cells, the method comprising providing an antibody molecule of the present invention and contacting the sample with the antibody molecule under conditions permitting binding of the antibody molecule to an undifferentiated pluripotent stem cell.

A pluripotent stem cell may be a mammalian pluripotent stem cell, such as a human, mouse, or rat pluripotent stem cell. In some preferred embodiments, a pluripotent stem cell is a human pluripotent stem cell.

The method may be performed in vitro. For example, a sample may be from a mammalian embryo, may be mammalian embryonic tissue, or may be a sample of cells cultivated in vitro. A sample may contain undifferentiated pluripotent stem cells, pluripotent stem cells which are differentiated, pluripotent stem cells which are undergoing differentiation and/or non-pluripotent cells. A sample may contain cells or may be likely to contain cells which have the potential to form teratomas, for example, human pluripotent stem cells. A sample may contain human pluripotent stem cells and/or cells differentiated from human pluripotent stem cells. For example, a sample may comprise hESCs and/or IPSCs. Furthermore, a sample may contain cells differentiated from hESCs and/or IPSCs.

The method may be useful for identifying, isolating, separating, purifying, enriching or removing undifferentiated pluripotent stem cells from a sample. Furthermore, methods of binding an undifferentiated pluripotent stem cell may be useful for identifying, isolating, separating, purifying, or enriching differentiated pluripotent stem cells. Preferably, these methods involve an antibody molecule which includes two monomers binding to PODXL, for example to PODXL expressed on the surface of undifferentiated human pluripotent stem cells.

In some embodiments, the method may further comprise a step of isolating, identifying, separating, purifying, enriching and/or removing an undifferentiated pluripotent stem cell. For example, an undifferentiated pluripotent stem cell(s) may be identified by virtue of being bound to the antibody molecule.

The method may further comprise a step of isolating, identifying, separating, purifying and/or enriching differentiated pluripotent stem cells. For example, a differentiated pluripotent stem cell(s) in a sample may be enriched, separated or purified by virtue of an undifferentiated pluripotent stem cell(s) being bound to the antibody molecule, being isolated or separated from the sample, and/or being removed from the sample.

Isolated, purified or enriched undifferentiated pluripotent stem cell(s) obtained by these methods are provided. Isolated, purified or enriched differentiated pluripotent stem cell(s) obtained by these methods are also provided.

Also provided are methods of enriching pluripotent stem cells that have undergone or are undergoing differentiation from a sample comprising undifferentiated pluripotent stem cells and pluripotent stem cells that have undergone or are undergoing differentiation, and methods of preparing compositions containing cells differentiated from undifferentiated pluripotent stem cells which contain substantially no undifferentiated pluripotent stem cells.

A method of the invention may involve cells bound to the antibody molecule being destroyed by virtue of being bound to the antibody molecule. For example, a sample may be enriched in pluripotent stem cells that have undergone or are undergoing differentiation, and/or undifferentiated pluripotent stem cells may be removed from a sample or a population of cells by virtue of undifferentiated pluripotent stem cells bound to a dimeric antibody molecule of the invention being destroyed.

Another aspect of the invention provides a method of destroying an undifferentiated pluripotent stem cell or cells. Preferably, a method of destroying undifferentiated pluripotent stem cell(s) involves allowing an antibody molecule including two monomers, as described herein, to bind to an undifferentiated pluripotent stem cell and to destroy the said cell.

Also provided are compositions containing cells differentiated from undifferentiated pluripotent stem cells which compositions contain substantially no undifferentiated pluripotent stem cells, which may be produced by methods of the present invention.

BRIEF DESCRIPTION OF THE FIGURES

Embodiments and experiments illustrating the principles of the invention will now be discussed with reference to the accompanying figures in which:

FIG. 9. shows primers used in construction of different Fab84 and scFv84 vectors.

FIG. 10. shows the amino acid sequence of scFv84

FIG. 11. shows amino acid sequences of the components of scFv84-HTH. An optional sequence encoded by a NotI restriction site, which was included for cloning purposes, is shown in square brackets [ ] and is not part of the VL amino acid sequence as set out in SEQ ID NO: 8. The VL amino acid sequence including the sequence in square brackets is SEQ ID NO: 22.

FIG. 12. shows nucleotide sequences encoding the components of scFv84-HTH. An optional nucleic acid sequence encoding a NotI restriction site, which was included for cloning purposes, is shown in square brackets [ ] and is not part of the VL nucleotide sequence as set out in SEQ ID NO:14. The VL nucleotide sequence including the sequence in square brackets is SEQ ID NO: 23.

FIG. 13. shows amino acid sequences of the components of Fab84 and the optional CPP tail and His tag.

FIG. 14. shows nucleotide sequences encoding the components of Fab84 and the optional CPP tail and His tag.

FIG. 15. shows the amino acid sequence of the heavy chain of Fab84 with the leucine zipper extension (SEQ ID NO: 31) and the amino acid sequence of the light chain of Fab84 (SEQ ID NO: 32).

DETAILED DESCRIPTION OF THE INVENTION

Antibody Molecules

Figure 1:
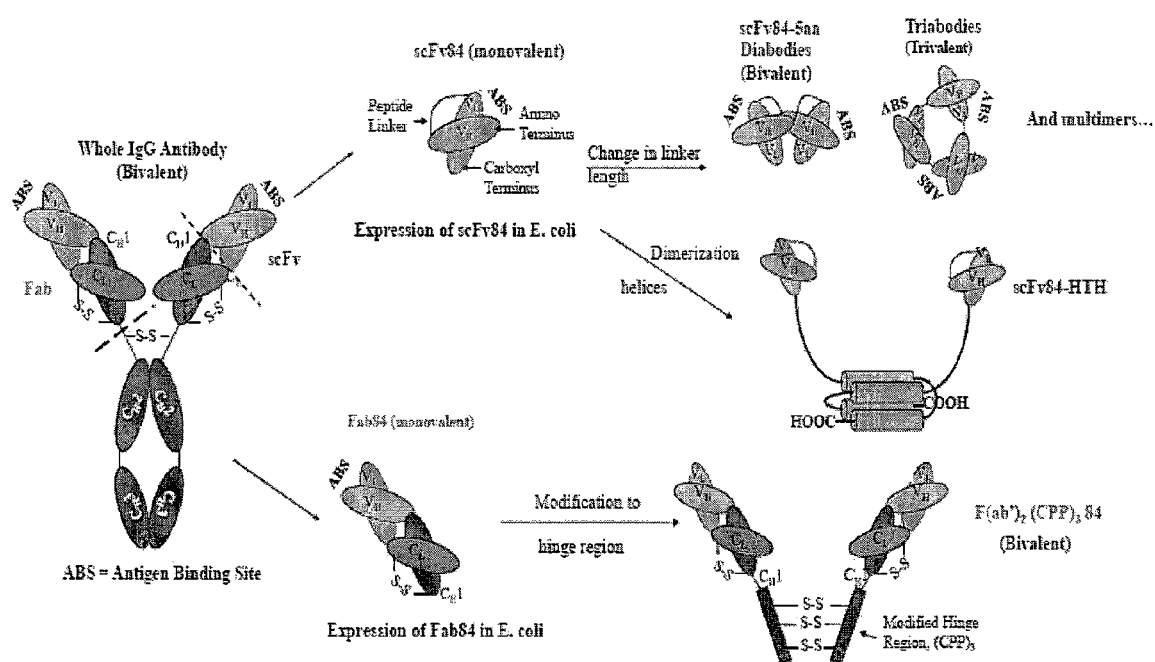
FIG. 1. shows the format of different antibody molecules based on various antibody fragments.

The present application is concerned with antibody molecules and their uses. The present inventors have generated various antibody molecules which are based on fragments of the monoclonal antibody mAb84.

Antibody molecules include binding members or substances having an antibody antigen-binding site with the required specificity and/or binding to a target antigen. The structure of antibodies and antibody fragments is well known. Generally, an antibody molecule comprises an immunoglobulin heavy chain variable region (VH domain or VH region) which is paired with a light chain variable region (VL domain or VL region) to provide an antibody antigen binding domain or binding site. Antibody molecules may further comprise antibody constant regions or parts thereof. For example, a VL domain may be attached at its C-terminal end to antibody light chain constant domains including human Cκ or Cλ chains, preferably Cλ chains. Similarly, an antibody molecule based on a VH domain may be attached at its C-terminal end to all or part of an immunoglobulin heavy chain derived from any antibody isotype. Examples of antibody molecules, some of which are provided herein, include immunoglobulin isotypes and their isotypic subclasses; antibody fragments, such as Fab, Fab', Fab'-SH, scFv, dsFv, Fv, dAb and Fd; engineered antibody molecules, such as $Fab_2$, $Fab_3$, diabodies, triabodies, tetrabodies and minibodies; and any other polypeptide comprising an antibody antigen-binding site, whether natural or wholly or partially synthetic. Various antibody molecules, fragments and formats have been described, see for example Plückthun (1997), incorporated herein by reference.

An antibody molecule of the present invention, whether in monomeric, dimeric or multimeric form, includes an antibody fragment. An antibody fragment may be, or may be based on part of a whole antibody. An antibody fragment may not be a whole antibody. Preferably, an antibody fragment is smaller than a whole antibody. Preferably, an antibody molecule and/or an antibody fragment described herein does not include an antibody Fc region. An antibody fragment may not include a whole Fc region, or a part of an Fc region. For example, an antibody fragment may include less than 100%, less than 80%, less than 60%, less than 40%, less than 20% or less than 10% of an Fc region. The Fc region is the tail region of an antibody which can interact with cell surface receptors and complement proteins and is made up of the second and third constant regions of the antibody heavy chain. The Fc region is not directly involved in antigen binding.

Preferably, an antibody fragment of the invention has an Fv region. In some embodiments, an antibody fragment of the invention consists of an Fv region. An Fv region corresponds to the region of an antibody consisting of a VH and a VL domain, which together form an antigen binding site.

The VH and VL of an Fv region may be directly connected (e.g. by covalent bonding) to form an Fv fragment. For example, an Fv fragment may be an scFv fragment or a dsFv fragment, as described herein. Alternatively, or in addition, the VH and VL of an Fv region may be part of an Fv-containing fragment, such as an Fab fragment. An antibody fragment may consist of an Fv fragment, such as an scFv or dsFv fragment, or may consist of an Fv-containing fragment such as an Fab fragment.

An antibody molecule of the invention may not include an antibody constant region, or may not include a whole antibody constant region. For example, a monomer may consist of an Fv fragment and a dimerizing portion, as described herein.

An antibody molecule may include a single-chain variable fragment (scFv). scFv fragments are antibody fragments wherein a VH region is fused to a VL region. VH and VL regions are linked by an oligopeptide linker which allows the two regions or domains to associate to form an antigen binding site (Bird et al, Science, 242, 423-426, 1988; Huston et al, PNAS USA, 85, 5879-5883, 1988). VH and VL regions may be linked in any order. For example, an scFv may be in VH-linker-VL format or in VL-linker-VH format. An scFv fragment of the present invention may not have an antibody constant region.

An oligopeptide linker between the VH and VL regions of an scFv fragment may be at least 13 amino acids, or at least 14 amino acids in length, and is preferably 14 or 15 amino acids or more in length. For example, the oligopeptide linker may be from 13 to 25 amino acids in length. The oligopeptide linker may be in the format $(G_4S)_n$, and n may, for example, be 3, 4, 5 or greater than 5. Preferably, the oligopeptide linker is a flexible oligopeptide, such as a serine and/or glycine-rich oligopeptide. For example, the oligopeptide linker may be $(G_4S)_3$ (SEQ ID NO: 12), GSTSGSGKPGSGEGSTKG (SEQ ID NO: 19) (Whiltlow et al., 1993, Protein Engineering, vol. 6 ao. 8 pp. 989-995), or RGRGRGRGRSRGGGS (SEQ ID NO: 20) (Shen et al., 2008, Anal Chem.; 80(6): 1910-1917).

In other embodiments, an antibody fragment may be a dsFv fragment wherein a VH and a VL domain are linked by one or more disulphide bonds.

In other embodiments, an antibody fragment may be an Fab fragment. Fab fragments are antibody fragments having a VL, a VH, a CL and a CH1 domain.

Antibody molecules include chimeric molecules comprising an antigen binding domain, or equivalent, fused to another polypeptide. Cloning and expression of chimeric antibodies are described in EP-A-0120694 and EP-A-0125023.

Antibody molecules of the present invention include antibody molecules which are monomers—i.e. monomeric antibody molecules—and antibody molecules which include two monomers, which may be referred to as dimeric antibody molecules. Furthermore, antibody molecules may be multimers such as dimers or tetramers. A multimer or a tetramer may, for example, include more than one dimeric antibody molecule. A monomer may comprise an antigen binding domain, or equivalent, e.g. an Fv fragment, fused to a dimerization domain. Preferably, a monomer is monovalent, i.e. it has one antigen binding domain. A dimeric or multimeric (e.g. tetrameric) antibody molecule may comprise a pair of monomers which interact to form a dimer. For example, a dimeric antibody molecule may have two Fv fragments, connected by interacting dimerization domains. Preferably, a dimer is bivalent (or divalent), i.e. it has two antigen binding domains. A multimer may have two or more monomers and thus may have two or more antigen binding domains—i.e. a multimer may be multivalent.

The antibody fragments of a multimeric (e.g. dimeric) antibody molecule may be of identical amino acid sequence, or may have one or more identical complementarity determining region (CDR) amino acid sequences. For example, a dimeric antibody molecule with identical or substantially identical antibody fragments may be referred to as a homodimer or a homodimeric antibody molecule. Alternatively, the fragments in a multimeric antibody molecule may be of different amino acid sequence. For example, they may have different CDR sequences, different framework region sequences, and/or different VH and/or VL region sequences. Preferably, an antibody fragment of the present invention has one or more of the CDR amino acid sequences of mAb84, and/or one or more variants of those CDR amino acid sequences.

In general, the VH region of an antibody plays a significant role in the binding of an antibody to an antigen. The CDR3 region of a VH domain has been found to be more diverse than the CDR1 and CDR2 regions, and thus in most antibodies provides specificity for the target of the antibody. Thus antibody molecules of the invention preferably have the VH CDR3 region of the mAb84 antibody and may have one or both remaining CDRs (CDR1 and/or CDR2) of the VH regions of the mAb84 antibody.

The amino acid sequence (and encoding polynucleotide sequence) of the whole mAb84 antibody, and the $V_H$ and $V_L$ chains of mAb84 are known, e.g. see WO 2007/102787 and SEQ ID NOs: 8 and 9 of the present disclosure.

The structure of an antibody molecule which has a CDR as described herein will generally be of a heavy or light chain sequence of an antibody molecule or substantial portion thereof in which the CDR is located at a location corresponding to the CDR of naturally occurring VH and VL antibody variable domains encoded by rearranged immunoglobulin genes. The structures and locations of immunoglobulin variable domains may be determined by reference to Kabat, E. A. et al, Sequences of Proteins of Immunological Interest. 4th Edition. US Department of Health and Human Services. 1987, and updates thereof. A number of academic and commercial on-line resources are available to query this database. For example, see Martin, A. C. R. Accessing the Kabat Antibody Sequence Database by Computer *PROTEINS: Structure, Function and Genetics,* 25 (1996), 130-133 and the associated on-line resource, currently at the web address of http://www.bioinforg.uk/abs/simkab.html.

Generally, an antibody molecule comprises a VH domain which is paired with a VL domain to provide an antibody antigen binding domain. For example, the mAb84 VH domain (SEQ ID NO: 9) may be paired with the mAb84 VL domain (SEQ ID NO: 8), so that an antibody antigen binding site is formed which comprises both the mAb84 VH and VL domains. Alternatively, the mAb84 VH domain may be paired with a VL domain other than the mAb84 VL domain. Light-chain promiscuity is well established in the art.

An antibody molecule of the invention may be a monomer (a monomeric antibody molecule) which includes an antibody fragment, or an antibody molecule which is formed from two such monomers. The antibody fragment may have one or more of the following CDR amino acid sequences:

(i) VL CDR1:
                                                     (SEQ ID NO: 2)
SASSSVNYMY;

(ii) VL CDR2:
                                                   (SEQ ID NO: 3)
DTSNLAS;

(iii) VL CDR3:
                                                   (SEQ ID NO: 4)
QQWSSYPYT;

(iv) VH CDR1:
                                                   (SEQ ID NO: 5)
NYWMN;

(v) VH CDR2:
                                                   (SEQ ID NO: 6)
EIRLKSNNYATHYAESVKG;

(vi) VH CDR3:
                                                   (SEQ ID NO: 7)
ERA or may have a variant of one or more of (i) to (vi).

Thus, an antibody fragment may have the amino acid sequences i) to iii), and/or the amino acid sequences iv) to vi), or preferably the amino acid sequences i) to vi).

Preferably, the antibody fragment has at least one light chain variable region incorporating the following CDRs:

CDR1:
                                                   (SEQ ID NO: 2)
SASSSVNYMY

CDR2:
                                                   (SEQ ID NO: 3)
DTSNLAS

CDR3:
                                                   (SEQ ID NO: 4)
QQWSSYPYT

Preferably, the antibody fragment has at least one heavy chain variable region incorporating the following CDRs:

CDR1:
                                                   (SEQ ID NO: 5)
NYWMN

CDR2:
                                                   (SEQ ID NO: 6)
EIRLKSNNYATHYAESVKG

CDR3:
                                                   (SEQ ID NO: 7)
ERA

An antibody molecule may have a VH region having sequence identity with the amino acid sequence as set out in SEQ ID NO: 9 and/or a VL region having sequence identity with the amino acid sequence as set out in SEQ ID NO: 8. For example, an antibody molecule of the invention may include a VH amino acid sequence having a sequence identity of at least about 70%, at least about 75%, at least about 80%, at least about 85%, at least about 90%, at least about 95%, or about 100% with SEQ ID NO: 9 and/or a VL amino acid sequence having a sequence identity of at least about 70%, at least about 75%, at least about 80%, at least about 85%, at least about 90%, at least about 95%, or about 100% with SEQ ID NO: 8.

More preferably, the antibody molecule has a heavy chain variable region comprising the amino acid sequence as shown in SEQ ID NO: 9. Yet more preferably, the antibody molecule has a light chain variable region as shown in SEQ ID NO: 8.

In some embodiments the antibody fragment is an scFv fragment and may be a mAb84-derived scFv fragment, referred to herein as scFv84. An scFv fragment of the invention may be an scFv antibody fragment having a sequence identity of at least about 70%, at least about 75%, at least about 80%, at least about 85%, at least about 90%, at least about 95%, or about 100% with SEQ ID NO: 1. In some preferred embodiments the scFv fragment has the amino acid sequence as set out, or substantially as set out in SEQ ID NO:1.

In some embodiments, the antibody fragment is an Fab fragment and may be a mAb84-derived Fab fragment, referred to herein as Fab84. An Fab fragment has a VH, a CH1, a VL and a CL region. In some embodiments, an Fab fragment has a VH region having sequence identity with the amino acid sequence as set out in SEQ ID NO: 9 and/or a VL region having sequence identity with the amino acid sequence as set out in SEQ ID NO: 8, as described herein. In some embodiments, the CH1 region has an amino acid sequence as set out in SEQ ID NO: 24, or has an amino acid sequence having sequence identity to SEQ ID NO: 24. In some embodiments, the CL region has an amino acid sequence as set out in SEQ ID NO: 27, or has an amino acid sequence having sequence identity to SEQ ID NO: 27. For example, said sequence identity may be at least about 70%, at least about 75%, at least about 80%, at least about 85%, at least about 90%, at least about 95%, or about 100% with the given sequence (e.g. SEQ ID NO: 8, 9, 24, or 27). In some preferred embodiments the Fab fragment has the VH amino acid sequence as set out, or substantially as set out in SEQ ID NO: 9; has the CH1 amino acid sequence as set out, or substantially as set out in SEQ ID NO: 24; has the VL amino acid sequence as set out, or substantially as set out in SEQ ID NO: 9; and has the CL amino acid sequence as set out, or substantially as set out in SEQ ID NO: 27.

By "substantially as set out" it is meant that the relevant amino acid or nucleotide sequence of the antibody molecule or encoding the antibody molecule (e.g. a CDR or VH or VL domain) will be either identical or highly similar to the specified regions of which the sequence is set out herein.

Using techniques of recombinant DNA technology, it is possible to take antibody molecules, including monoclonal antibodies and fragments thereof, and to produce other antibody molecules or chimeric molecules which retain the specificity of the original antibody. Such techniques may involve introducing DNA encoding the CDRs described herein to the framework regions of a different antibody molecule. Thus, it will be appreciated that the CDR sequences above may be used to generate further synthetic antibody molecules, which may bind PODXL. Light and heavy chain CDRs 1-3 listed above, or variants as described herein, may be particularly useful in conjunction with framework regions other than those of mAb84. Accordingly, light or heavy chains having CDRs as described herein may possess an alternative framework region. Suitable framework regions are well known in the art and are described for example in M. Lefranc & G. Lefranc (2001) "The Immunoglobulin FactsBook", Academic Press, incorporated herein by reference.

For example, CDRs may be grafted into a human framework region. The human framework region may be selected by a number of methods, e.g. by comparing the mouse framework region or mouse V region sequences with known human framework or V region sequences and selecting a human framework region which has the highest, or one of the highest degrees of amino acid similarity or identity. Modifications to framework regions of native human sequences may be made in order to further optimize the resulting CDR-grafted antibody molecules.

Framework regions of antibody molecules of the invention may also include glycosylation sequences that include one or more glycosylation sites. Depending upon the host cell in which the antibody is expressed, the pattern of glycosylation may vary. Thus nucleic acid constructs that encode glycosylation sites may be modified to remove the site or alternatively such sites may be introduced into the protein. For example, N-glycosylation sites in eukaryotic proteins are characterized by an amino acid triplet Asn-X-Y, wherein X is any amino acid except Pro and Y is Ser or Thr. Appropriate substitutions, additions or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846.

A substantial portion of the variable domain of an antibody molecule will comprise at least three CDR regions, together with intervening framework regions. Preferably, the portion will also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of antibody molecules made by recombinant DNA techniques may result in the introduction of N- or C-terminal residues encoded by linkers introduced to facilitate cloning or other manipulation steps (e.g. as a result of insertion of a NotI restriction site, as described herein). Other manipulation steps include the introduction of linkers to join variable domains of the invention to further protein sequences. For example, an oligopeptide linker, as described above, may be introduced to join VH and VL regions in an scFv fragment. An antibody fragment of the invention may also be linked to a further protein sequence which is a dimerization domain as described herein. For example, it may be connected to a dimerization domain by a peptide or non-peptide linker as described herein, preferably a flexible linker. Any part of an antibody fragment may be connected to a dimerizing portion such as a dimerization domain. For example, a VH domain or a VL domain of an antibody fragment, such as an Fv antibody fragment, may be connected to the dimerization domain or a constant region of an antibody fragment, such as an Fab fragment, may be connected to the dimerization domain or a constant region of an antibody. Preferably, a dimerizing portion is connected to the C-terminal end of an antibody fragment. Dimerization domains are discussed further herein.

The present invention is concerned with undifferentiated pluripotent stem cells which express PODXL on their surface.

Preferably, an antibody molecule described herein binds PODXL (preferably human PODXL). For example, a monomeric antibody molecule of the invention may bind PODXL. Preferably, a dimeric or multimeric antibody molecule of the invention binds PODXL. Preferably, the VH and VL regions of an antibody fragment form an antigen binding site which binds PODXL.

An antibody molecule of the present invention will generally be specific for PODXL. In other words, an antibody molecule may bind PODXL with a greater affinity than other mammalian proteins, particularly other human proteins. For example, an antibody molecule may bind PODXL with a similar, or substantially similar affinity to that of mAb84. The kinetics of mAb84 binding to PODXL on the surface of hESCs have been determined as follows: $K_a$ (association rate) is $2.5 \times 10^7$ M; $K_D$ (dissociation rate) is $4 \times 10^{-8}$ M; $k_{off}$ is $2.9 \times 10^{-3}$ s$^{-1}$; $k_{on}$ is $7.1$ e4 M$^{-1}$ s$^{-1}$.

An antibody molecule may show no binding or substantially no binding to other mammalian proteins, and in particular to other proteins which are expressed on the cell surface. For example, an antibody molecule may show no binding or substantially no binding to any or all of the following: stage-specific embryonic antigens (SSEA)-3 and SSEA-4, tumor rejection antigen (Tra)-1-60 and Tra-1-81. Preferably, an antibody molecule of the invention binds PODXL on the surface of an undifferentiated pluripotent stem cell or cells, such as an undifferentiated hES cell and/or an undifferentiated induced pluripotent stem cell.

Typically, specificity may be determined by means of a binding assay such as ELISA employing a panel of antigens.

Binding of an antibody molecule described herein with PODXL may be abolished by competition with recombinant PODXL.

Binding affinity and neutralisation potency of different antibody molecules described herein can be compared under appropriate conditions using routine techniques.

Preferably, an antibody molecule of the invention binds specifically to undifferentiated pluripotent stem cell(s), e.g. the antibody molecule binds PODXL on the surface of undifferentiated pluripotent stem cell(s), such as undifferentiated hES cells and/or undifferentiated induced pluripotent stem cells. An antibody molecule may show no binding or substantially no binding to pluripotent stem cell(s) which have undergone, or are undergoing differentiation.

An antibody molecule according to the invention may also be one which competes for binding to PODXL with any antibody molecule which both binds PODXL and comprises a VH and VL domain, for example the VH and VL domain of mAb84. Thus, an antibody molecule of the present invention may compete with mAb84, and/or with scFv-84, or another antibody fragment based on mAb84, for binding to PODXL. Competition between antibody molecules may be assayed easily in vitro, for example using ELISA and/or by tagging a specific reporter molecule to one antibody molecule which can be detected in the presence of other untagged antibody molecule(s), to enable identification of antibody molecule(s) which bind the same epitope or an overlapping epitope.

Variants of the variable domain amino acid sequences disclosed herein may be employed, as discussed. Particular variants may include one or more amino acid sequence alterations (addition, deletion, substitution and/or insertion of an amino acid residue), may be less than about 20 alterations, less than about 15 alterations, less than about 10 alterations or less than about 5 alterations, 4, 3, 2 or 1. Alterations may be made in one or more framework regions and/or one or more CDRs, as described above.

Antibody molecules which bind PODXL may comprise variants of the VH and VL domains and CDRs described herein. Variants may be obtained by means of methods of sequence alteration or mutation and screening.

Thus, an antibody fragment may include a variant of one or more of the following CDR sequences:

(i) VL CDR1:
(SEQ ID NO: 2)
SASSSVNYMY;

(ii) VL CDR2:
(SEQ ID NO: 3)
DTSNLAS;

(iii) VL CDR3:
(SEQ ID NO: 4)
QQWSSYPYT;

(iv) VH CDR1:
(SEQ ID NO: 5)
NYWMN;

(v) VH CDR2:
(SEQ ID NO: 6)
EIRLKSNNYATHYAESVKG (vi) VH CDR3:
(SEQ ID NO: 7)
ERA.

Preferably, an antibody fragment having a variant of a CDR sequence as described herein (i.e. a variant of one or more of (i) to (vi)) binds or is capable of binding PODXL. Thus, an antibody molecule including such a fragment may bind or be capable of binding PODXL.

A variant of (vi) may be a variant in which one amino acid of (vi) is replaced with another amino acid. In other words, a variant may have about 66% or greater sequence identity with the entire length of SEQ ID NO: 7.

Furthermore, a variant may have one or more amino acids of one or more of the CDR sequences of SEQ ID NOs: 2 to 6 replaced by a different amino acid, or deleted.

A variant may be an amino acid sequence having at least about 70% sequence identity, at least about 75% sequence identity, at least about 80% sequence identity, at least about 85% sequence identity, or at least about 90% sequence identity with any one of SEQ ID NO:2, SEQ ID NO:3, SEQ ID NO:4, SEQ ID NO:5, and SEQ ID NO:6. Sequence identity may be calculated along the entire length of the given sequence, i.e. with the entire length of any of SEQ ID NOs: 2 to 6.

A variant may be one or more of the amino acid sequences of SEQ ID NOs: 2 to 6 in which no more than about 5%, no more than about 10%, no more than about 15%, no more than about 20%, no more than about 25%, or no more than about 30% of the amino acids differ from the amino acids of SEQ ID NO:2, SEQ ID NO:3, SEQ ID NO:4, SEQ ID NO:5, or SEQ ID NO:6, respectively.

An antibody fragment may have a variant of one or more of (i) to (v) in which one or two or three or more amino acids of one or more of (i) to (v) are replaced with another amino acid (i.e. substituted amino acids). An antibody fragment may, for example, have one or two or three amino acid substitutions in one or two or three or four or five of the sequences (i) to (v). For example, an antibody fragment may have one or two amino acid substitutions in one or two of the sequences (i) to (v).

Preferably, an antibody fragment having a variant of one or more of (i) to (v) has one or more of the following:

VL CDR1: SASSSVNYMY (SEQ ID NO: 2) or a variant thereof having up to 1, up to 2, up to 3, or up to 4 amino acid substitutions;

VL CDR2: DTSNLAS (SEQ ID NO: 3) or a variant thereof having up to 1, up to 2, or up to 3 amino acid substitutions;

VL CDR3: QQWSSYPYT (SEQ ID NO: 4) or a variant thereof having up to 1, up to 2, or up to 3 amino acid substitutions;

VH CDR1: NYWMN (SEQ ID NO: 5) or a variant thereof having up to 1, or up to 2 amino acid substitutions; and/or VH CDR2: EIRLKSNNYATHYAESVKG (SEQ ID NO: 6) or a variant thereof having up to 1, up to 2, up to 3, up to 4, up to 5, up to 6, or up to 7 amino acid substitutions.

In other words, an antibody fragment having a variant of one or more of (i) to (v) may have one or more of the following:

VL CDR1: SASSSVNYMY (SEQ ID NO: 2) or a variant having at least 9, at least 8, at least 7, or at least 6 amino acids thereof;

VL CDR2: DTSNLAS (SEQ ID NO: 3) or a variant having at least 6, at least 5, or at least 4 amino acids thereof;

VL CDR3: QQWSSYPYT (SEQ ID NO: 4) or a variant having at least 8, at least 7, or at least 6 amino acids thereof;

VH CDR1: NYWMN (SEQ ID NO: 5) or a variant having at least 4, or at least 3 amino acids thereof; and/or VH CDR2: EIRLKSNNYATHYAESVKG (SEQ ID NO: 6) or a variant having at least 18, at least 17, at least 16, or at least 15, at least 14, at least 13, or at least 12 amino acids thereof.

Preferably, an antibody fragment having a variant of one or more of (i) to (v) has one or more of the following:

VL CDR1: SASSSVNYMY (SEQ ID NO: 2) or a variant thereof having 70-100% sequence identity with SEQ ID NO:2;

VL CDR2: DTSNLAS (SEQ ID NO: 3) or a variant thereof having about 70-100% sequence identity with SEQ ID NO:3;

VL CDR3: QQWSSYPYT (SEQ ID NO: 4) or a variant thereof having about 66-100% sequence identity with SEQ ID NO:4;

VH CDR1: NYWMN (SEQ ID NO: 5) or a variant thereof having 80-100% sequence identity with SEQ ID NO:5; and/or VH CDR2: EIRLKSNNYATHYAESVKG (SEQ ID NO: 6) or a variant thereof having about 63-100% sequence identity with SEQ ID NO:6.

Sequence identity may be calculated along the entire length of the given sequence, i.e. with the entire length of any of SEQ ID NOs: 2 to 6. Sequence identity may be any of about 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% sequence identity.

An antibody molecule of the present invention includes a dimerizing portion. For example, a monomer (i.e. a monomeric antibody molecule) has a dimerizing portion and thus, each monomer which forms a dimeric or multimeric antibody molecule has a dimerizing portion. In some embodiments, an antibody molecule is a fusion of an Fv fragment, such as an scFv fragment, and a dimerizing portion. In some embodiments, an antibody molecule is a fusion of an Fv-containing fragment, such as an Fab fragment, and a dimerizing portion. Preferably a dimerizing portion is a polypeptide or comprises a polypeptide. An antibody fragment may be fused to a dimerization domain and/or a dimerizing portion via a linker. Furthermore, a dimerizing portion may or may not comprise a linker.

A dimerizing portion may be or may comprise a molecule (a first portion), for example a polypeptide or a polypeptide domain, which has an affinity for, interacts with and/or is capable of interacting with a second portion such that the two portions interact and/or associate to form a dimer. The second portion may be an identical or a similar portion. Preferably, the second portion is identical to the first portion.

Dimer and/or multimer interaction may be through covalent and/or non-covalent interactions. Interaction may be through any form of non-covalent interaction such as hydrogen bonding, van der Waals forces, ionic bonding or hydrophobic interactions. Alternatively, or in addition, a dimerizing portion may interact through covalent bonding, such as cross-linking. For example, a first monomer may be covalently bonded to a second monomer via one or more disulphide bonds. For example, a dimerizing portion may include a cysteine-containing polypeptide, for example a cysteine-containing tail, which is capable of forming one or more disulphide bonds with a second dimerizing portion.

A dimerizing portion may be a flexible dimerizing portion and/or may form or be capable of forming a flexible link between two monomers. For example, the dimerizing portions of a pair of monomers may interact to form a flexible link between the monomers. Alternatively or in addition, a pair of monomers may be flexibly linked by virtue of including a flexible linker which connects the antibody fragment to the dimerizing portion.

A dimerizing portion may comprise a dimerization domain. Furthermore, an antibody molecule may comprise a linker which connects an antibody fragment to a dimerization domain. For example, a dimerizing portion of an antibody molecule may have a linker and a dimerization domain. A linker may be a linker peptide or may be a non-peptide linker.

Non-peptide linkers include all linkage groups having two or more reactive groups except for a peptide linker. A non-peptide linker may be a non-peptide polymer linker. Preferably, the non-peptide linker is capable linking an antibody fragment to a dimerization domain as described herein. Preferably, a non-peptide polymer used as such a linker may has reactive groups at both ends, which individually bind to reactive groups of a polypeptide, for example, an amino terminus, a lysine residue, a histidine residue or a cysteine residue. Suitable reactive groups include an aldehyde group, a propionic aldehyde group, a butyl aldehyde group, a maleimide group, a ketone group, a vinyl sulfone group, a thiol group, a hydrazide group, a carbonyldimidazole (CDI) group, a nitrophenyl carbonate (NPC) group, a trysylate group, an isocyanate group, and succinimide derivatives. Examples of succinimide derivatives include succinimidyl propionate (SPA), succinimidyl butanoic acid (SBA), succinimidyl carboxymethylate (SCM), succinimidyl succinamide (SSA), succinimidyl succinate (SS), succinimidyl carbonate, and N-hydroxy succinimide (NHS). The reactive groups at both ends of the non-peptide polymer may be the same or different. For example, the non-peptide polymer may have a maleimide group at one end and an aldehyde group at another end.

A non-peptide polymer may be a biocompatible polymer including two or more repeating units linked to each other. Examples of non-peptide polymers include polyethylene glycol (PEG), polypropylene glycol (PPG), co-poly(ethylene/propylene) glycol, polyoxyethylene (POE), polyurethane, polyphosphazene, polysaccharides, dextran, polyvinyl alcohol, polyvinylpyrrolidones, polyvinyl ethyl ether, polyacrylamide, polyacrylate, polycyanoacrylates, lipid polymers, chitins, hyaluronic acid, and heparin.

A linker peptide may be a peptide of 1 to 100 or more amino acids. Preferably, a linker peptide may have 1 or more amino acids, 2 or more, 3 or more, 4 or more, 5 or more, 6 or more, 7 or more, 8 or more, 9 or more, 10 or more, 11 or more, 12 or more, 13 or more, 14 or more, 15 or more amino acids. A linker peptide may have 100 or fewer amino acids, 90 or fewer, 80 or fewer, 70 or fewer, 60 or fewer, 50 or fewer, 40 or fewer, 30 or fewer, 25 or fewer, 20 or fewer, or 15 or fewer amino acids. Preferably, a linker peptide is from 1 to about 20 amino acids in length, more preferably from about 5 to 15 amino acids in length, more preferably from about 8 to 12 amino acids in length. For example, a linker peptide may be about 10 amino acids in length.

Preferably, a linker is a flexible linker, i.e. it provides a flexible link between an scFv fragment and a dimerization domain. A flexible linker peptide may be an immunoglobulin hinge region and/or may be derived from or based on the hinge region of any immunoglobulin isotype. For example, a linker may be a polypeptide comprising an amino acid sequence that shares sequence identity, or similarity, with a portion of a naturally-occurring Ig hinge region sequence. In some preferred embodiments, a linker peptide is an IgG hinge region, for example an IgG3 upper hinge as set out, or substantially as set out in SEQ ID NO: 10. Alternatively, a peptide linker may be a flexible linker which is not, or is not similar to, an IgG hinge region or an immunoglobulin hinge region in general.

A dimerization domain may be any synthetic or naturally occurring polypeptide or polypeptide domain which is capable of interacting with a second dimerization domain.

An antibody molecule may be a recombinant antibody molecule. In some embodiments, an antibody fragment is connected to a heterologous dimerizing portion and/or dimerization domain.

By "heterologous" is that a polypeptide originates from a foreign source or, if from the same source is modified from its naturally occurring form. Thus, a heterologous portion or domain is a portion or domain which is not naturally fused to or connected to the antibody fragment.

Preferably, a dimerization domain is a self-associating primary or secondary structure. For example, a dimerization domain may include a helix, e.g. an α-helix. For example, a first helix may associate with a second helix to form a helix bundle and four helices may associate to form a four helix bundle. Accordingly, dimerization and/or multimerization (e.g. tetramerization) may be driven by helix-helix interactions. A first helix may or may not be identical to a second helix. A self-associating helix may, for example, have the sequence GELEELLKHLKELLKG (SEQ ID NO: 21).

In one embodiment, a dimerization domain is a helix-turn-helix (HTH) motif. In the context of the present disclosure, a HTH motif is a polypeptide structural motif having a first helix and a second helix, separated by a short loop which is capable of dimerizing with a second HTH motif. In nature, HTH motifs are typically involved in binding DNA, however, a HTH motif of the present invention may or may not be capable of binding DNA.

A dimerizing portion may have a dimerization domain which is not an HTH motif. Other dimerization domains may be selected from: a coiled-coil motif, a leucine zipper motif, an ef-hand motif or a p53 oligomerization domain. For example, a leucine zipper may be a GCN4 leucine zipper motif, or may be a JUN or a FOS leucine zipper. For example, a JUN leucine zipper motif of one monomer may interact with a FOS leucine zipper motif of a second monomer.

Alternatively, or in addition, a dimerizing portion may include a cysteine-containing peptide. A cysteine-containing peptide may, for example, form one or more disulphide bonds with another cysteine-containing peptide in a dimerizing portion, for example in a second monomer. A cysteine-containing peptide may include a CPP motif, for example a $(CPP)_3$ motif. A cysteine-containing peptide may include a sequence as set out, or substantially as set out in SEQ ID NO: 25.

A variety of suitable self-associating dimerization domains are known to the skilled person, see for example PlUckthun (1997), incorporated herein by reference.

An antibody molecule including two monomers is preferably smaller than a whole antibody, such as a typical IgG antibody. As mentioned above, such antibody molecules and fragments may penetrate better into cell-clumps or tissues. For example an antibody molecule may be of less than 150 kDa. An antibody molecule may be of about 140 kDa or less, 130 kDa or less, 120 kDa or less, 110 kDa or less, 100 kDa or less, 90 kDa or less, 80 kDa or less, 70 kDa or less, 60 kDa or less, or 50 kDa or less. In some embodiments, the antibody molecule is of about 70 kDa or less, 69 kDa or less, 68 kDa or less, 67 kDa or less, 66 kDa or less, 65 kDa or less, 64 kDa or less, 63 kDa or less, 62 kDa or less, or 61 kDa or less.

Accordingly, an antibody molecule, for example a monomeric antibody molecule, may be of about 90 kDa or less. A monomeric antibody molecule may be of 80 kDa or less, 70 kDa or less, 60 kDa or less, 50 kDa or less, 40 kDa or less, or 30 kDa or less. In some embodiments, a monomeric antibody molecule may be of about 35 kDa or less, 34 kDa or less, 33 kDa or less, 32 kDa or less, 31 kDa or less, or 30 kDa or less.

The size of an antibody molecule may be expressed in units of molecular weight (also referred to as molecular mass), for example as kDa (kilodaltons), as above. A molecular weight referred to herein may be an absolute molecular weight or may be an apparent molecular weight. The molecular weight of a macromolecule such as a protein or polypeptide of unknown mass may be determined by sodium dodecyl sulfate (SDS)-polyacrylamide gel electrophoresis (PAGE) under reducing or nonreducing conditions by comparing the electrophoretic mobilities of the unknown protein or polypeptide to known proteins (molecular weight standards). This may be combined with detection methods such as Western blotting. Similarly, molecular weight can also be determined by size exclusion chromatography by comparing the elution time of an unknown protein or polypeptide to known standards. Preferably, the molecular weight is the apparent molecular weight. Methods for determining the dimeric or multimeric nature of a polypeptide such as an antibody molecule are familiar to the person skilled in the art and may include methods such as electrophoresis, immunoblot and/or size exclusion chromatography as described herein.

An antibody molecule of the invention which includes two monomers, as described herein, may be referred to as a miniantibody. For example, an antibody molecule may be a miniantibody which comprises a first monomer joined to a second monomer via interacting dimerizing portions. A miniantibody, as described herein, is a bivalent or multivalent antibody molecule which is smaller than a whole antibody.

For example, a miniantibody may be an antibody molecule which binds PODXL and includes two monomers, each monomer including an antibody fragment connected to a dimerizing portion, wherein the dimerizing portions interact to form the antibody molecule. Preferably, in a miniantibody as described herein, each antibody fragment is connected to a dimerizing portion via a flexible linker.

A miniantibody may be recombinant. In some preferred embodiments, an antibody fragment of a miniantibody is connected to a heterologous dimerizing portion and/or dimerization domain.

Antibody molecules and nucleic acid encoding antibody molecules will generally be isolated i.e. free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo.

Antibody molecules and nucleic acid may be formulated with diluents or adjuvants and still for practical purposes be isolated—for example the molecules will normally be mixed with gelatin or other carriers if used to coat microtitre plates for use in immunoassays, or will be mixed with pharmaceutically acceptable carriers or diluents when used in diagnosis or therapy. Antibody molecules may be glycosylated, either naturally or by systems of heterologous eukaryotic cells (e.g. CHO or NS0 (ECACC 85110503) cells), or they may be (for example if produced by expression in a prokaryotic cell) unglycosylated.

In addition to an antibody fragment and a dimerizing portion, an antibody molecule as described herein may comprise other amino acids, e.g. forming a peptide or polypeptide, such as a folded domain, or to impart to the molecule another functional characteristic in addition to ability to bind antigen.

In some embodiments, antibody molecules may carry a detectable or functional label, or may be conjugated to a toxin or enzyme (e.g. via a peptidyl bond or linker).

A label can be any molecule that produces or can be induced to produce a signal, including but not limited to fluorescers, radiolabels, enzymes, chemiluminescers or photosensitizers. Thus, binding may be detected and/or measured by detecting fluorescence or luminescence, radioactivity, enzyme activity or light absorbance.

Suitable labels include radiolabels such as 131I or 99Tc, which may be attached to antibody molecules using conventional chemistry known in the art of antibody imaging. Labels also include enzyme labels such as horseradish peroxidase, alkaline phosphatase, glucose-6-phosphate dehydrogenase ("G6PDH"), alpha-D-galactosidase, glucose oxydase, glucose amylase, carbonic anhydrase and acetylcholinesterase. Labels include fluorescent labels or fluorescers, such as fluorescein and its derivatives, fluorochrome, rhodamine compounds and derivatives and GFP (GFP for "Green Fluorescent Protein"). Labels further include chemical moieties such as biotin which may be detected via binding to a specific cognate detectable moiety, e.g. labelled avidin.

Where the additional feature is a polypeptide domain or label, the antibody molecule may be produced by recombinant techniques which are familiar to the person skilled in the art, i.e. by the expression of nucleic acid encoding a fusion of the antibody molecule and the further domain.

Nucleic Acids

Isolated nucleic acids are provided which comprise a nucleotide sequence encoding an antibody molecule as described herein. For example, an isolated nucleic acid may comprise a nucleotide sequence encoding a monomer (monomeric antibody molecule) as described herein.

In further aspects, the present disclosure provides an isolated nucleic acid which comprises a nucleotide sequence encoding an antibody molecule, a VH domain, or a VL domain as described above, for example a VH or VL domain of SEQ ID NO: 8 or 9 respectively, and methods of preparing an antibody molecule, a VH domain, or a VL domain as described above, which comprise expressing said nucleic acid under conditions to bring about production of said antibody molecule, VH domain, or VL domain, and recovering it.

Also provided are nucleic acids, generally isolated, which encode a VH CDR or VL CDR sequence described herein, especially a VH CDR selected from SEQ ID NOs: 5, 6 and 7, and/or a VL CDR selected from SEQ ID NOs: 2, 3 and 4, or variants thereof. Most preferably nucleic acids of the invention encode mAb84 VH CDR3 (SEQ ID NO. 7).

The nucleic acids of the invention may comprise the sequences, or relevant portions thereof (e.g. CDR-encoding regions) of SEQ ID NO:13, SEQ ID NO:14 or SEQ ID NO:15, or variants of these sequences modified by, for example, site-directed mutagenesis to encode other, variant, VH and VL domains of the invention. Nucleic acids of the invention, particularly nucleic acids encoding an scFv fragment, may further include a nucleotide sequence encoding a glycine-serine linker, for example the nucleotide sequence of SEQ ID NO: 18, or a variant thereof. Nucleic acids of the invention, particularly nucleic acids encoding an Fab fragment, may further include a nucleotide sequence encoding a CH1 domain, for example the nucleotide sequence of SEQ ID NO: 28, or a variant thereof, and may further include a nucleotide sequence encoding a CL domain, for example, the nucleotide sequence of SEQ ID NO: 30, or a variant thereof. Nucleic acids of the invention may further include a nucleotide sequence encoding an immunoglobulin hinge region, for example the nucleotide sequence of SEQ ID NO: 16, or a variant thereof. Nucleic acids of the invention may further include a nucleotide sequence encoding a dimerization domain, for example the nucleotide sequence of SEQ ID NO: 17 encoding an HTH motif, or a variant thereof, or the nucleotide sequence of SEQ ID NO: 25 encoding a $CPP_3$ motif, or a variant thereof.

Codon usage may be varied, e.g. to optimize expression of the sequence in a desired host cell. A nucleic acid encoding an antibody molecule of the invention may or may not include a nucleotide sequence encoding a His-tag, for example the nucleotide sequence of SEQ ID NO: 29.

Another aspect of the present invention provides an isolated nucleic acid encoding an antibody molecule of the present invention. In preferred aspects, the present invention provides a nucleic acid which encodes a CDR or a VH or VL domain of the invention as defined herein. In further preferred aspects a nucleic acid encodes a linker peptide, e.g. an immunoglobulin hinge region, and/or a polypeptide dimerization domain, e.g. an HTH motif as described herein.

Nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Aspects of the present invention also provide vectors, for example in the form of plasmids, viruses, e.g. 'phage, or phagemid, cosmids, transcription or expression cassettes which comprise at least one nucleic acid as above.

Suitable vectors can be chosen or constructed, containing appropriate regulatory sequences, including promoter sequences, terminator sequences, polyadenylation sequences, enhancer sequences, marker genes and other sequences as appropriate. For further details see, for example, Molecular Cloning: a Laboratory Manual: 2nd edition, Sambrook et al., 1989, Cold Spring Harbor Laboratory Press.

Vectors also include viral vectors capable of infecting mammalian cells in vivo, e.g. adenoviral, retroviral or adeno-associated virus vectors. Such vectors may be useful for expression of an antibody molecule of the invention in the cells of a human or other mammalian subject, to provide for production and delivery of the antibody molecule to said subject. Such vectors may be referred to as expression vectors.

A nucleic acid sequence encoding an antibody molecule of the invention will in one aspect be operably linked to a promoter to effect expression of the antibody molecule in a host cell. The sequence may include at its 5' end a leader sequence to facilitate expression and/or secretion of the antibody molecule in and/or from a host cell. Numerous suitable leader sequences are known as such in the art and may be selected by a person of ordinary skill in the art taking account of the host cell.

Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds. John Wiley & Sons, 1992. The disclosures of Sambrook et al. and Ausubel et al. are incorporated herein by reference.

Another aspect provides a host cell transformed with a nucleic acid (e.g. a nucleic acid sequence in the form of a vector) of the invention.

Nucleic acid may be integrated into the genome (e.g. chromosome) of the host cell. Integration may be promoted by inclusion of sequences which promote recombination with the genome, in accordance with standard techniques.

Another aspect provides a method of production of an antibody molecule as described herein, the method including causing expression from encoding nucleic acid. Such a method may comprise culturing host cells under conditions for production of said antibody molecule.

Following production by expression, an antibody molecule may be isolated and/or purified using any suitable technique, then used as appropriate. A method of production may comprise a step of isolation and/or purification of the product. Multimeric antibody molecules may be produced by providing a plurality of antibody molecules which are monomers under conditions permitting multimerization, e.g. dimerization, of said antibody molecules. Accordingly, a method of producing an antibody molecule described herein may include producing a plurality of antibody molecules which are monomers by expression, as described herein, and allowing said monomers to dimerize, and even to multimerize. Monomers produced by methods described herein may spontaneously dimerize once they are produced. For example, monomers may dimerize within a host cell following production by expression, and/or may dimerize under conditions permitting dimerization in vitro.

Following purification of the product the antibody molecule may be modified by physical or chemical means, for example to introduce protective groups that alter, e.g. increase, the stability or biological half-life of the protein. For example, PEGylation of proteins to achieve such effects is known as such in the art and antibody molecules of the invention may be in PEGylated form.

A method of production may comprise formulating the product into a composition including at least one additional component, such as a pharmaceutically acceptable excipient.

The present invention also provides a recombinant host cell which comprises one or more nucleic acids or vectors as above.

Systems for cloning and expression of an antibody molecule in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NS0 mouse melanoma cells, YB2/0 rat myeloma cells and many others. A common, preferred bacterial host is *E. coli*.

The expression of antibodies and antibody fragments in prokaryotic cells such as *E. coli* is well established in the art. For a review, see for example Plückthun, A. Bio/Technology 9: 545-551 (1991). Expression in eukaryotic cells in culture is also available to those skilled in the art as an option for production of an antibody molecule, see for recent reviews, for example Ref, M. E. (1993) Curr. Opinion Biotech. 4: 573-576; Trill J. J. et al. (1995) Curr. Opinion Biotech 6: 553-560.

Methods

The present disclosure provides antibody molecules based on fragments of mAb84 which are effective at binding PODXL on the surface of undifferentiated pluripotent stem cells and which may be cytotoxic to such cells. Methods according to the present invention preferably involve binding of an antibody molecule which binds PODXL to cells that express PODXL on their surface, preferably undifferentiated pluripotent stem cells and preferably not differentiated pluripotent stem cells. Differentiated pluripotent stem cells may include pluripotent stem cells which have undergone or are undergoing differentiation.

Antibody molecules of the invention may be used in methods which take advantage of their binding to PODXL and may further take advantage of their cytotoxic properties. Accordingly, methods of binding may be useful for identifying, isolating, separating, purifying, enriching or removing undifferentiated pluripotent stem cells from a sample and/or for identifying, isolating, separating, purifying, or enriching differentiated pluripotent stem cells.

Methods according to the present invention may comprise:
  (a) identifying undifferentiated pluripotent stem cells;
  (b) isolating undifferentiated or differentiated pluripotent stem cells;
  (c) separating undifferentiated pluripotent stem cells from other cells, e.g. from differentiated pluripotent stem cells;
  (d) enriching undifferentiated or differentiated pluripotent stem cells;
  (e) preparing a composition of differentiated pluripotent stem cells having substantially no undifferentiated pluripotent stem cells; or
  (f) preparing a composition of undifferentiated pluripotent stem cells having substantially no differentiated pluripotent stem cells.

Methods according to the present invention may involve the step of contacting a sample with an antibody molecule which is capable of binding to PODXL (a PODXL binding moiety or an anti-PODXL antibody molecule). This may be under conditions suitable to permit binding of the antibody molecule to PODXL. For example, it may be under conditions suitable to permit binding of the antibody molecule to an undifferentiated pluripotent stem cell via PODXL on the cell's surface. Such conditions are well known to those of ordinary skill in the art, for example comprising physiological pH and physiological buffer. Preferably the antibody molecule is an antibody molecule including two monomers, as described herein, although antibody molecules of the invention which are monomers (monomeric antibody molecules) may bind PODXL and thus may also be used in methods of binding, identifying, isolating and separating undifferentiated pluripotent stem cells.

The sample may be contacted with the PODXL-binding antibody molecule for a sufficient time to allow the antibody molecule to bind to PODXL. Sufficient time may, for example, be 5 minutes, 10 minutes, 30 minutes, 45 minutes, 60 minutes, 90 minutes or longer than 2 hours.

In preferred embodiments, methods according to the present invention comprise contacting the sample with antibody molecule, allowing the antibody molecule to bind to PODXL on the surface of the cell and determining which cells have the PODXL antibody molecule bound thereto.

Methods according to the present invention may comprise the step of identifying cells bound by an antibody molecule. Methods according to the present invention may comprise the step of isolating cells bound by an antibody molecule. Methods according to the present invention may comprise the step of partitioning, removing, separating or purifying cells bound by an antibody molecule. Methods according to the present invention may comprise the step of destroying cells bound by an antibody molecule. Methods according to the present invention may further comprise the step of quantifying cells that have been identified, isolated, separated, partitioned, enriched, bound or removed.

The methods of identifying undifferentiated pluripotent stem cells disclosed herein are useful for imaging undifferentiated pluripotent stem cells, particularly where the cells are tagged with a detectable label, and for characterizing pluripotent stem cells.

Methods involving binding an antibody molecule to PODXL expressed on the surface of undifferentiated pluripotent stem cells are useful for research into, and the clinical development of, pluripotent stem cells.

An antibody molecule bound to PODXL expressed on the surface of a cell forms a complex of antibody molecule and PODXL. The cell expressing the PODXL to which the antibody molecule is bound forms part of the complex.

Methods may comprise the step of detecting the complexes, e.g. by detecting the presence of the antibody molecule or by detecting a detectable label coupled to the antibody molecule.

Some methods of the present invention comprise the step of partitioning those complexes from the sample or from other non-complexed cells in the sample, and may further comprise the step of detecting the complexes, e.g. by detecting the presence of the antibody molecule or a detectable label coupled to the antibody molecule.

Some methods of the present invention comprise the step of contacting the sample with an antibody molecule for sufficient time to allow formation of a complex of antibody molecule and PODXL, and removing complexed cells from the sample. Such methods are useful in isolation and/or purification of differentiated and/or undifferentiated pluripotent stem cells.

In methods of the present invention the antibody molecule may be immobilised on, e.g. conjugated to, a solid support so that the pluripotent stem cells can be bound by affinity binding. Conveniently, the solid support comprises any suitable matrix such as agarose, acrylamide, Sepharose™ and Sephadex™. The solid support may be a solid substrate such as a microtitre plate or chip, or a column.

In some embodiments the antibody molecule is magnetically labelled (either directly or indirectly) such that, when bound, the pluripotent stem cell can be separated from the rest of the sample upon provision of a suitable magnetic field. Microbeads used for magnetic cell sorting are often termed MACS colloidal super paramagnetic microbeads. Pluripotent stem cells labelled in this way may be sorted by magnetic activated cell sorting (MACS).

Other methods of separating cells which comprise a specific cellular marker are known in the art and include FACS (Fluorescence Activated Cell Sorting) for which the binding moiety is labelled with a fluorescent molecule.

Methods according to the present invention may comprise the step of culturing the undifferentiated or differentiated pluripotent stem cells which have been bound, identified, isolated, separated, enriched or removed. The methods may also comprise the step of differentiating undifferentiated pluripotent stem cells so obtained.

Methods according to the present invention may be used to provide an enriched or substantially isolated composition of differentiated or undifferentiated pluripotent stem cells. Such a composition may be used in various ways, for example it may be used in cell therapy or it may be used as a source of cells which are then encouraged to differentiate into a particular cell lineage which is useful for a particular therapy, or it may be used to investigate (in vitro or in vivo) the factors which allow for the cell to differentiate into other cells.

Typically, the enriched composition of pluripotent embryonic stem cells contains at least 50% of the cells as either differentiated or undifferentiated pluripotent stem cells, preferably at least 70% or at least 90% or at least 95%. Preferably, all, or substantially all of the cells in the composition are the said differentiated or undifferentiated pluripotent stem cells.

Methods for enriching a population of cells preferably involve increasing the concentration of the cells in the sample or increasing the population of cells (i.e. number of cells of a given type), either absolutely or relative to the number of other cells in the sample.

The invention also provides methods of destroying an undifferentiated induced pluripotent stem cell, the method comprising destroying the cell or cells in the sample that express PODXL on their surface. An undifferentiated pluripotent stem cell may be destroyed by virtue of being bound to an antibody molecule of the invention, particularly a dimeric antibody molecule. In some embodiments a sample of cells is contacted with an antibody molecule for sufficient time to allow the antibody molecule to bind to those cells expressing PODXL on their surface. The antibody molecule may comprise a cytotoxic agent capable of destroying the cell to which it has bound. Alternatively, the cell may be destroyed by the antibody molecule itself, or because of the attachment of the antibody molecule. Alternatively, the cell may be destroyed by the interaction of the antibody molecule with a cytotoxic agent. Accordingly, the method may comprise addition of a cytotoxic agent capable of interacting with the antibody molecule so as to destroy cells bound to the binding moiety.

In some methods, the antibody molecule mediates cell death by an oncosis mechanism, which is a form of cell death resulting from membrane damage leading to an increase in cell permeability (as evidenced by permeability to dyes such as propidium iodide/trypan blue) and cell shrinkage. Cell death induced by the methods of the invention may be preceded by poration of the cell membrane, blebbing and/or cell clumping. In some embodiments of a method of destroying an undifferentiated pluripotent stem cell, the antibody molecule capable of binding to PODXL may be dimeric scFv84-HTH.

Suitable cytotoxic moieties, which can be linked to an antibody molecule, include radioactive atoms, cytotoxic drugs, cytotoxic proteins and enzyme systems that convert a prodrug into a cytotoxic drug. These are well known in the art.

In a preferred embodiment, the invention includes a method of destroying an undifferentiated pluripotent stem cell in a sample containing such cells, the method comprising the steps of contacting the sample with an antibody molecule which is toxic to the said cell, such as a dimeric antibody molecule as described herein, allowing the antibody molecule to bind to the PODXL on the surface of the said cell and allowing the antibody molecule to kill the said cell. The antibody molecule may itself be cytotoxic to the said cell or may include a further moiety which is toxic to the cell.

In some embodiments the antibody molecule is administered to the sample or cells simultaneously or sequentially with a cytotoxic agent. The antibody molecule may be administered in conjunction with one or more other agents that are capable of binding to other stem cell associated molecules in order to ensure complete removal of residual undifferentiated pluripotent stem cells.

Methods for destroying undifferentiated pluripotent stem cells may be used to remove undifferentiated cells from a population of pluripotent stem cells that have been induced to differentiate. Methods for destroying undifferentiated pluripotent stem cells may be used prior to transplantation of tissues or organs to eliminate residual pluripotent stem cells, thus increasing the success and safety of the graft, particularly by reducing the risk of teratoma formation.

The invention provides an isolated undifferentiated pluripotent stem cell(s) or an isolated differentiated pluripotent stem cell(s) which is obtained by a method described herein.

The invention also provides methods of generating and identifying reprogrammed induced pluripotent stem cells from a sample. This enables the selection of successfully reprogrammed induced pluripotent stem cells from cells which have not been successfully reprogrammed.

Such a method comprises inducing non-pluripotent donor cells into a pluripotent state to generate induced pluripotent stem cells expressing PODXL on their surface, contacting the induced pluripotent stem cells with an antibody molecule capable of binding PODXL under conditions permitting the binding of the antibody molecule to PODXL expressed on the surface of the induced pluripotent stem cells; and identifying cells bound by the antibody molecule.

Techniques for the induction of non-pluripotent donor cells into a pluripotent state are known in the art. For example, those reported by Takahashi et al ((2007) Induction of Pluripotent Stem Cells from Adult Human Fibroblasts by Defined Factors. Cell 131(5):861-72) and Yu et al ((2007) Induced Pluripotent Stem Cell Lines Derived from Human Somatic Cells. Science 318(5858):1917-20), both incorporated herein by reference.

Such techniques include transfection of donor cells with stem cell associated genes and/or transcription factors using viral vectors. Such genes and factors may include one or more of Oct-3/4 (Pouf51) Sox2, c-Myc, Klf4, Nonaog and LIN28, as explained below under "Induced Pluripotent Stem Cells".

Donor cells may comprise adult somatic cells, e.g. fibroblasts, as described below under "Induced Pluripotent Stem Cells".

Methods according to the present invention are preferably performed in vitro. The term "in vitro" is intended to encompass experiments with cells in culture whereas the term "in vivo" is intended to encompass experiments with intact multicellular organisms.

Sequence Identity

Percentage (%) sequence identity is defined as the percentage of amino acid residues in a candidate sequence that are identical with residues in the given listed sequence (referred to by the SEQ ID NO) after aligning the sequences and introducing gaps if necessary, to achieve the maximum sequence identity, and not considering any conservative substitutions as part of the sequence identity. Sequence identity may be calculated over the entire length of the respective sequences.

Alignment for purposes of determining percent amino acid sequence identity can be achieved in various ways known to a person of skill in the art, for instance, using publicly available computer software such as ClustalW 1.82. T-coffee or Megalign (DNASTAR) software. When using such software, the default parameters, e.g. for gap penalty and extension penalty, are preferably used. The default parameters of ClustaiW 1.82 are: Protein Gap Open Penalty=10.0, Protein Gap Extension Penalty=0.2, Protein matrix=Gonnet, Protein/DNA ENDGAP=−1, Protein/DNA GAPDIST=4.

Identity of nucleic acid sequences may be determined in a similar manner involving aligning the sequences and introducing gaps if necessary, to achieve the maximum sequence identity, and calculating sequence identity over the entire length of the respective sequences.

An antibody molecule described herein may include an amino acid sequence, for example a CDR sequence or a variable domain sequence, which is a variant of a given amino acid sequence. Sequence identity of such variants may be determined over the entire length of the given sequence. For example, the sequence identity of a variant amino acid sequence may be determined by aligning the variant amino acid sequence with the given sequence without introducing gaps in the given sequence.

An amino acid sequence, for example a CDR amino acid sequence or a variable domain amino acid sequence, may have a sequence identity of at least about 70%, at least about 75% sequence identity, at least about 80% sequence identity, at least about 85% sequence identity, or at least about 90% sequence identity with a given sequence. For example, this identity may be any of about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% sequence identity. A given sequence may be a CDR sequence, for example a CDR sequence as set out in SEQ ID NO:2, SEQ ID NO:3, SEQ ID NO:4, SEQ ID NO:5, or SEQ ID NO:6, or may be a variable region sequence, for example a VH domain sequence as set out in SEQ ID NO: 9 or a VL region sequence as set out in SEQ ID NO: 8. An antibody molecule of the invention may, for example, include an amino acid sequence having sequence identity to such a given sequence.

Sample

Some methods of the present invention involve a sample containing cells. For example a sample may include a population of cells. The sample may be any quantity of cells which contains, or is suspected of containing, one or more undifferentiated pluripotent stem cells. The sample may be a culture of cells grown in vitro. For example, the culture may comprise a suspension of cells or cells cultured in a culture plate or dish.

In preferred embodiments the sample contains undifferentiated pluripotent stem cells, for example, undifferentiated human pluripotent stem cells such as human embryonic stem cells and/or induced pluripotent stem cells. A sample may also contain non-pluripotent cells. In some embodiments the sample contains undifferentiated pluripotent stem cells and pluripotent stem cells that have undergone differentiation or are undergoing differentiation. Pluripotent stem cells that have undergone differentiation or are undergoing differentiation may no longer be pluripotent and preferably do not express PODXL on their surface.

The sample may be one in which undifferentiated pluripotent stem cells have been encouraged (or promoted) to differentiate into particular cell lineages and therefore the sample may contain a mixture of undifferentiated and differentiated cells (because differentiation is often not an efficient process). Typically in such a sample the undifferentiated pluripotent stem cells constitute a few percent of the total number of cells. Typically, the differentiated cells in the sample may be cardiomyocytes, pancreatic islets, neuronal progenitor cells or mesenchymal stem cells which are derived (by differentiation) from the pluripotent stem cells. Removal (or destruction) of the undifferentiated pluripotent stem cells from (or in) such a sample will be useful prior to the clinical application of the sample which contains differentiated cells because, potentially, the undifferentiated cells can form undesirable teratomas. Typically, at least 95% of the undifferentiated pluripotent stem cells are removed or destroyed. Preferably, all of the said cells are removed or destroyed.

In some embodiments the sample does not contain non-induced pluripotent cells, e.g. embryonic stem cells (ESCs). In some embodiments the sample does not contain embryonic stem cells or non-induced pluripotent cells. In some embodiments, the sample does not contain induced pluripotent stem cells.

The sample may contain undifferentiated pluripotent stem cells expressing PODXL on their surface. In some instances, the sample may include undifferentiated induced pluripotent stem cells which have been derived from somatic cells that have been induced to pluripotency. In other instances, the sample may comprise IPSCs that have been induced to differentiate into other cells. The sample may contain other non-pluripotent cells, e.g. feeder cells or fibroblasts.

Podocalyxin-Like Protein (PODXL)

The amino acid sequence of Podocalyxin-like protein 1 precursor herein referred to as Podocalyxin-like protein (PODXL) is found in Accession No. 000592 of the NCBI protein sequence database accessible through EntrezPubMed (see also Kershaw et al (1997) J. Biol. Chem. 272, 15708-15714). It is also called PCLPI and PODXL. For convenience, it will be called PODXL hereafter. PODXL may have the precise sequence given in Accession No. O00592, or it may be a naturally occurring variant thereof. For example, according to O00592, R is a variant for the T at residue 62, and S is a variant of the L at residue 196.

Mature PODXL is a 528 residue glycosylated cell surface polypeptide, of which residues 1-22 are a signal peptide, and residues 23-528 represent the mature protein. Residues 23-431 are believed to be the extracellular portion of the protein and residues 432-452 are the transmembrane region. Residues 23-304 represent a Ser/Thr rich region. It is preferred if the antibody molecule which binds to PODXL binds to the extracellular region of PODXL, for example within the Ser/Thr rich region, or outside of this region.

Podocalyxin-like protein is a member of the sialomucin protein family. PODXL was originally identified as an important component of glomerular podocytes. Podocytes are highly differentiated epithelial cells with interdigitating foot processes covering the outer aspect of the glomerular basement membrane. Other biological activities of PODXL include binding in a membrane protein complex with Na+/H+ exchanger regulatory factor to intracellular cytoskeletal elements, playing a role in hematopoetic cell differentiation, and being expressed in vascular endothelium cells and binding to L-selectin.

PODXL is a heavily glycosylated type-I transmembrane protein belonging to the CD34 family of sialomucins. PODXL was originally described as the major sialoprotein on podocytes of the kidney glomerulus, but was later found to be expressed on vascular endothelial cells and early hematopoietic progenitors. More recently, PODXL has been implicated as an indicator of tumor aggressiveness in breast, liver, and prostate cancers. Human PODXL is located on chromosome 7q32-q33 and encodes for a protein of 528 amino acids. However, because the extracellular domain of PODXL is extensively glycosylated with sialylated O-linked carbohydrates and five potential sites for N-linked glycosylation, the approximate molecular weight of PODXL is 160-165 kDa.

Functionally, PODXL has been reported to have quite diverse roles depending on the cell type. In podocytes, PODXL acts as an anti-adhesion molecule that maintains the filtration slits open between podocyte foot processes by charge repulsion. However in high endothelial venules, PODXL acts as an adhesion molecule binding to L-selectin and mediating the tethering and rolling of lymphocytes.

In hESC, PODXL was identified transcriptionally to be highly expressed in undifferentiated hESC[5, 6]. By expressed sequence tag frequency analysis, the level of PODXL expression was down-regulated by almost 2.5-fold in 7-8 day embyroid bodies and approximately 7 and 12 fold in neuroectoderm-like cells and hepatocyte-like cells respectively[5]. This result was supported by immunohistochemistry of hESC and 8-day EB where staining was significantly reduced in the latter[7]. In a separate study by Wei et al. comparing the transcriptome profile of hESC and mESC, they observed that the expression of PODXL was not detected by MPSS in mESC line E-14 compared to hESC[8]. At the protein level, Schopperle and DeWolf[9] reported that PODXL underwent post-translational glycosylation changes after the exposure of 2 embryonal carcinoma lines to retinoic acid (reduction in MW from 200 kDa to 170 kDa). The failure of anti-TRA-1-60/81 antibodies to bind to the modified PODXL prompted them to suggest the presence of a Stem Cell PODXL (SC-PODXL) on embryonic stem cells. In ESC, our observations have shown that mAb 84 binding reactivity was reduced in day 8 embyroid bodies compared to undifferentiated hESC. Concomitantly, the decrease or loss in mAb 84-mediated killing on FGF2-starved hESC and day 22 EB respectively can be attributed to the down-regulation of PODXL expression upon differentiation. Furthermore, the simultaneous decrease in mAb 84 and TRA-1-60 binding to hESC during embryoid body formation may implicate the loss of SC-PODXL during differentiation.

In preferred methods of the invention, the PODXL is human PODXL. Human PODXL may have the amino acid sequence of GenBank accession number 000592.2 GI:229462740 or of GenBank accession number AAI43319.1 GI:219520307.

In some embodiments, the PODXL protein comprises one of 60%, 70%, 80%, 85%, 90%, 95%, 96%, 97%, 98%, 99% or 100% sequence identity to the amino acid sequence of GenBank accession number 000592.2 GI:229462740 or of GenBank accession number AAI43319.1 GI:219520307. Preferred PODXL proteins are those capable of being bound by an antibody fragment or antibody molecule as described herein, and/or by mAb84.

Stem Cells

The term "stem cell" generally refers to a cell that on division faces two developmental options: the daughter cells can be identical to the original cell (self-renewal) or they may be the progenitors of more specialised cell types (differentiation). The stem cell is therefore capable of adopting one or other pathway (a further pathway exists in which one of each cell type can be formed). Stem cells are therefore cells which are not terminally differentiated and are able to produce cells of other types.

As used in this document the term "stem cell" particularly refers to pluripotent stem cells, particularly mammalian (e.g. human) pluripotent stem cells.

Embryonic Stem Cells

Embryonic Stem (ESCs) cells may be isolated from the inner cell mass (ICM) of the blastocyst, which is the stage of embryonic development when implantation occurs. ESCs may be mammalian ESCs. For example they may be mouse, human or rat ESCs ESCs are pluripotent stem cells that have the ability to proliferate indefinitely in vitro in the undifferentiated state. Under the appropriate conditions, ESCs can also be differentiated in vitro and in vivo to cell types representative of all three germ layers (mesoderm, endoderm and ectoderm). Morphologically, the cells have a high nuclear to cytoplasmic ratio and grow as distinct colonies. They also express high levels of alkaline phosphatase, telomerase and the transcription factors Oct-4 and Nanog. Routinely, hESC are characterized by the expression of cell surface markers, including stage-specific embryonic antigens (SSEA)-3 and SSEA-4, tumor rejection antigen (Tra)-1-60 and Tra-1-81. However, these surface antigens are not unique to hESC and have been previously characterized in human embryonal carcinoma (EC) cells.

In the present invention, undifferentiated embryonic stem cells express PODXL on their surface.

Pluripotent Stem Cells

Pluripotent stem cells are true stem cells, with the potential to make any differentiated cell in the body. However, they cannot contribute to making the extraembryonic membranes which are derived from the trophoblast. Several types of pluripotent stem cells have been found.

Multipotent Stem Cells

Multipotent stem cells are true stem cells but can only differentiate into a limited number of types. For example, the bone marrow contains multipotent stem cells that give rise to all the cells of the blood but not to other types of cells. Multipotent stem cells are found in adult animals. It is thought that every organ in the body contains them where they can replace dead or damaged cells.

Methods of characterising stem cells are known in the art, and include the use of standard assay methods such as clonal assay, flow cytometry, long-term culture and molecular biological techniques e.g. PCR, RT-PCR and Southern blotting.

Adult Stem Cells

Adult stem cells comprise a wide variety of types including neuronal, skin and the blood forming stem cells which are the active component in bone marrow transplantation.

These latter stem cell types are also the principal feature of umbilical cord-derived stem. cells. Adult stem cells can mature both in the laboratory and in the body into functional, more specialised cell types although the exact number of cell types is limited by the type of stem cell chosen.

Induced Pluripotent Stem Cells

Induced pluripotent stem cells, commonly abbreviated as iPS cells or iPSCs, are a type of pluripotent stem cell artificially derived from a non-pluripotent cell, typically an adult somatic cell, by inserting certain genes. iPS cells are reviewed and discussed in Takahashi, K. & Yamanaka (2006), Yamanaka S, et. al. (2007), Wernig M, et. al. (2007), Maherali N, et. al. (2007), Yu J, et al. (2007) and Takahashi et al., (2007), all of which are incorporated herein by reference.

iPS cells are typically derived by transfection of certain stem cell-associated genes into non-pluripotent cells, such as adult fibroblasts. Transfection is typically achieved through viral vectors, for example through retroviral reprogramming. Transfected genes include the master transcriptional regulators Oct-3/4 (Pouf51) and Sox2, although it is suggested that other genes enhance the efficiency of induction. After 3-4 weeks, small numbers of transfected cells begin to become morphologically and biochemically similar to pluripotent stem cells, and are typically isolated through morphological selection, doubling time, or through a reporter gene and antibiotic infection.

IPSCs may be induced from somatic cells such as fibroblasts by transfection with one or more transcription factors. In some cases, cells are transformed with Oct3/4, Sox2, c-Myc and Klf4. The cells may be additionally transfected with other genes, including transcription factors and/or marker genes. The genes may be introduced using a transposon system such as the Cre/loxP recombination system, or using non-integrating vectors in order to produce iPSCs free of exogenous reprogramming genes. Transfection may be achieved using viral vectors, such as a retrovirus. The virus may be an amphotropic virus. Once the cells have been transfected, they may be grown on feeder cells before transfer to an ESC culture medium.

The IPSCs may be derived from rabbit, guinea pig, rat, mouse or other rodent, cat, dog, pig, sheep, goat, cattle, horse, non-human primate or other non-human vertebrate organism. In preferred embodiments the IPSCs are derived from human cells.

iPS cells useful in the invention may be derived from any suitable cell type, including lung, foreskin fibroblasts, skin fibroblasts, keratinocytes, blood progenitor cells, bone marrow cells, hepatocytes, gastric epithelial cells, pancreatic cells, neural stem cells, B lymphocytes, ES derived somatic cells and embryonic fibroblasts. The iPS cells may be derived from human, mouse or other mammals. Preferably, the iPS cells are human. In some cases, the cells are not human dermal fibroblasts. The IPSCs may exhibit similar patterns of gene expression and phenotype to ESCs. In the present invention, the undifferentiated IPSCs express PODXL on their surface.

Like ESCs, future therapeutic applications of differentiated induced pluripotent stem cells carry a risk of teratoma formation by contaminating residual undifferentiated IPSC. Despite this problem, currently there are not many strategies developed to separate these cell populations.

Culture of Stem Cells

Any suitable method of culturing stem cells may be used.

Any suitable container may be used to propagate stem cells. Suitable containers include those described in US Patent Publication US2007/0264713 (Terstegge).

Containers may include bioreactors and spinners, for example. A "bioreactor", as the term is used in this document, is a container suitable for the cultivation of eukaryotic cells, for example animal cells or mammalian cells, such as in a large scale. A typical cultivation volume of a regulated bioreactor is between 20 ml and 500 ml.

The bioreactor may comprise a regulated bioreactor, in which one or more conditions may be controlled or monitored, for example, oxygen partial pressure. Devices for measuring and regulating these conditions are known in the art. For example, oxygen electrodes may be used for oxygen partial pressure. The oxygen partial pressure can be regulated via the amount and the composition of the selected gas mixture (e.g., air or a mixture of air and/or oxygen and/or nitrogen and/or carbon dioxide). Suitable devices for measuring and regulating the oxygen partial pressure are described by Bailey, J E. (Bailey, J E., Biochemical Engineering Fundamentals, second edition, McGraw-Hill, Inc. ISBN 0-07-003212-2 Higher Education, (1986)) or Jackson A T. Jackson A T., Verfahrenstechnik in der Biotechnologie, Springer, ISBN 3540561900 (1993)).

Other suitable containers include spinners. Spinners are regulated or unregulated bioreactors, which can be agitated using various agitator mechanisms, such as glass ball agitators, impeller agitators, and other suitable agitators. The cultivation volume of a. spinner is typically between 20 ml and 500 ml. Roller bottles are round cell culture flasks made of plastic or glass having a culture area of between 400 and 2000 $cm^2$. The cells are cultivated along the entire inner surface of these flasks; the cells are coated with culture medium accomplished by a "rolling" motion, i.e. rotating the bottles about their own individual axis.

Alternatively, culture may be static, i.e. where active agitation of the culture/culture media is not employed. By reducing agitation of the culture, aggregates of cells may be allowed to form. Whilst some agitation may be employed to encourage distribution and flow of the culture media over the cultured cells this may be applied so as not to substantially disrupt aggregate formation. For example, a low rpm agitation, e.g. less than 30 rpm or less than 20 rpm, may be employed.

Propagation with Passage

The methods and compositions described here may comprise passaging, or splitting during culture. The methods may involve continuous or continual passage.

By "continual" or "continuous", we mean that our methods enable growth of stem cells in a fashion that enables them to be passaged, e.g., taken off the plates or microcarriers on which they are growing and transferred to other plates, microcarriers or particles, and that this process may be repeated at least once, for example twice, three times, four times, five times, etc. In some cases, this may be repeated any number of times, for example indefinitely or infinitely.

Cells in culture may be dissociated from the substrate or flask, and "split", subcultured, or passaged, by dilution into tissue culture medium and replating.

Cells growing on particles may be passaged back onto particle culture. Alternatively, they may be passaged back onto conventional (2D) cultures. Tissue culture cells growing on plates may be passaged onto particle culture.

The term "passage" may generally refer to the process of taking an aliquot of a cell culture, dissociating the cells completely or partially, diluting and inoculating into medium. The passaging may be repeated one or more times. The aliquot may comprise the whole or a portion of the cell culture. The cells of the aliquot may be completely, partially or not confluent. The passaging may comprise at least some of the following sequence of steps: aspiration, rinsing, trypsinization, incubation, dislodging, quenching, re-seeding and aliquoting. The protocol published by the Hedrick Lab, UC San Diego may be used (http://hedricklab.ucsd.edu/Protocol/COSCell.html).

The cells may be dissociated by any suitable means, such as mechanical or enzymatic means known in the art. The cells may be broken up by mechanical dissociation, for example using a cell scraper or pipette. The cells may be dissociated by sieving through a suitable sieve size, such as through 100 micron or 500 micron sieves. The cells may be split by enzymatic dissociation, for example by treatment with collagenase or trypLE harvested. The dissociation may be complete or partial.

The dilution may be of any suitable dilution. The cells in the cell culture may be split at any suitable ratio. For example, the cells may be split at a ratio of 1:2 or more, 1:3 or more, 1:4 or more or 1:5 or more. Thus, stem cells may be passaged for 1 passage or more. For example, stem cells may be passaged for 2, 3, 4, 5, 6, 7, 8, 9, 10, 11, 12, 13, 14, 15, 16, 17, 18, 19, 20, 21, 22, 23, 24, 25 passages or more. Passages may be expressed as generations of cell growth. Stem cells may be propagated for 1, 2, 3, 4, 5, 6, 7, 8, 9, 10, 11, 12, 13, 14, 15, 16, 17, 18, 19, 20, 21, 22, 23, 24, 25 generations or more. Passages may also be expressed as the number of cell doublings. Stem cells may be propagated for 1, 2, 3, 4, 5, 6, 7, 8, 9, 10, 11, 12, 13, 14, 15, 16, 17, 18, 19, 20, 21, 22, 23, 24, 25 cell doublings or more.

Maintenance of Stem Cell Characteristics

The propagated stem cells may retain at least one characteristic of a mammalian (e.g. a primate or human) stem cell. The stem cells may retain the characteristic after one or more passages. They may do so after a plurality of passages. They may do so after the stated number of passages as described above.

The characteristic may comprise a morphological characteristic, immunohistochemical characteristic, a molecular biological characteristic, etc. The characteristic may comprise a biological activity.

Stem Cell Characteristics

The stem cells may display any of the following stem cell characteristics.

Stem cells may display increased expression of Oct4 and/or SSEA-1 and/or TRA-1-60. Stem cells which are self-renewing may display a shortened cell cycle compared to stem cells which are not self-renewing.

Stem cells may display defined morphology. For example, in the two dimensions of a standard microscopic image, human embryonic stem cells display high nuclear/cytoplasmic ratios in the plane of the image, prominent nucleoli, and compact colony formation with poorly discernable cell junctions.

Stem cells may also be characterized by expressed cell markers as described in further detail below.

Expression of Pluripotency Markers

The biological activity that is retained may comprise expression of one or more pluripotency markers.

Stage-specific embryonic antigens (SSEA) are characteristic of certain embryonic cell types. Antibodies for SSEA markers are available from the Developmental Studies Hybridoma Bank (Bethesda Md.). Other useful markers are detectable using antibodies designated Tra-1-60 and Tra-1-81 (Andrews et al., Cell Lines from Human Germ Cell Tumors, in E. J. Robertson, 1987, supra). Human embryonic stem cells are typically SSEA-1 negative and SSEA-4 positive. hEG cells are typically SSEA-1 positive. Differentiation of primate pluripotent stem cells (pPS) cells in vitro results in the loss of SSEA-4, Tra-1-60, and Tra-1-81 expression and increased expression of SSEA-1. pPS cells can also be characterized by the presence of alkaline phosphatase activity, which can be detected by fixing the cells with 4% paraformaldehyde, and then developing with Vector Red as a substrate, as described by the manufacturer (Vector Laboratories, Burlingame Calif.).

Embryonic stem cells are also typically telomerase positive and OCT-4 positive. Telomerase activity can be determined using TRAP activity assay (Kim et al., Science 266:2011, 1997), using a commercially available kit (TRAPeze® XK Telomerase Detection Kit, Cat. s7707; Intergen Co., Purchase N.Y.; or TeloTAGGG™ Telomerase PCR ELISA plus, Cat. 2,013,89; Roche Diagnostics, Indianapolis). hTERT expression can also be evaluated at the mRNA level by RT-PCR. The LightCycler TeloTAGGG™ hTERT quantification kit (Cat. 3,012,344; Roche Diagnostics) is available commercially for research purposes.

Any one or more of these pluripotency markers, including FOXD3, PODXL, alkaline phosphatase, OCT-4, SSEA-4, TRA-1-60 and Mab84, etc, may be retained by the propagated stem cells.

Detection of markers may be achieved through any means known in the art, for example immunologically. Histochemical staining, flow cytometry (FACS), Western Blot, enzyme-linked immunoassay (ELISA), etc may be used.

Flow immunocytochemistry may be used to detect cell-surface markers. immunohistochemistry (for example, of fixed cells or tissue sections) may be used for intracellular or cell-surface markers. Western blot analysis may be conducted on cellular extracts. Enzyme-linked immunoassay may be used for cellular extracts or products secreted into the medium.

For this purpose, antibodies to the pluripotency markers as available from commercial sources may be used.

Antibodies for the identification of stem cell markers including the Stage-Specific Embryonic Antigens 1 and 4 (SSEA-1 and SSEA-4) and Tumor Rejection Antigen 1-60 and 1-81 (TRA-1-60, TRA-1-81) may be obtained commercially, for example from Chemicon International, Inc (Temecula, Calif., USA). The immunological detection of these antigens using monoclonal antibodies has been widely used to characterize pluripotent stem cells (Shamblott M. J. et. al. (1998) PNAS 95: 13726-13731; Schuldiner M. et. al. (2000). PNAS 97: 11307-11312; Thomson J. A. et. al. (1998). Science 282: 1145-1147; Reubinoff B. E. et. al. (2000). Nature Biotechnology 18: 399-404; Henderson J. K. et. al. (2002). Stem Cells 20: 329-337; Pera M. et. al. (2000). J. Cell Science 113: 5-10.).

The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. Sequence data for the particular markers listed in this disclosure can be obtained from public databases such as GenBank (URL www.ncbi.nlm.nih.gov:80/entrez). See U.S. Pat. No. 5,843,780 for further details.

Substantially all of the propagated cells, or a substantial portion of them, may express the marker(s). For example, the percentage of cells that express the marker or markers may be 50% or more, 60% or more, 70% or more, 80% or more, 90% or more, 93% or more, 95% or more, 97% or more, 98% or more, 99% or more, or substantially 100%.

Cell Viability

The biological activity may comprise cell viability after the stated number of passages. Cell viability may be assayed in various ways, for example by Trypan Blue exclusion.

A protocol for vital staining follows. Place a suitable volume of a cell suspension (20-200 μL) in appropriate tube add an equal volume of 0.4% Trypan blue and gently mix, let stand for 5 minutes at room temperature. Place 10 μl of stained cells in a hemocytometer and count the number of viable (unstained) and dead (stained) cells. Calculate the average number of unstained cells in each quadrant, and multiply by $2\times10^4$ to find cells/ml. The percentage of viable cells is the number of viable cells divided by the number of dead and viable cells.

The viability of cells may be 50% or more, 60% or more, 70% or more, 80% or more, 90% or more, 93% or more, 95% or more, 97% or more, 98% or more, 99% or more, or substantially 100%.

Karyotype

The propagated stem cells may retain a normal karyotype during or after propagation. A "normal" karyotype is a karyotype that is identical, similar or substantially similar to a karyotype of a parent stem cell from which the stem cell is derived, or one which varies from it but not in any substantial manner. For example, there should not be any gross anomalies such as translocations, loss of chromosomes, deletions, etc.

Karyotype may be assessed by a number of methods, for example visually under optical microscopy. Karyotypes may be prepared and analyzed as described in McWhir et al. (2006), Hewitt et al. (2007), and Gallimore and Richardson (1973). Cells may also be karyotyped using a standard G-banding technique (available at many clinical diagnostics labs that provide routine karyotyping services, such as the Cytogenetics Lab at Oakland Calif.) and compared to published stem cell karyotypes.

All or a substantial portion of propagated cells may retain a normal karyotype. This proportion may be 50% or more, 60% or more, 70% or more, 80% or more, 90% or more, 93% or more, 95% or more, 97% or more, 98% or more, 99% or more or substantially 100%.

Pluripotency

The propagated stem cells may retain the capacity to differentiate into all three cellular lineages, i.e., endoderm, ectoderm and mesoderm. Methods of induction of stem cells to differentiate each of these lineages are known in the art and may be used to assay the capability of the propagated stem cells. All or a substantial portion of propagated cells may retain this ability. This may be 50% or more, 60% or more, 70% or more, 80% or more, 90% or more, 93% or more, 95% or more, 97% or more, 98% or more, 99% or more, or substantially 100% of the propagated stem cells.

The pluripotency of the generated stem cells may be determined by use of suitable assays. Such assays may comprise detecting one or more markers of pluripotency, e.g. SSEA-1 antigen, alkaline phosphatase activity, detection of Oct-4 gene and/or protein expression, by observing the extent of teratoma formation in SCID mice or formation of embryoid bodies. Pluripotency of hESC may be defined by the expression of one or more markers such as Oct-4, SSEA-4, Tra-1-60, Tra-1-81, SOX-2 and GCTM-2.

Co-Culture and Feeders

Methods may comprise culturing stem cells in the presence or absence of co-culture. The term "co-culture" refers to a mixture of two or more different kinds of cells that are grown together, for example, stromal feeder cells. The two or more different kinds of cells may be grown on the same surfaces, such as particles or cell container surfaces, or on different surfaces. The different kinds of cells may be grown on different particles.

Feeder cells, as the term is used in this document, may mean cells which are used for or required for cultivation of cells of a different type. In the context of stem cell culture, feeder cells have the function of securing the survival, proliferation, and maintenance of cell pluripotency. Cell pluripotency may be achieved by directly co-cultivating the feeder cells. Alternatively, or in addition, the feeder cells may be cultured in a medium to condition it. The conditioned medium may be used to culture the stem cells.

The inner surface of the container such as a culture dish may be coated with a feeder layer of mouse embryonic skin cells that have been treated so they will not divide. The feeder cells release nutrients into the culture medium which are required for ES cell growth. The stem cells growing on particles may therefore be grown in such coated containers.

Arrangements in which feeder cells are absent or not required are also possible. For example, the cells may be grown in medium conditioned by feeder cells or stem cells.

Media and Feeder Cells

Media for isolating and propagating pluripotent stem cells can have any of several different formulas, as long as the cells obtained have the desired characteristics, and can be propagated further.

Suitable sources are as follows: Dulbecco's modified Eagles medium (DMEM), Gibco#11965-092; Knockout Dulbecco's modified Eagles medium (KO DMEM), Gibco#10829-018; 200 mM L-glutamine, Gibco#15039-027; non-essential amino acid solution, Gibco 11140-050; beta-mercaptoethanol, Sigma#M7522; human recombinant basic fibroblast growth factor (bFGF), Gibco#13256-029. Exemplary serum-containing embryonic stem (ES) medium is made with 80% DMEM (typically KO DMEM), 20% defined fetal bovine serum (FBS) not heat inactivated, 0.1 mM non-essential amino acids, 1 mM L-glutamine, and 0.1 mM beta-mercaptoethanol. The medium is filtered and stored at 4 degrees C. for no longer than 2 weeks. Serum-free embryonic stem (ES) medium is made with 80% KO DMEM, 20% serum replacement, 0.1 mM non-essential amino acids, 1 mM L-glutamine, and 0.1 mM beta-mercaptoethanol. An effective serum replacement is Gibco#10828-028. The medium is filtered and stored at 4 degrees C. for no longer than 2 weeks. Just before use, human bFGF is added to a final concentration of 4 ng/mL (Bodnar et al., Geron Corp, International Patent Publication WO 99/20741).

The media may comprise Knockout DMEM media (Invitrogen-Gibco, Grand Island, N.Y.), supplemented with 10% serum replacement media (Invitrogen-Gibco, Grand Island, N.Y.), 5 ng/ml FGF2 (Invitrogen-Gibco, Grand Island, N.Y.) and 5 ng/ml PDGF AB (Peprotech, Rocky Hill, N.J.).

Feeder cells (where used) may be propagated in mEF medium, containing 90% DMEM (Gibco#11965-092), 10% FBS (Hyclone#30071-03), and 2 mM glutamine. mEFs are propagated in T150 flasks (Coming#430825), splitting the cells 1:2 every other day with trypsin, keeping the cells subconfluent. To prepare the feeder cell layer, cells are irradiated at a dose to inhibit proliferation but permit synthesis of important factors that support human embryonic stem cells (about 4000 rads gamma irradiation). Six-well culture plates (such as Falcon#304) are coated by incubation at 37 degrees C. with 1 mL 0.5% gelatin per well overnight, and plated with 375,000 irradiated mEFs per well. Feeder cell layers are typically used 5 h to 4 days after plating.

Conditions for culturing other stem cells are known, and can be optimized appropriately according to the cell type. Media and culture techniques for particular cell types referred to in the previous section are provided in the references cited.

Serum Free Media

The methods and compositions described here may include culture of stem cells in a serum-free medium.

The term "serum-free media" may comprise cell culture media which is free of serum proteins, e.g. fetal calf serum. Serum-free media are known in the art, and are described for example in U.S. Pat. Nos. 5,631,159 and 5,661,034. Serum-free media are commercially available from, for example, Gibco-BRL (Invitrogen).

The serum-free media may be protein free, in that it may lack proteins, hydrolysates, and components of unknown composition. The serum-free media may comprise chemically-defined media in which all components have a known chemical structure. Chemically-defined serum-free media is advantageous as it provides a completely defined system which eliminates variability and allows for improved reproducibility and more consistent performance, and decreases possibility of contamination by adventitious agents. The serum-free media may comprise Knockout DMEM media (Invitrogen-Gibco, Grand Island, N.Y.).

The serum-free media may be supplemented with one or more components, such as serum replacement media, at a concentration of for example, 5%, 10%, 15%, etc. The serum-free media may be supplemented with 10% serum replacement media from Invitrogen-Gibco (Grand Island, N.Y.).

The serum-free medium in which the dissociated or disaggregated embryonic stem cells are cultured may comprise one or more growth factors. A number of growth factors are known in the art, including FGF2, IGF-2, Noggin, Activin A, TGF beta 1, HRG1 beta, LIF, S1 P, PDGF, BAFF, April, SCF, Flt-3 ligand, Wnt3A and others. The growth factor(s) may be used at any suitable concentration such as between 1 pg/ml to 500 ng/ml.

Media Supplements

Culture media may be supplemented with one or more additives. For example, these may be selected from one or more of: a lipid mixture, Bovine Serum Albumin (e.g. 0.1% BSA), hydrolysate of soybean protein.

Sources of Induced Pluripotent Stem Cells

Several methods have now been provided for the isolation of pluripotent stem cells that do not lead to the destruction of an embryo, e.g. by transforming (inducing) adult somatic cells or germ cells. These methods include:

1. Reprogramming by nuclear transfer. This technique involves the transfer of a nucleus from a somatic cell into an oocyte or zygote. In some situations this may lead to the creation of an animal-human hybrid cell. For example, cells may be created by the fusion of a human somatic cell with an animal oocyte or zygote or fusion of a human oocyte or zygote with an animal somatic cell.

2. Reprogramming by fusion with embryonic stem cells. This technique involves the fusion of a somatic cell with an embryonic stem cell. This technique may also lead to the creation of animal-human hybrid cells, as in 1 above.

3. Spontaneous re-programming by culture. This technique involves the generation of pluripotent cells from non-pluripotent cells after long term culture. For example, pluripotent embryonic germ (EG) cells have been generated by long-term culture of primordial germ cells (PGC) (Matsui et al., Derivation of pluripotential embryonic stem cells from murine primordial germ cells in culture. Cell 70, 841-847, 1992, incorporated herein by reference). The development of pluripotent stem cells after prolonged culture of bone marrow-derived cells has also been reported (Jiang et al., Pluripotency of mesenchymal stem cells derived from adult marrow. Nature 418, 41-49, 2002, incorporated herein by reference). They designated these cells multipotent adult progenitor cells (MAPCs). Shinohara et al also demonstrated that pluripotent stem cells can be generated during the course of culture of germline stem (GS) cells from neonate mouse testes, which they designated multipotent germline stem (mGS) cells (Kanatsu-Shinohara et al., Generation of pluripotent stem cells from neonatal mouse testis. Cell 119, 1001-1012, 2004).

4. Reprogramming by defined factors. For example the generation of iPS cells by the retrovirus-mediated introduction of transcription factors (such as Oct-3/4, Sox2, c-Myc, and KLF4) into mouse embryonic or adult fibroblasts, e.g. as described above. Kaji et al (Virus-free induction of pluripotency and subsequent excision of reprogramming factors. Nature. Online publication 1 March 2009) also describe the non-viral transfection of a single multiprotein expression vector, which comprises the coding sequences of c-Myc, Klf4, Oct4 and Sox2 linked with 2A peptides, that can reprogram both mouse and human fibroblasts. iPS cells produced with this non-viral vector show robust expression of pluripotency markers, indicating a reprogrammed state confirmed functionally by in vitro differentiation assays and formation of adult chimaeric mice. They succeeded in establishing reprogrammed human cell lines from embryonic fibroblasts with robust expression of pluripotency markers.

Methods 1-4 are described and discussed by Shinya Yamanaka in Strategies and New Developments in the Generation of Patient-Specific Pluripotent Stem Cells (Cell Stem Cell 1, July 2007 ©2007 Elsevier Inc), incorporated herein by reference.

5. Derivation of hESC lines from single blastomeres or biopsied blastomeres. See Klimanskaya I, Chung Y, Becker S, Lu S J, Lanza R. Human embryonic stem cell lines derived from single blastomeres. Nature 2006; 444:512, Lei et al Xeno-free derivation and culture of human embryonic stem cells: current status, problems and challenges. Cell Research (2007) 17:682-688, Chung Y, Klimanskaya I, Becker S, et al. Embryonic and extraembryonic stem cell lines derived from single mouse blastomeres. Nature. 2006; 439:216-219. Klimanskaya I, Chung Y, Becker S, et al. Human embryonic stem cell lines derived from single blastomeres. Nature. 2006; 444:481-485. Chung Y, Klimanskaya I, Becker S, et al. Human embryonic stem cell lines generated without embryo destruction. Cell Stem Cell. 2008; 2:113-117 and Dusko llic et al (Derivation of human embryonic stem cell lines from biopsied blastomeres on human feeders with a minimal exposure to xenomaterials. Stem Cells And Development), all incorporated herein by reference.

6. hESC lines obtained from arrested embryos which stopped cleavage and failed to develop to morula and blastocysts in vitro. See Zhang X, Stojkovic P, Przyborski S, et al. Derivation of human embryonic stem cells from developing and arrested embryos. Stem Cells 2006; 24:2669-2676 and Lei et al Xeno-free derivation and culture of human embryonic stem cells: current status, problems and challenges. Cell Research (2007) 17:682-688, both incorporated herein by reference.

7. Parthogenesis (or Parthenogenesis). This technique involves chemical or electrical stimulation of an unfertilised egg so as to cause it to develop into a blastomere from which embryonic stem cells may be derived. For example, see Lin et al. Multilineage potential of homozygous stem cells derived from metaphase II oocytes. Stem Cells. 2003; 21(2):152-61 who employed the chemical activation of nonfertilized metaphase II oocytes to produce stem cells.

8. Stem cells of fetal origin. These cells lie between embryonic and adult stem cells in terms of potentiality and may be used to derive pluripotent or multipotent cells. Human umbilical-cord-derived fetal mesenchymal stem cells (UC fMSCs) expressing markers of pluripotency (including Nanog, Oct-4, Sox-2, Rex-1, SSEA-3, SSEA-4, Tra-1-60, and Tra-1-81, minimal evidence of senescence as shown by β-galactosidase staining, and the consistent expression of telomerase activity) have been successfully derived by Chris H. Jo et al (Fetal mesenchymal stem cells derived from human umbilical cord sustain primitive characteristics during extensive expansion. Cell Tissue Res (2008) 334:423-433, incorporated herein by reference). Winston Costa Pereira et al (Reproducible methodology for the isolation of mesenchymal stem cells from human umbilical cord and its potential for cardiomyocyte generation J Tissue Eng Regen Med 2008; 2: 394-399, incorporated herein by reference) isolated a pure population of mesenchymal stem cells from Wharton's jelly of the human umbilical cord. Mesenchymal stem cells derived from Wharton's jelly are also reviewed in Troyer & Weiss (Concise Review: Wharton's Jelly-Derived Cells Are a primitive Stromal Cell Population. Stem Cells 2008:26:591-599). Kim et al (Ex vivo characteristics of human amniotic membrane-derived stem cells. Cloning Stem Cells 2007 Winter; 9(4):581-94, incorporated herein by reference) succeeded in isolating human amniotic membrane-derived mesenchymal cells from human amniotic membranes. Umbilical cord is a tissue that is normally discarded and stem cells derived from this tissue have tended not to attract moral or ethical objection.

Induced pluripotent stem cells have the advantage that they can be obtained by a method that does not cause the destruction of an embryo, more particularly by a method that does not cause the destruction of a human or mammalian embryo. As such, aspects of the invention may be performed or put into practice by using cells that have not been prepared exclusively by a method which necessarily involves the destruction of human or animal embryos from which those cells may be derived. This optional limitation is specifically intended to take account of Decision G0002/06 of 25 Nov. 2008 of the Enlarged Board of Appeal of the European Patent Office.

Differentiation of Undifferentiated Cells

Pluripotent stem cells may be induced to differentiate into a variety of different cell types. For example, the pluripotent stem cells may be induced to differentiate into cardiac cells (cardiomyocytes), hepatocytes, neural cells, cartilage (chondrocytes), muscle, fat (adipocytes), bone (osteocytes) or other cells. The pluripotent stem cells may be induced to form tissues such as epithelial tissues, mesoderm, endoderm, ectoderm or epidermis.

Methods of differentiating stem cells are known in the art and are described in for example Itskovitz-Eldor (2000) and Graichen et al (2007) and may be used with IPSCs. The cultured stem cells may also be used for the formation of embryoid bodies. Embryoid bodies, and methods for making them, are known in the art. The term "embryoid body" refers to spheroid colonies seen in culture which may be produced by the growth of embryonic stem cells in suspension. Embryoid bodies are of mixed cell types, and the distribution and timing of the appearance of specific cell types corresponds to that observed within the embryo. Embryoid bodies may be generated by plating out embryonic stem cells onto media such as semi-solid media. Methylcellulose media may be used as described in Lim et al, Blood. 1997; 90:1291-1299.

Embryonic stem cells may be induced to form embryoid bodies, for example using the methods described in Itskovitz-Eldor (2000). The embryoid bodies contain cells of all three embryonic germ layers (endoderm, ectoderm, mesoderm).

The embryoid bodies may be further induced to differentiate into different lineages for example by exposure to the appropriate induction factor or an environmental change. Graichen et al (2007) describes the formation of cardiomyocytes from human embryonic stem cells by manipulation of the p38MAP kinase pathway. Graichen demonstrates induction of cardiomyocyte formation from stem cells by exposure to a specific inhibitor of p38 MAP kinase such as SB203580 at less than 10 μm.

Differentiated cells may be employed for any suitable purpose, such as regenerative therapy and cell transplantation as known in the art.

Therapeutic Uses

Differentiated and undifferentiated pluripotent stem cells obtained (e.g. identified, isolated, separated, purified, or enriched) by the methods of the present invention have various uses in medicine, for example in cell therapy. Cell therapy may comprise the implantation or transplantation of cells, whether as a population of individual cells, or in the form of a cell aggregate or tissue, and/or regenerative therapy e.g. tissue regeneration, replacement and/or repair. Differentiated and undifferentiated pluripotent stem cells may be expanded in in vitro culture and directly administered into a patient. They may be used for the repopulation and/or repair of damaged tissue following trauma.

Pluripotent stem cells may be used directly, or used to generate ectodermal, mesodermal or endodermal progenitor cell populations, for regenerative therapy. Progenitor cells may be made by ex vivo expansion or directly administered into a patient. They may also be used for the re-population and/or repair of damaged tissue following trauma.

Thus, hematopoietic progenitor cells may be used for bone marrow replacement, while cardiac progenitor cells may be used for cardiac failure patients. Skin progenitor cells may be employed for growing skin grafts for patients and endothelial progenitor cells for endothelization of artificial prosthetics such as stents or artificial hearts.

Pluripotent stem cells may be used as sources of ectodermal, mesodermal or endodermal progenitor cells for the treatment of degenerative diseases such as diabetes, Huntington's disease, Alzheimer's disease and Parkinson's disease. They may be used as sources of mesodermal or endodermal progenitors for NK or dendritic cells for immunotherapy for cancer.

Pluripotent stem cells, ectodermal, mesodermal or endodermal progenitor cells and differentiated cells described here may be used for, or for the preparation of a pharmaceutical composition for, the treatment of a disease. Such disease may comprise a disease treatable by regenerative therapy, including cardiac failure, bone marrow disease, skin disease, burns, degenerative disease such as diabetes, Alzheimer's disease, Parkinson's disease and cancer.

Stem cells propagated as described herein (and differentiated cells derived therefrom) may be used for therapy, for example tissue reconstitution or regeneration in an individual patient in need thereof. The cells may be administered in a manner that permits them to graft to the intended tissue site and reconstitute or regenerate the functionally deficient area.

Pluripotent stem cells can be directed to differentiate into a variety of cell types, and offer the possibility of renewable sources of replacement cells and tissues to treat a range of diseases and disorders. These diseases and disorders include Huntington's disease, Parkinson's disease, Alzheimer's disease, spinal cord injury, bone injury (e.g. fracture), stroke, burns, heart disease, diabetes, osteoarthritis, and rheumatoid arthritis. Diseases and disorders requiring transplantable tissues and organs may be treated, and particularly in cases where it is useful to destroy undifferentiated cells before transplantation, for example to prevent the formation of teratoma.

Undifferentiated pluripotent stem cells and differentiated pluripotent stem cells obtained by any of the methods of the present invention may be formulated into medicaments and pharmaceutical compositions. The medicaments and pharmaceutical compositions may be provided for use in a method of medical treatment, as described above. Suitable pharmaceutical compositions may further comprise a pharmaceutically acceptable carrier, adjuvant or diluent.

Thus, the present invention also provides compositions, for example pharmaceutical compositions, and medicaments comprising cells which have been treated to remove or destroy undifferentiated pluripotent stem cells, using the methods of the invention.

The ability to identify and select undifferentiated pluripotent stem cells through the cell surface expression of PODXL enables compositions and medicaments to be provided which contain undifferentiated pluripotent stem cells and substantially no differentiated pluripotent stem cells or, alternatively, differentiated pluripotent stem cells and substantially no undifferentiated pluripotent stem cells. The language "substantially no" includes compositions in which the number of specified cells is less than about 10% of the total number of cells in the composition. More preferably this is less than about 9%, less than about 8%, less than about 7%, less than about 6%, less than about 5%, less than about 4%, less than about 3%, less than about 2%, or less than about 1%. In some embodiments the specified cells may be absent, or present in sufficiently low amounts so as to be beyond the limits of detection, i.e. the composition has substantially zero percent of the specified cells.

Differentiated and undifferentiated pluripotent stem cells isolated by a method according to the present invention may be used in a method of medical treatment. A method of medical treatment may comprise administering to an individual in need of treatment a therapeutically effective amount of a said medicament or pharmaceutical composition.

Differentiated and undifferentiated pluripotent stem cells obtained through methods and techniques according to this invention may be used to differentiate into another cell type for use in a method of medical treatment. Thus, the differentiated cell type may be derived from, and may be considered as a product of, a stem cell obtained by the methods and techniques described which has subsequently been permitted to differentiate. Pharmaceutical compositions may be provided comprising such differentiated cells, optionally together with a pharmaceutically acceptable carrier, adjuvant or diluent. Such pharmaceutical composition may be useful in a method of medical treatment.

A subject to be treated may be any animal or human. The subject is preferably mammalian, more preferably human. The subject may be male or female. The subject may be a patient. Therapeutic uses may be in human or animals (veterinary use).

Medicaments and pharmaceutical compositions according to aspects of the present invention may be formulated for administration by a number of routes, including but not limited to, parenteral, intravenous, intra-arterial, intramuscular, intratumoural, oral and nasal. The medicaments and compositions may be formulated for injection.

Administration is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Formulating Pharmaceutically Useful Compositions and Medicaments

Pluripotent stem cells bound, isolated and/or identified by methods of the present invention may be formulated into pharmaceutically useful compositions. In addition to the steps of the methods described herein, such methods may further comprise one or more steps selected from:

(a) identifying an undifferentiated or differentiated pluripotent stem cell or cells;

(b) isolating and/or obtaining the undifferentiated or differentiated pluripotent stem cell or cells;

(c) mixing the undifferentiated or differentiated pluripotent stem cell or cells with a pharmaceutically acceptable carrier, adjuvant or diluent.

Step (c) preferably results in formulation/preparation of a pharmaceutical composition or medicament suitable for therapeutic use.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The invention includes the combination of the aspects and preferred features described except where such a combination is clearly impermissible or expressly avoided.

The section headings used herein are for organizational purposes only and are not to be construed as limiting the subject matter described.

Unless context dictates otherwise, the descriptions and definitions of the features set out above are not limited to any particular aspect or embodiment of the invention and apply equally to all aspects and embodiments which are described.

Aspects and embodiments of the present invention will now be illustrated, by way of example, with reference to the accompanying figures. Further aspects and embodiments will be apparent to those skilled in the art. All documents mentioned in this text are incorporated herein by reference.

EXAMPLES

Example 1

Several antibody fragment formats of mAb 84 were engineered (FIG. 1) and expressed as soluble proteins in *E. coli*. We show that the cytotoxic properties of the antibody fragment is not only dependent on antigen-binding, but also the valency and flexibility of the antibody fragment format (i.e. the antibody molecule).

Materials and Methods

Vector Construction

The BspHI restriction sites in pET-39b were removed by using site directed mutagenesis (QuikChange® Multi Site Directed Mutagenesis kit, Stratagene) to change a single base pair at the recognition site with primers designed using the QuikChange® Primer Design Program (FIG. 9). The primers used were c547t-F, c547t-R, c1422t-F, c1422t-R, c4845t-F and c4845t-R and they were 5'-phosphorylated before the site directed mutagenesis PCR. The cytosine nucleotides at positions 547, 1422 and 4845 were replaced by thymine. The PCR product was transformed into XL1-Blue cells (Stratagene) and plated on LB+Kan (30 µg/ml) plates. The colony containing the vector with all three BspHI mutated away was verified by Big Dye sequencing (Applied Biosystems).

Figure 2A:
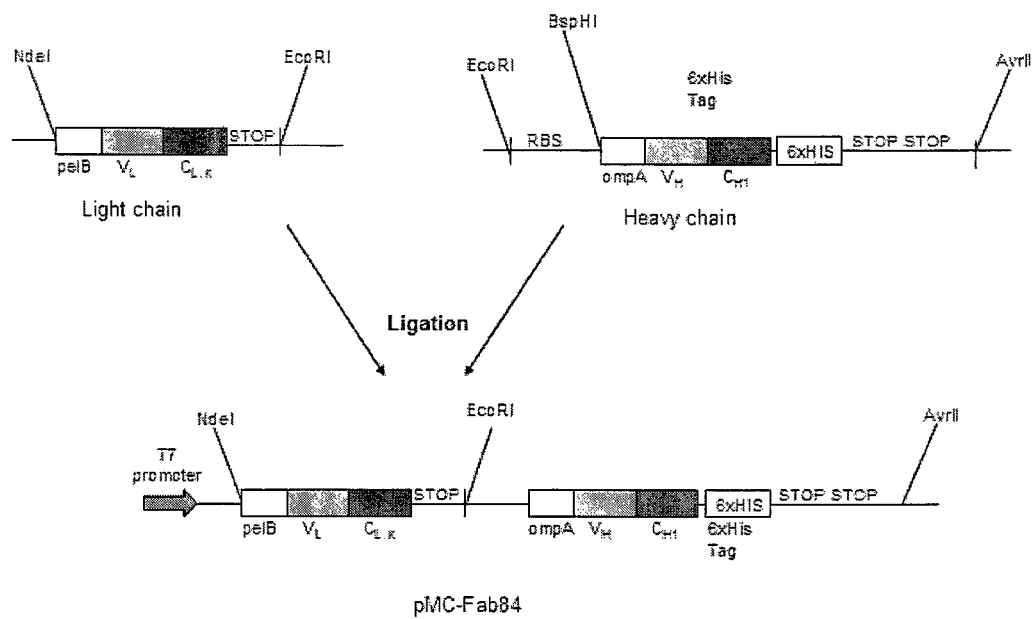
FIG. 2a. shows the construction of pMC-Fab84 encoding a Fab84 antibody fragment.

Obtaining pMC-Fab84: The heavy chain (VH-CH1) and light chain (VL-CL$_K$) were obtained in separate pUC57 plasmids from Genscript (Genscript, N.J.). The pET-39b plasmid without BspHI sites obtained above, and the light chain fragment, were digested separately with NdeI and EcoRI, and ligated together using T4 ligase. The ligation reaction was transformed into TOP10 cells (Invitrogen). The sequence of this plasmid, named pET-39b-Fab84LightChain, was verified using Big Dye sequencing. The plasmid pET-39b-Fab84LightChain and the heavy chain fragment were then digested separately by EcoRI and AvrII and ligated together using T4 ligase, before transformation into TOP10 cells. This vector is pMC-Fab84, and its sequence was verified via Big Dye sequencing. (FIG. 2a)

Figure 2B:
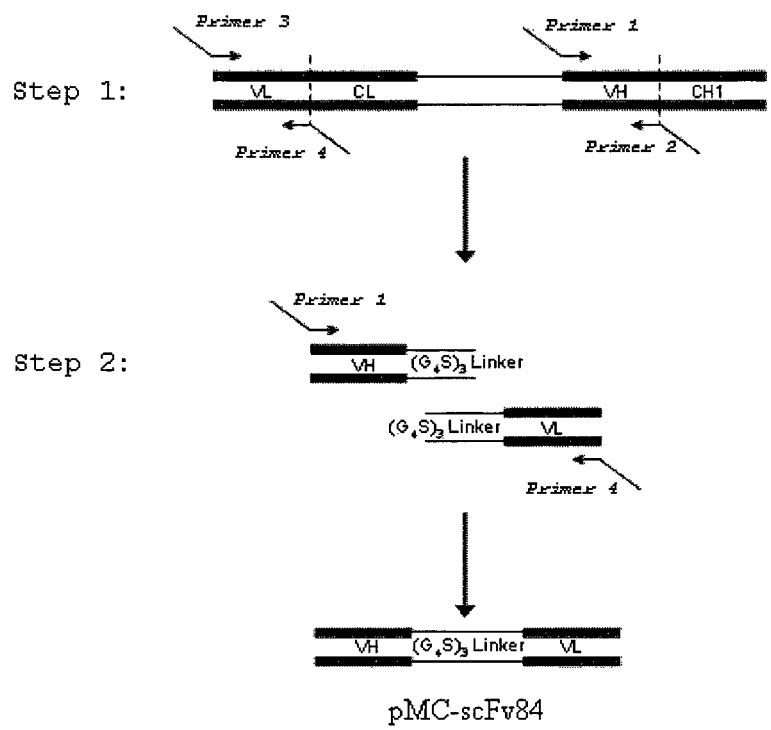
FIG. 2b. shows the construction of pMC-scFv84 encoding an scFv84 antibody fragment.

Obtaining pMC-scFv: Overlap PCR was used to construct the single chain variable fragment (scFv) version of the antibody. This scFv construct was named scFv84, and consists of the variable light chain connected by a 15 amino acid linker $(G_4S)_3$ followed by the variable heavy chain. Using pMC-Fab84 as the template, separate PCR reactions were done to amplify the variable heavy chain and variable light chain primers scFv84-NcoI_VH_F 1 (primer 1) and scFv84-VH_linker_R 2 (primer 2) were used to amplify the variable heavy chain and introduce the $(G_4S)_3$ linker at the C-terminal end; primers scFv84-linker_VL_F 3 (primer 3) and scFv84-VL_NotI_R 4 (primer 4) were used to amplify the variable light chain and introduce the $(G_4S)_3$ linker at the N-terminal end. In another PCR reaction, the previous two PCR reactions were used as templates with scFv84-NcoI_VH_F 1 (primer 1) and scFv84-VL_NotI_R 4 (primer 4) used as forward and reverse primers to amplify the scFv84 fragment. This fragment and pETscD1.3 plasmid (pET vector with T7 promoter and in-frame his tag) was digested with NdeI and NotI, before being ligated together. The vector is transformed into TOP10 cells and named pMC-scFv84. Its sequence was verified via Big Dye sequencing. (FIG. 2b)

Obtaining pMC-F(ab')$_2$84: An additional 10 amino acids (sequence DKTHTCPPCP) were inserted into the C-terminus of the heavy constant region to create the hinge region. Using pMC-Fab84 as the template, the primers F(ab')2-84-VH_AgeI_F and F(ab')2-84-VH_30nt_AvrII_R were used to amplify the later part of the heavy constant region such that the amplified fragment is flanked by an AgeI site and an AvrII site. Both pMC-Fab84 and the amplified fragment were digested by AgeI and AvrII, and ligated together using T4 ligase. The vector is transformed into TOP10 cells and named pMC-F(ab')284. Its sequence was verified via Big Dye sequencing.

Obtaining pMC-F(ab')$_2$(CPP)$_3$84: Using pMC-F(ab')$_2$84 as the template, two additional amino acids were inserted into the C terminus by using F(ab)2-(CPP)3_F and F(ab)2-(CPP)3_R in a site directed mutagenesis reaction (QuikChange® II XL Site-Directed Mutagenesis Kit, Stratagene). The resulting construct was designed to have 3 cysteines to form 3 interchain disulfide bonds in the expressed protein. The sequence was verified using Big Dye Sequencing.

Obtaining pMC-scFv84-5aa and pMC-scFv84-10aa: Using the pMC-scFv84 as the template, site directed mutagenesis (QuikChange II Site Directed Mutagenesis Kit, Stratagene) was used to remove the last 10 amino acids and 5 amino acids respectively. The primers used were scFv-5_F and scFv-5_R for pMC-scFv84-5aa, and scFv-10_F and scFv-10_R for pMC-scFv84-10aa. Colonies were selected using colony PCR, and the final vector sequence verified using Big Dye sequencing.

Obtaining pMC-scFv84-0aa: Overlap PCR was used to construct pMC-scFv84-0aa. Using pMC-scFv84 as the template, primers scFv-0_VH_F and scFv-0_VHVL_R was used to amplify the variable heavy chain connected to part of the light chain at the 3' end. This PCR reaction was used together with primer scFv-0_VL R as the forward and reverse primers for the next PCR reaction, using pMC-scFv84 as the template. The resulting fragment is the variable heavy chain directly connected to the variable light chain without any linker in between, flanked by NcoI and NotI sites. The fragment was then digested with NcoI and NotI and ligated into a similarly digested vector (pMC-scFv84 digested with NcoI and NotI). This new vector is named pMC-scFv84-0aa and its sequence verified by Big Dye sequencing.

Figure 3:
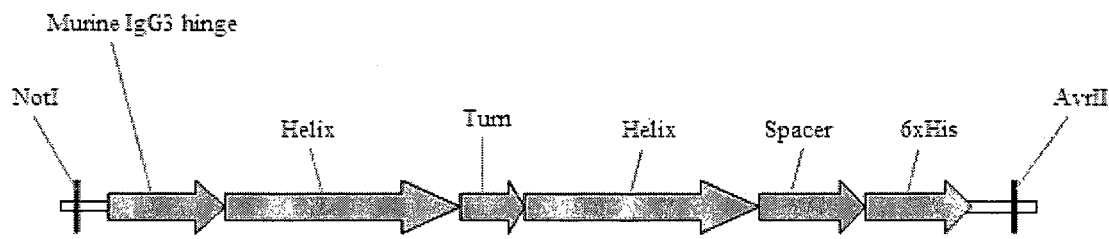
FIG. 3. is a representation of the primary structure of a gene sequence encoding a helix-turn-helix motif.

Obtaining pMC-scFv84-HTH: The helix-turn-helix motif consisting of a murine IgG3 hinge, helix, turn, helix, spacer and 6× his tag, was obtained in a pUC57 vector from Genscript (Genscript Inc. N.J., USA) (FIG. 3). The sequence was based on a dimerzation motif described by Pluckthun[30]. This plasmid was digested with NotI and AvrII, and ligated into pMC-scFv84 which was similarly digested. The vector pMC-scFv84 has NotI and AvrII sites at the end of the variable light chain, and the helix-turn-turn-helix motif is introduced into the C-terminus of the resulting protein. The resulting vector was named pMC-scFv84-HTH and its sequence verified by Big Dye sequencing.

All vectors were then transformed into *Escherichia coli* BL21(DE3) (Novagen) for protein expression.

Culture Fermentation Conditions

Fab84 and scFv84: Cells from glycerol stocks[1] were streaked out on LB+Kan (30 µg/ml) plates and a single colony picked for inoculation of 50 ml of overnight culture incubated at 37° C., 280 rpm. Fermentation culture were started with 5% inoculum of overnight culture into 2×YT+Kan (30 µg/ml) media in a 2 L glass culture flask, and grown at 37° C., 200 rpm until OD600 0.8-1.0. Cultures were induced with 50 µM IPTG at 30° C. and harvested at 5 hours post induction.

scFv84-HTH and scFv84-5aa: Cells from glycerol stocks[1] were streaked out on LB+Kan (30 µg/ml) plates and a single colony picked for inoculation of 50 ml of overnight culture incubated at 37° C., 280 rpm. Fermentation culture were started with 5% inoculum of overnight culture into 2×YT+Kan (30 µg/ml) media in a 2 L glass culture flask, and grown at 37° C., 200 rpm until OD600 2.0. Cultures were induced with 50 µM IPTG at 30° C. and harvested at 5 hours post induction.

[1]Glycerol stocks: 500 µl from a 5 ml culture of LB+Kan (30 µg/ml) inoculated with a single colony, with 500 µl of 50% glycerol.

Osmotic Shock

Cells were harvested by pelleting at 10,000×g (Hitachi Ultracentrifuge) for 30 min and media supernatant collected. The media supernatant fraction was filtered using a 0.2 µm filter (Nalgene) before storing at 4° C. to prevent microbial growth.

The pellet was then resuspended in Buffer A (1 mM EDTA, 200 mM Tris, 20% Sucrose, pH7.0) either by pipetting up and down, stirring suspension with a magnetic stir bar, or both. It was then incubated on ice for 30 min and spun at 15,000×g for 40 min. The supernatant was collected as Fraction A. The pellet was then resuspended in ice cold pure water, left on ice for 30 min, then centrifuged at 15,000×g for 40 min. The supernatant was collected as Fraction B.

Tangential Flow Filtration and Buffer Exchange

The fractions were concentrated using tangential flow filtration (Sartoflow® Slice 200 Benchtop Crossflow System, Sartorius-Stedim Biotech) with a 10 kDa MWCO membrane (Hydrosart) cassette and buffer exchanged into phosphate-buffered saline (Final conc: 137 mM Sodium Chloride, 2.7 mM Potassium Chloride, 10 mM Phosphate Buffer, 10× stock solution, First Base).

The media supernatant was concentrated to a final volume that is one-tenth of its original volume and buffer exchanged into PBS.

Fraction A, due to its higher viscosity, was diluted once with PBS, spun at 15,000×g for 1 hour to pellet particulate matter, and then clarified by filtering through a 0.45 µm filter (0.45 µm pore size CA Membrane, Corning). The filtrate was then concentrated to a volume that is 5-10 times its original volume, and buffer exchanged into PBS.

All fractions were clarified before purification.

Immobilized Metal Affinity Chromatography

The fractions were then purified using immobilized metal affinity chromatography (IMAC) with Talon® Polyhistidine-Tag Purification Resin (Clontech). Cobalt was the capturing metal ion. The column was equilibrated with Equilibrating/Washing Buffer (20 mM Sodium Phosphate, 300 mM NaCl, pH 7.0). The sample was applied to a 5 ml bed resin at a rate of ~1-2 ml/min. After washing for at least 3 times with Equilibrating/Washing Buffer, the sample was eluted with 10 columns volumes of Elution Buffer (20 mM Sodium Phosphate, 300 mM NaCl, 150 mM Imidazole, pH 7.0). The column was washed, stripped and regenerated as per the manufacturer's instructions. The eluted fractions were then analyzed by SDS-PAGE and Coomassie Brilliant Blue staining of the gel. For purification of scFv84-HTH, 1M urea was added to the sample and incubated at RT for 20 mins before loading onto the IMAC column. The protein was eluted with 120 mM imidazole.

SDS-PAGE and Western Blotting

Proteins were separated using 4-12% Bis-Tris gels (NuPAGE® Novex Bis Tris gels, NuPAGE® System, Invitrogen) and were visualized with Coomassie Brilliant Blue (Thermo Scientific Pierce Protein Research Products).

Proteins were electrophoretically transferred to a PVDF membrane at 110V for 1 hour. The blots were then blocked in TBST+1% low fat milk powder for one hour at room temperature or overnight at 4° C. After washing 5 min each time for 3 times, The blots were incubated with a his tag antibody conjugated to horse radish peroxidase (71840, Novagen) in 1:2000 dilution or an anti-mouse IgG antibody conjugated to horse radish peroxidase (A9917, Sigma Aldrich) in 1:2000 dilution. 3,3',5,5'-Tetramethylbenzidine (T0565, Sigma-Aldrich) was used as a substrate to detect for protein bands. Standards used were from SeeBlue Plus 2 (Invitrogen)

Size-Exclusion Chromatography

Twenty µl of purified samples were injected into a G2000 SuperSW column (Tosoh) and eluted with 0.2M sodium phosphate, 0.1M potassium sulphate pH 6.0 at 0.2 ml/min.

FACS

Human ES cells were used to test binding and cytotoxicity of antibody fragments. Purified antibody fragments were conjugated to Alexa Fluorophore 647 using Invitrogen labeling kit A20173 (for fragments larger than 12 kDa) or A20186 (for fragments larger than 30 kDa) according to the manufacturer's instructions. In each assay, 100 µg of protein was incubated with equal amounts of cells. Cells were harvested as single cell suspensions using trypsin, resuspended in 1% BSA/PBS and incubated for 30 min on ice for each antibody fragment. Binding of antibody fragments to cells was monitored using flow cytometry. Cytotoxicity towards cells was tested by PI exclusion assay and flow cytometry. Antibody fragments that displayed cytotoxic properties were also tested with human lung fibroblasts IMR 90 and iPS cells.

Results

Figure 4A:
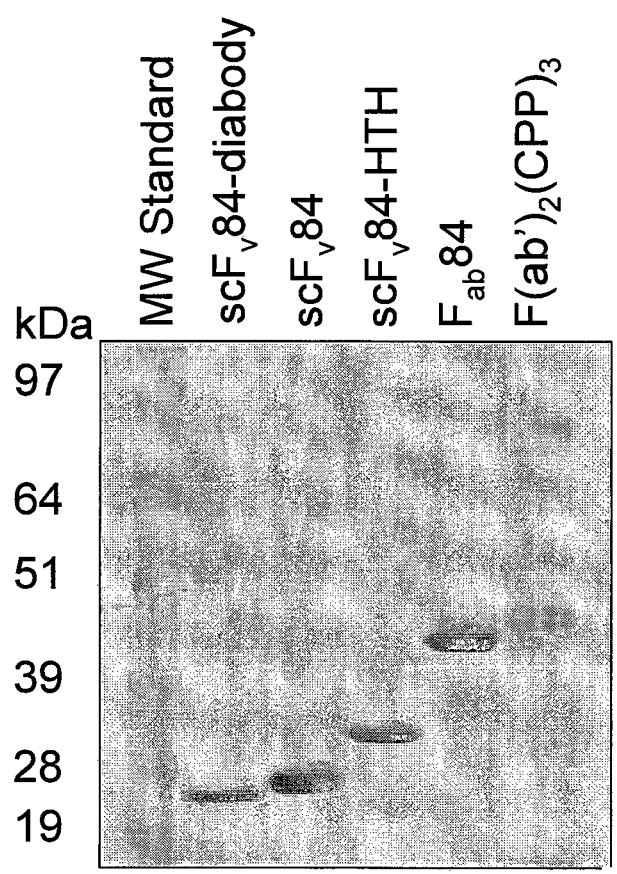
FIG. 4a. shows a Coomassie-stained SDS-PAGE under non-reducing conditions, of antibody molecules based on various antibody fragments.
Figure 4B:
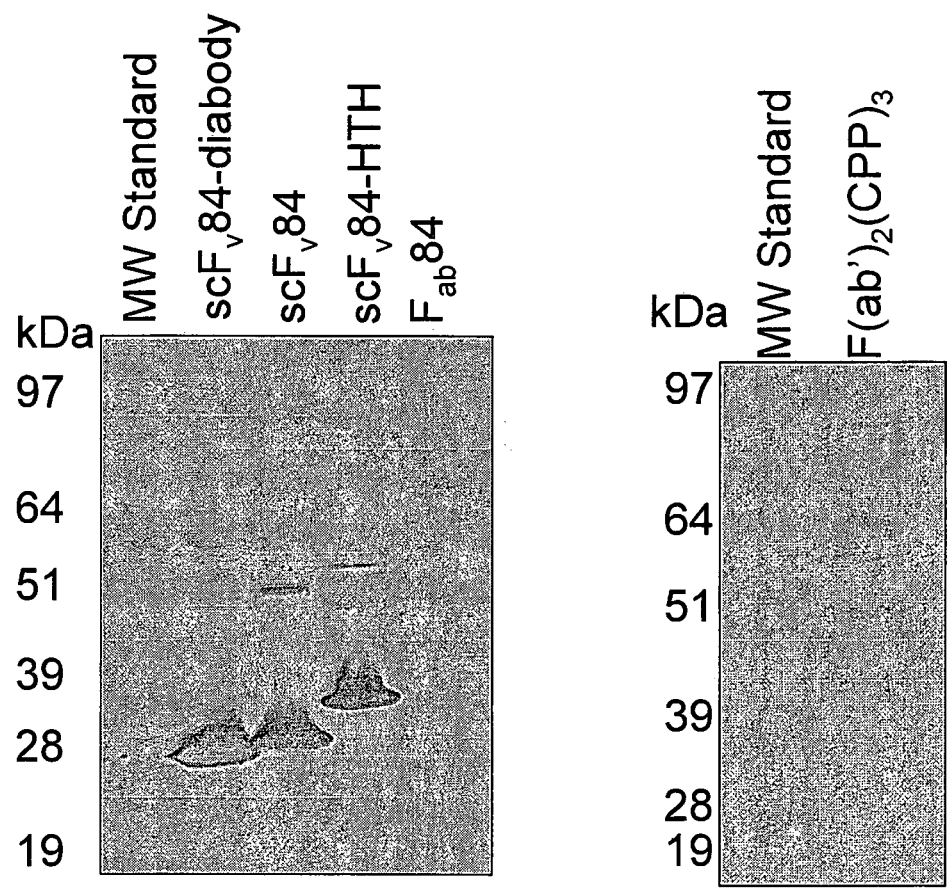
FIG. 4b. shows a Western blot of antibody molecules. $F(ab')_2(CPP)_3$ was detected with anti-mouse Ig (Fab specific)-HRP, while the other fragments were detected with anti-His-HRP.
Figure 5:
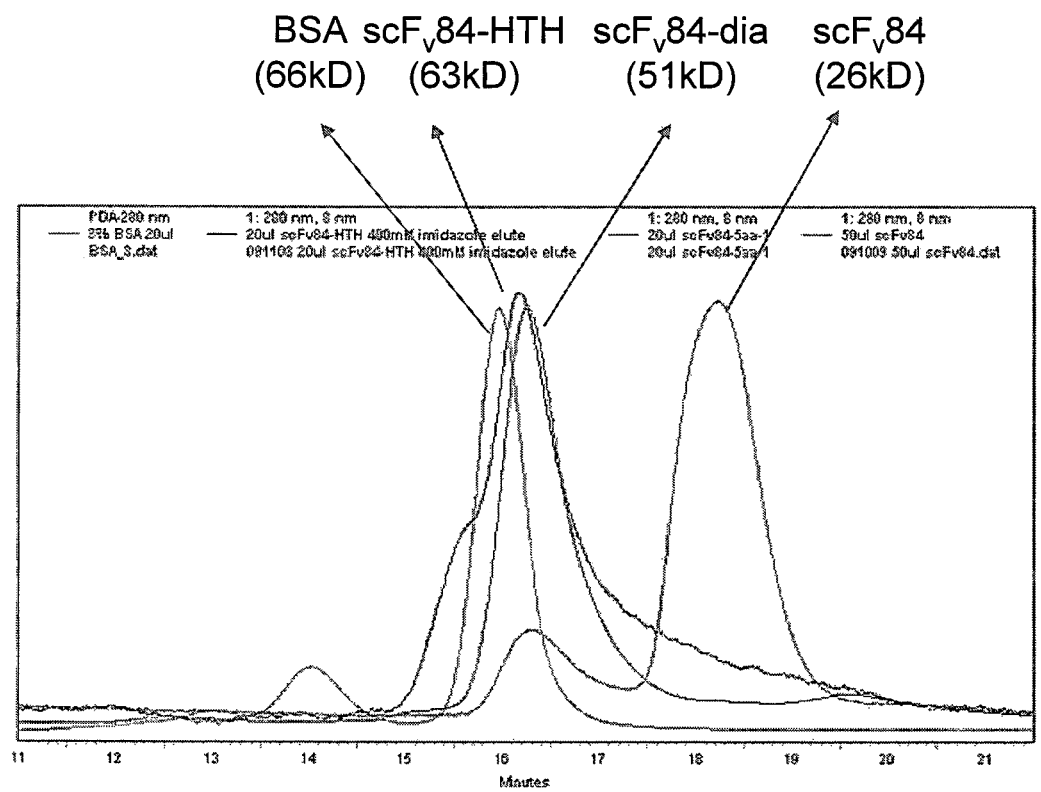
FIG. 5. shows an analysis of dimerization of scFv84-5aa diabody and scFv84-HTH by size-exclusion chromatography. Molecular weight of standards used are BSA (66 kDa) and scFv84 (26 kDa). scFv84-HTH is shown to be approximately the same size as BSA.

FIG. 4a illustrates the purity of the various antibody fragments expressed and purified by IMAC. Since the gel was run under denaturing conditions, the dimeric forms for scFv84-5aa diabody and scFv84-HTH were not obvious. FIG. 4b is the corresponding Western blot of the purified fragments and faint bands corresponding to the dimeric forms for the diabody (51 kD) and scFv84-HTH (63 kD) was visible. The dimeric nature of these two antibody molecules was confirmed by size-exclusion chromatography (FIG. 5).

Figure 6:
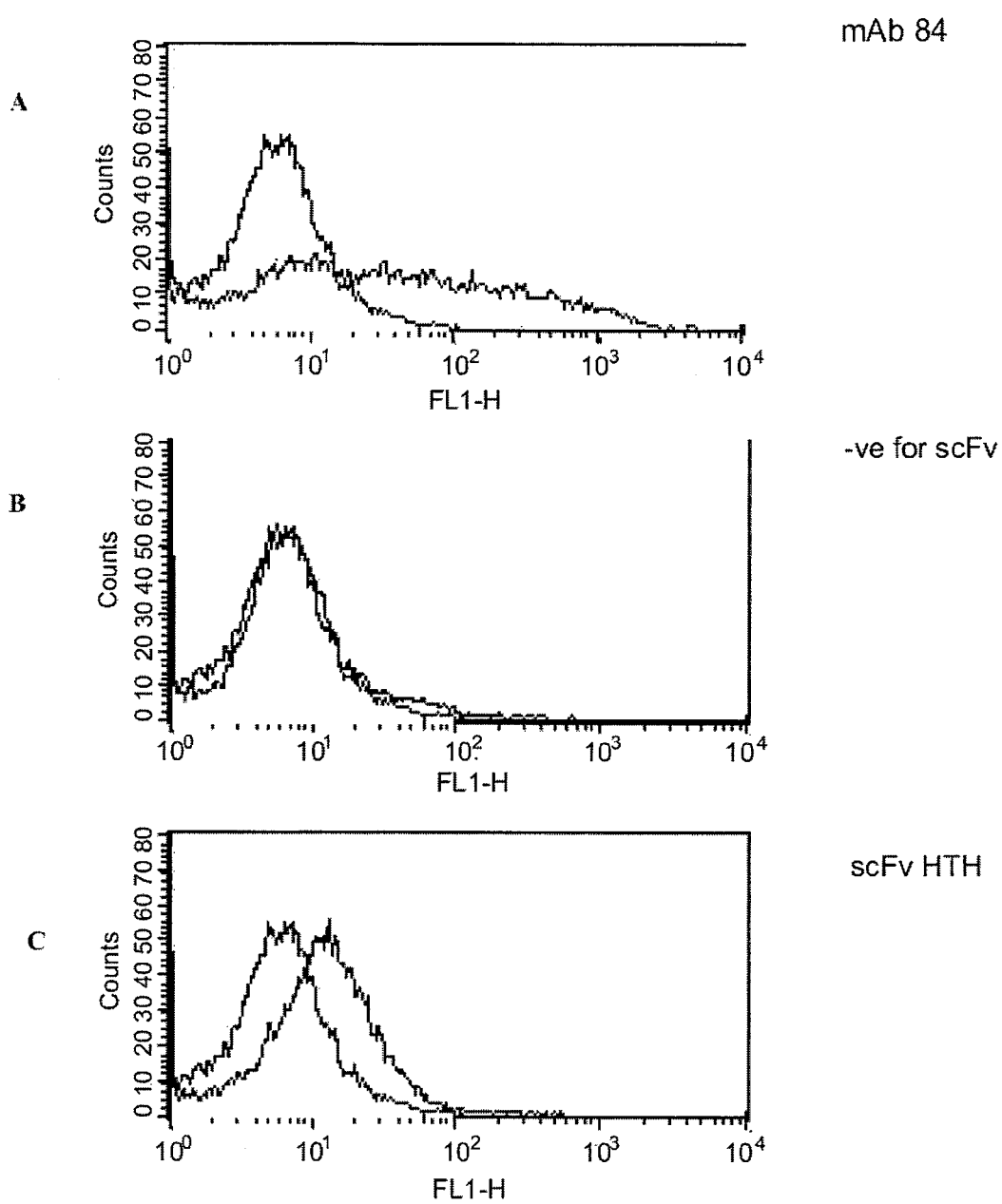
FIG. 6. shows binding of mAb84 and scFv84-HTH to undifferentiated hESC using flow cytometry. Black line shows negative control (no antibody treatment) while grey line shows cells after antibody treatment. (A) Incubated with 5 μg mAb84 and detected with anti-Ig-FITC. (B) Incubated with mouse anti-His and detected with anti-mouse Ig-FITC. (C) Incubated with 44.8 μg scFv84-HTH, followed by mouse anti-His and detected with anti-mouse Ig-FITC. Horizontal axis shows relative fluorescence. Vertical axis shows number of events (counts).

FIG. 6 shows by flow cytometry that both mAb84 and scFv84-HTH bind to undifferentiated hESCs.

Figure 7A:
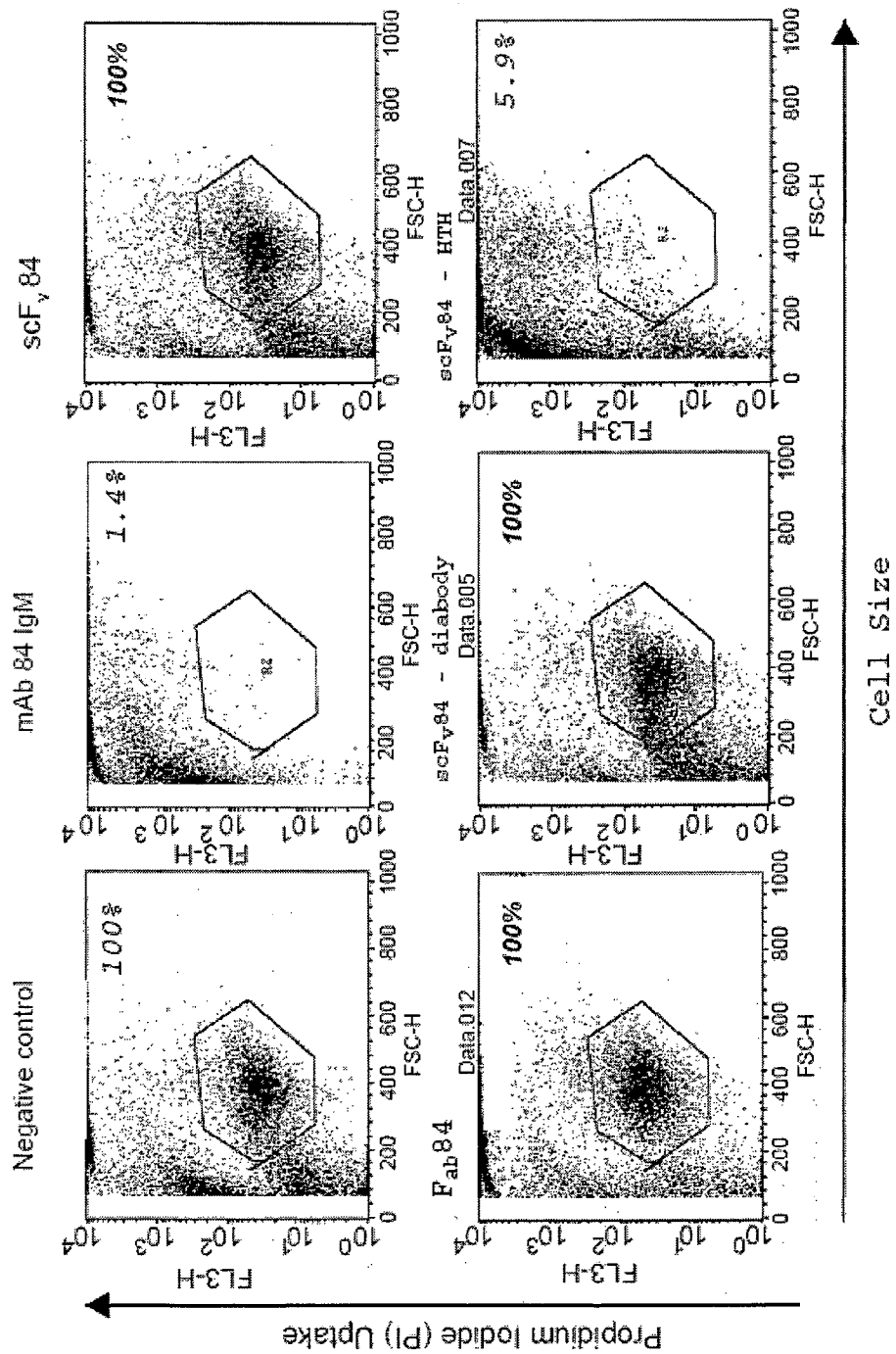
FIG. 7a. shows FACS results comparing cytotoxicity of mAb84 and fragments to hESC. Cells were incubated with 5 μg of mAb84 or 100 μg of antibody fragment before analysis by propidium iodide (PI) exclusion. Gated region represents viable cell population.
Figure 7A:
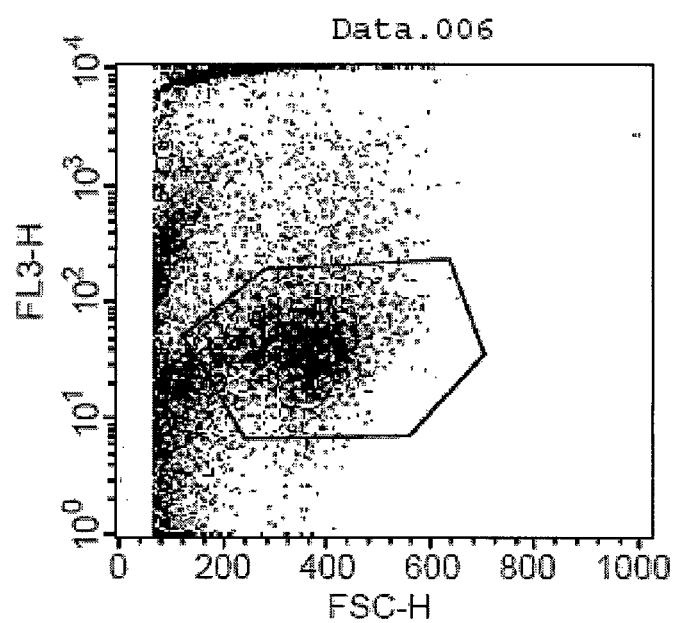
Figure 7B:
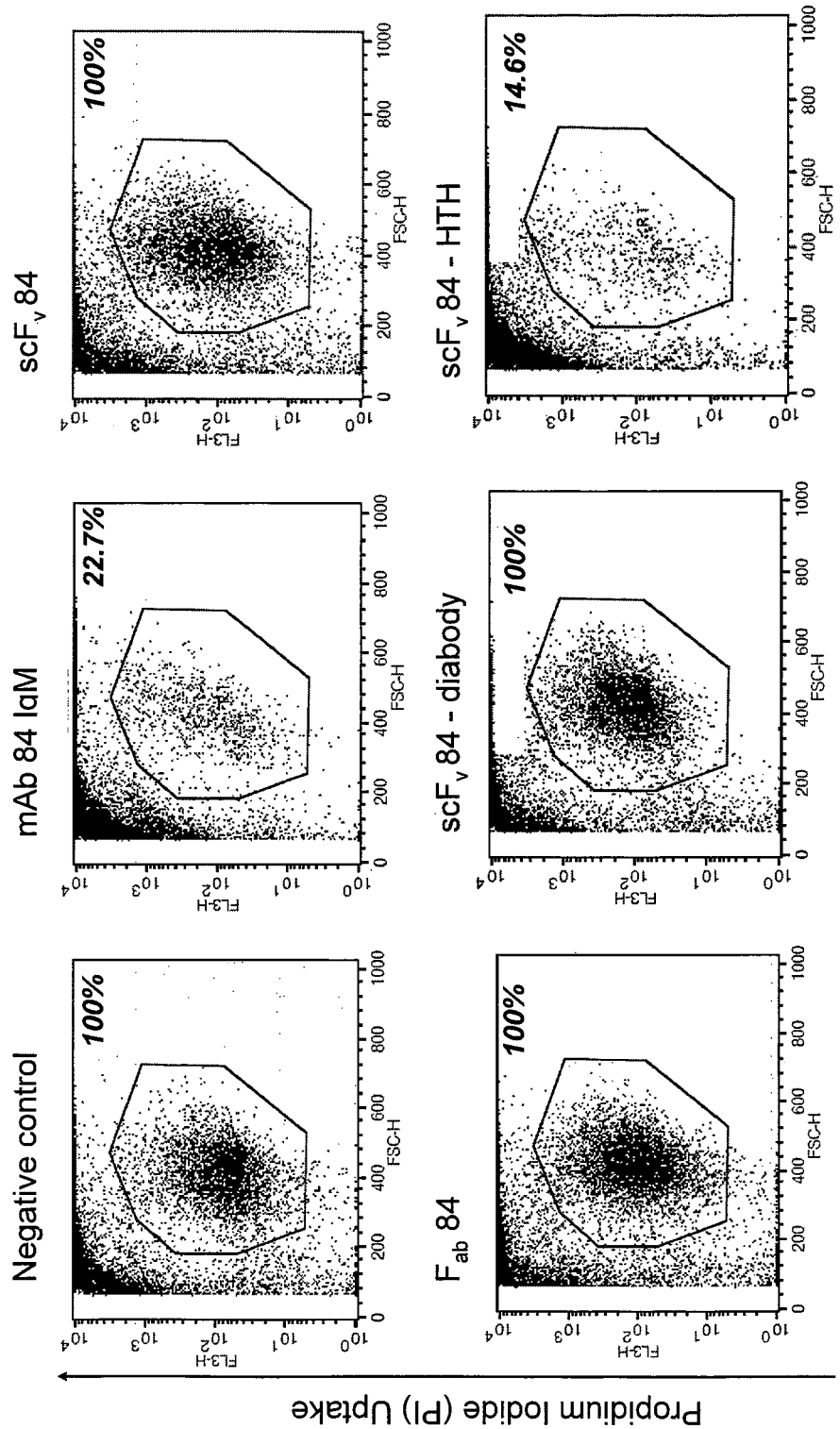
FIG. 7b. shows a repeat of FACS results comparing cytotoxicity of mAb84 and fragments to hECS. Cells were incubated with 5 μg of mAb 84 or 100 μg of antibody fragment before analysis by propidium iodide (PI) exclusion. Gated region represents viable cell population.

Of the antibody fragments tested, scFv84-HTH exhibited cytotoxic properties like that of mAb84. FIG. 7a and b shows the relative cytotoxic killing of the antibody fragments compared to mAb 84. The experiments were conducted on separate occasions, using different batches of hESC and antibody fragments. In each case, 100 µg of the antibody fragment and 5 µg of mAb 84 was used.

Figure 7C:
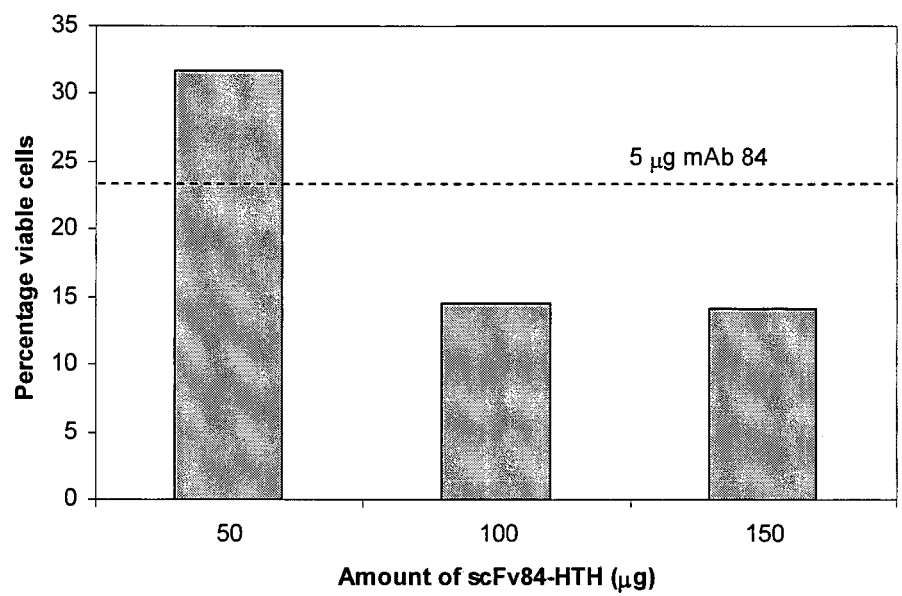
FIG. 7c. shows dose-dependent cytotoxicity to hESC of scFv84-HTH.

FIG. 7c shows the dose-dependent killing of hESC with increasing amounts of scFv84-HTH.

Figure 8:
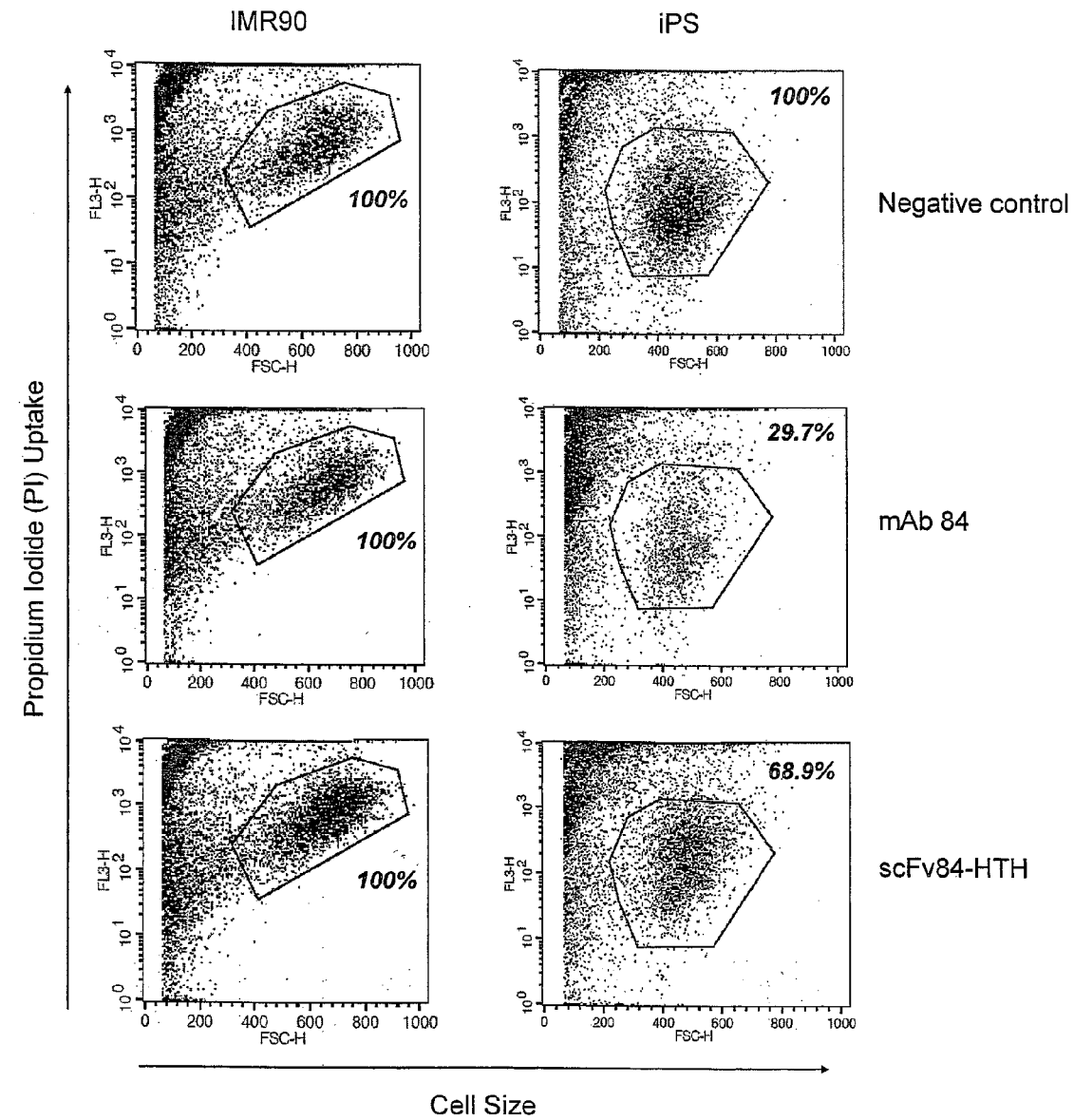
FIG. 8. shows FACS results showing specific cytotoxicity of mAb 84 and scFv84-HTH to induced pluripotent stem cells but not IMR90 fibroblasts. Cells were incubated with 5 of mAb84 or 100 μg of scFv84-HTH.

FIG. 8 shows that scFv84-HTH, like mAb 84, was also cytotoxic to iPS but not IMR90 fibroblasts.

Example 2

Figure 16:
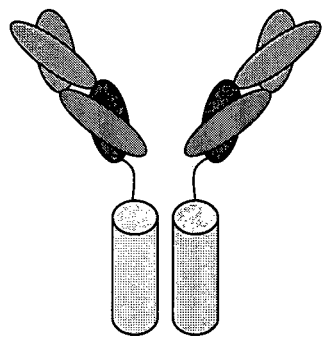
FIG. 16. is a schematic illustration of the Fab84-LZ.

We further engineered and evaluated an additional construct, Fab84-LZ, which comprises the Fab84 fragment extended at the C-terminus with the upper hinge region of IgG3 and the dimerizing motif taken from the GCN4 leucine zipper (FIGS. 15 and 16). We show that the new bivalent antibody fragment is also cytotoxic like scFv84-HTH. Hence, cytotoxicity is not limited solely to binding by scFv84 or the HTH (helix-turn-helix) motif.

Materials and Methods

Figure 17:
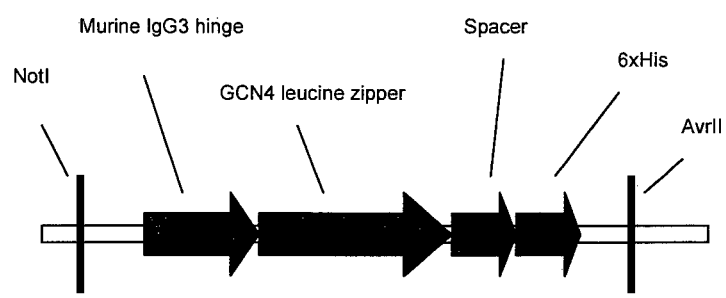
FIG. 17. is a representation of the primary structure of a gene sequence of the Leucine zipper motif.
Figure 18:
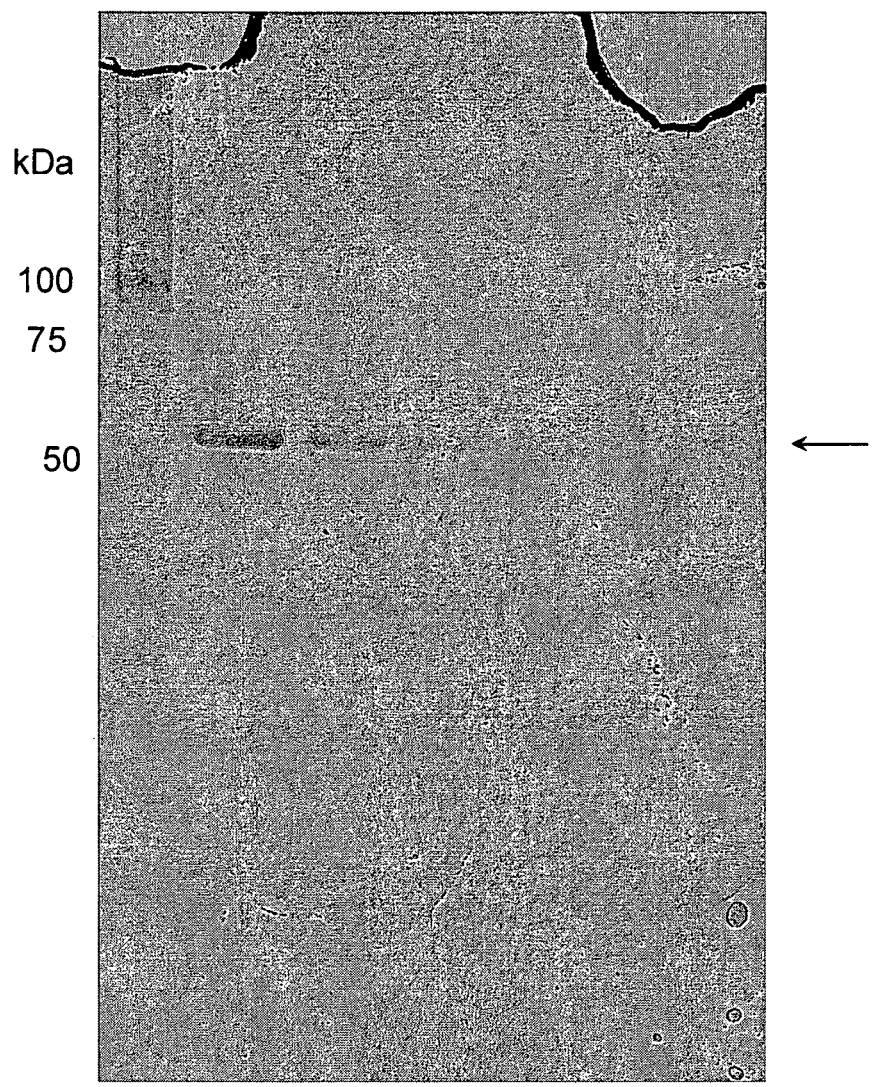
FIG. 18. shows the SDS-PAGE of Fab84-LZ IMAC eluted fractions following IMAC purification. Since this is a denaturing gel, the band at 52 kDa corresponds to the expected molecular weight of the monomer for Fab84-LZ.
Figure 19:
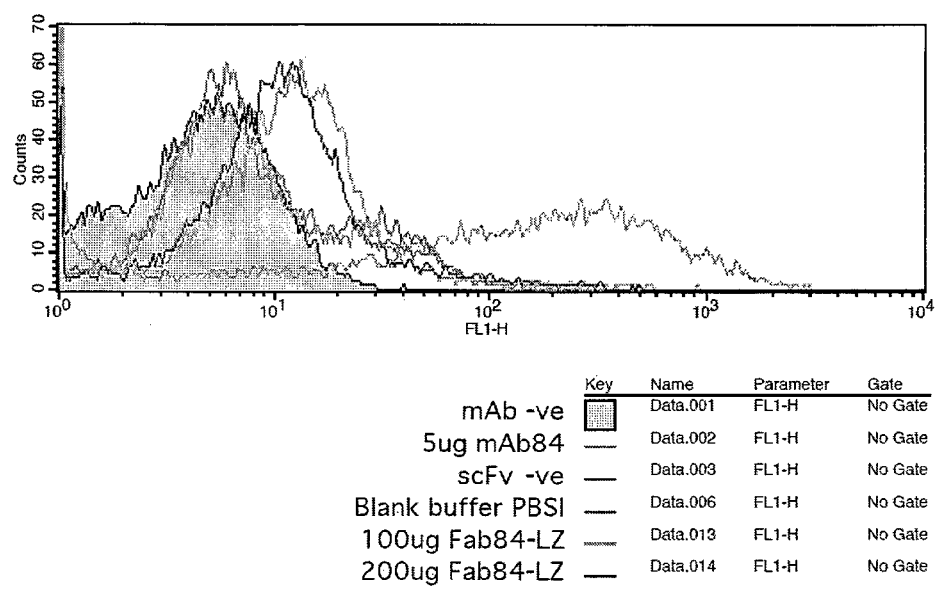
FIG. 19. FACS result showing binding of Fab84-LZ fragments to undifferentiated hESC (HES3 line).
Figure 20:
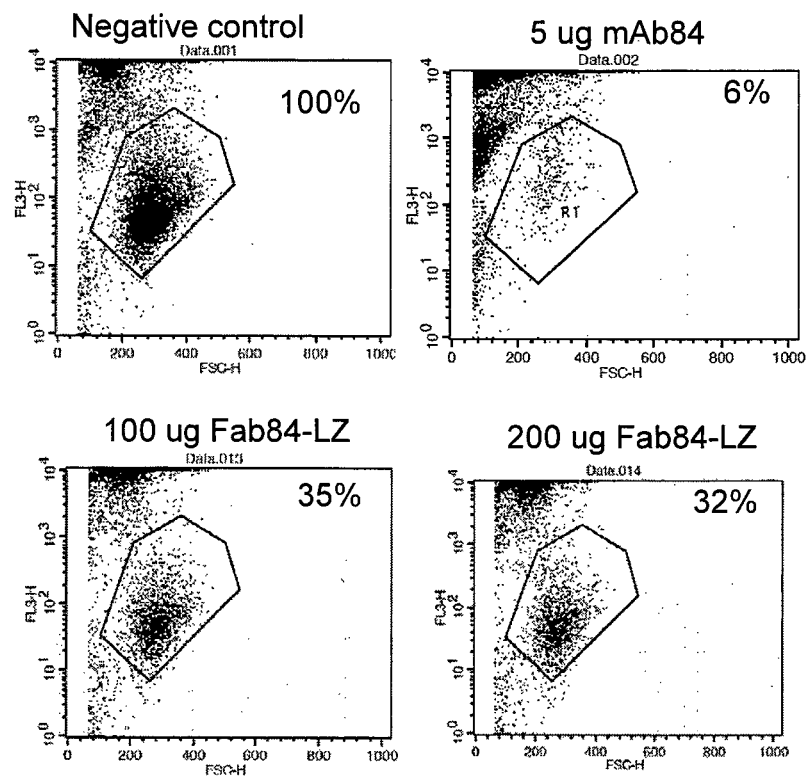
FIG. 20. FACS result showing cytotoxicity of Fab84-LZ fragments to undifferentiated hESC (HES3 line).

Vector Construction pMC-Fab84-LZ: The leucine-zipper motif consisting of a murine IgG3 hinge, helix, turn, helix, spacer and 6× his tag, was obtained in a pUC57 vector from Genscript (Genscript Inc. NJ, USA) (FIG. 17). The sequence was based on a dimerization motif described by Pluckthun (30). This plasmid was digested with NotI and AvrII, and ligated into pMC-Fab84 which was similarly digested. The vector pMC-Fab84 has NotI and AvrII sites at the end of the constant heavy chain, and the leucine-zipper motif was introduced into the C-terminus of the resulting protein. The resulting vector was named pMC-Fab84-LZ and its sequence verified by Big Dye sequencing.

The vector was then transformed into *Escherichia coli* BL21-Star(DE3) (Invitrogen) for protein expression.

Culture Fermentation Conditions

The fermentation conditions were similar to that described for scFv84-HTH with some minor modifications. Briefly, cells from glycerol stocks were streaked out on LB+Kan (30 µg/ml) plates and a single colony picked for inoculation of 50 ml of overnight culture incubated at 25° C., 280 rpm. Fermentation culture was started with 10% inoculum of overnight culture into 2×YT+Kan (30 µg/ml) media in baffled 2 L glass culture flask, and grown at 37° C., 150 rpm until OD600 reaches 1.5 to 2. Cultures were induced with 50 µM IPTG at 30° C. and harvested at 5 hours post induction.

Osmotic Shock

The osmotic shock protocol was slightly modified from that used for scFv84-HTH. Cells were harvested by pelleting at 10,000×g (Hitachi Ultracentrifuge) for 30 min and media supernatant collected. The media supernatant fraction was filtered using a 0.2 µm filter (Nalgene) before storing at 4° C. to prevent microbial growth.

The pellet was then resuspended in ice-cold osmotic shock buffer (1 mM EDTA, 200 mMTris-HCl, 20% Sucrose, pH8.0) and then incubated on ice for 1 hour with gentle stirring. The mixture was spun at 35,000×g for 40 min at 4° C. and the supernatant was collected.

Buffer Exchange

The osmotic shock fraction was buffer exchanged into IMAC equilibration buffer (50 mM Sodium phosphate, 300 mM NaCl, pH 7.0) using a Vivacell concentrator (5 kDa MWCO).

Immobilized Metal Affinity Chromatography

The buffer-exchanged fractions were then purified using immobilized metal affinity chromatography (IMAC) with Talon® Polyhistidine-Tag Purification Resin (Clontech). Cobalt was the capturing metal ion. The column was equilibrated with Equilibrating/Washing Buffer (50 mM Sodium Phosphate, 300 mM NaCl, pH 7.0). The sample was applied to a 1 ml bed resin at a rate of ~1-2 ml/min. After washing for at least 3 times with Equilibrating/Washing Buffer, the sample was eluted with 10 columns volumes of Elution Buffer (50 mM Sodium Phosphate, 300 mM NaCl, 150 mM Imidazole, pH 7.0). The column was washed, stripped and regenerated as per the manufacturer's instructions. The eluted fractions were then analyzed by SDS-PAGE and Coomassie Brilliant Blue staining of the gel.

Prior to FACS analysis, the purified protein was buffer exchanged into PBSI (phosphate buffered saline with 50 mM imidazole, pH7.0) using PD-10 columns (GE Healthcare)

SDS-PAGE

Proteins were separated using 4-12% Bis-Tris gels (NuPAGE® Novex Bis Tris gels, NuPAGE® System, Invitrogen) and were visualized with Coomassie Brilliant Blue (Thermo Scientific Pierce Protein Research Products).

FACS

Human ES cells were used to test binding and cytotoxicity of antibody fragments. In each assay, 100 µg of protein was incubated with equal amounts of cells. Cells were harvested as single cell suspensions using trypsin, resuspended in 1% BSA/PBS and incubated for 30 min on ice for each antibody fragment. Binding of antibody fragments to cells was monitored using flow cytometry following incubation with mouse anti-His antibody (Qiagen) and anti-Ig-FITC. Cytotoxicity towards cells was tested by PI exclusion assay and flow cytometry.

REFERENCES

1. Choo et al (2008). Selection Against Undifferentiated Human Embryonic Stem Cells By A Cytotoxic Antibody Recognizing Podocalyxin-like Protein-1. Stem Cells 26(6):1454-63.
2. Takahashi et al (2007) Induction of Pluripotent Stem Cells from Adult Human Fibroblasts by Defined Factors. Cell 131(5):861-72.
3. Yu et al (2007) Induced Pluripotent Stem Cell Lines Derived from Human Somatic Cells. Science 318(5858): 1917-20.
4. Choo et at (2004) Expansion of pluripotent human embryonic stem cells on human feeders. Biotechnology and Bioengineering 88:321-331.
5. Brandenberger et al (2004) Transcriptome characterization elucidates signaling networks that control human ES cell growth an differentiation. Nature Biotechnology 22:707-716
6. Cai et al (2006) Assessing self-renewal and differentiation in human embryonic stem cell limes. Stem cells 24:516-530
7. Cai et al (2005) Development of antibodies to human embryonic stem cell antigens. BMC Dev Biol 5:26
8. Wei et al (2005) Transcriptome profiling of human and murine ESCs identifies divergent paths required to maintain the stem cell state. Stem Cells 23:166-185
9. Schopperle et al. (2007) The TRA-1-60 and TRA-1-81 human pluripotent stem cell markers are expressed on podocalyxin in embryonal carcinoma. Stem cells 25:723-730.
10. Yamanaka et al (2009) A Fresh Look at iPS Cells. Cell 137: 13-17
11. Okita et al (2007) Generation of germline-competent induced pluripotent stem cells. Nature 448:313-318.
12. Chung Y, Klimanskaya I, Becker S, et al. Embryonic and extraembryonic stem cell lines derived from single mouse blastomeres. Nature. 2006; 439:216-219.
13. Chung Y, Klimanskaya I, Becker S, et al. Human embryonic stem cell lines generated without embryo destruction. Cell Stem Cell. 2008; 2:113-117.

14. Jiang, Y., Jahagirdar, B. N., Reinhardt, R. L., Schwartz, R. E., Keene, C. D., Ortiz Gonzalez, X. R., Reyes, M., Lenvik, T., Lund, T., Blackstad, M., et al. (2002). Pluripotency of mesenchymal stem cells derived from adult marrow. Nature 418, 41-49.
15. Kaji et al. Virus-free induction of pluripotency and subsequent excision of reprogramming factors. Nature. Online publication 1 Mar. 2009.
16. Kanatsu-Shinohara, M., Inoue, K., Lee, J., Yoshimoto, M., Ogonuki, N., Miki, H., Baba, S., Kato, T., Kazuki, Y., Toyokuni, S., et al. (2004). Generation of pluripotent stem cells from neonatal mouse testis. Cell 119, 1001-1012.
17. Kershaw et al (1997) J. Biol. Chem. 272, 15708-15714.
18. Kim et al. Ex vivo characteristics of human amniotic membrane-derived stem cells. Cloning Stem Cells 2007 Winter; 9(4):581-94.
19. Lin et al. Multilineage potential of homozygous stem cells derived from metaphase II oocytes. Stem Cells. 2003; 21(2):152-61.
20. Lei et al Xeno-free derivation and culture of human embryonic stem cells: current status, problems and challenges. Cell Research (2007) 17:682-688.
21. Maherali N, et. al. Directly reprogrammed fibroblasts show global epigenetic remodeling and widespread tissue contribution. Cell Stem Cell 2007; 1:55-70.
22. Matsui, Y., Zsebo, K., and Hogan, B. L. (1992). Derivation of pluripotential embryonic stem cells from murine primordial germ cells in culture. Cell 70, 841-847.
23. Takahashi K, Tanabe K, Ohnuki M, Narita M, Ichisaka T, Tomoda K, Yamanaka S. (2007). Induction of pluripotent stem cells from adult human fibroblasts by defined factors. Cell. 131(5):861-72.
24. Takahashi, K. & Yamanaka, S. Induction of pluripotent stem cells from mouse embryonic and adult fibroblast cultures by defined factors. Cell 2006; 126:663-676.
25. Wernig M, et: al. In vitro reprogramming of fibroblasts into a pluripotent ES-cell-like state. Nature 2007; 448:318-24.
26. Yamanaka S, et. al. Generation of germline-competent induced pluripotent stem cells. Nature 2007; 448:313-7.
27. Yu J, Vodyanik M A, Smuga-Otto K, Antosiewicz-Bourget J, Frane J L, Tian S, Nie J, Jonsdottir G A, Ruotti V, Stewart R, Slukvin I I, Thomson J A. Induced pluripotent stem cell lines derived from human somatic cells. Science. 318(5858):1917-20. Epub 2007 November 20.
28. Zhang X, Stojkovic P, Przyborski S, et al. Derivation of human embryonic stem cells from developing and arrested embryos. Stem Cells 2006; 24:2669-2676.
29. H. L. Tan et al. (2009) mAb 84, a cytotoxic antibody that kills undifferentiated human embryonic stem cells via oncosis. Stem Cells 27 (8):1792-1801.
30. A. Pluckthun & P. Pack. (1997) New protein engineering approaches to multivalent and bispecific antibody fragments. Immunotechnology. 3 (2):83-105.

In accordance with 37 CFR 1.52(e)(5), a Sequence Listing in the form of a text file (entitled "Seq_Listing_2008187_0038_ST25.txt," created on Aug. 3, 2012, and 25 kilobyte) is incorporated herein by reference in its entirety.

The invention claimed is:

1. An antibody molecule which binds PODXL and includes two monomers, each monomer including an Fv antibody fragment connected via a flexible linker to a dimerizing portion comprising a dimerization domain, wherein the dimerizing portions interact to form the antibody molecule, and wherein the antibody molecule is a multimer,
wherein each Fv antibody fragment has a VH region and a VL region,
and comprises CDR amino acid sequences (i) to (vi):

(i) VL CDR1:
(SEQ ID NO: 2)
SASSSVNYMY;

(ii) VL CDR2:
(SEQ ID NO: 3)
DTSNLAS;

(iii) VL CDR3:
(SEQ ID NO: 4)
QQWSSYPYT;

(iv) VH CDR1:
(SEQ ID NO: 5)
NYWMN;

(v) VH CDR2:
(SEQ ID NO: 6)
EIRLKSNNYATHYAESVKG;

(vi) VH CDR3:
(SEQ ID NO: 7)
ERA;

wherein the dimerization domain is selected from a helix-turn-helix (HTH) motif, a coiled-coil motif, or an EF hand motif; and wherein the antibody molecule is a cytotoxic antibody molecule.

2. The antibody molecule of claim 1 wherein the Fv antibody fragment is an scFv antibody fragment.

3. The antibody molecule of claim 1 which is a dimer.

4. The antibody molecule of claim 1 wherein the flexible linker is a linker peptide which has 4 or more amino acids, 5 or more amino acids, 6 or more amino acids, 7 or more amino acids, 8 or more amino acids, 9 or more amino acids, 10 or more amino acids, 11 or more amino acids, 12 or more amino acids, 13 or more amino acids, 14 or more amino acids, or 15 or more amino acids.

5. The antibody molecule of claim 1 wherein the flexible linker is a linker peptide which has 30 or fewer amino acids, 25 or fewer amino acids, 20 or fewer amino acids, or 15 or fewer amino acids.

6. The antibody molecule of claim 1 wherein the flexible linker is a linker peptide which comprises the amino acid sequence of an immunoglobulin hinge region.

7. The antibody molecule of claim 6 wherein the linker peptide comprises an IgG hinge region.

8. The antibody molecule of claim 7 wherein the linker peptide has a sequence substantially as set out in SEQ ID NO: 10.

9. The antibody molecule of claim 1 wherein the dimerization domain comprises a helix-turn-helix motif.

10. The antibody molecule of claim 1 wherein the dimerizing portions interact through non-covalent interactions.

11. The antibody molecule of claim 1 wherein the dimerizing portions interact through covalent interactions.

12. The antibody molecule of claim 1 which is less than 150 kDa.

13. The antibody molecule of claim 12 which is about 65 kDa or less.

14. The antibody molecule of claim 1 which is 150 kDa or less, 140 kDa or less, 130 kDa or less, 120 kDa or less, 110 kDa or less, 100 kDa or less, 90 kDa or less, 80 kDa or less, 70 kDa or less, 60 kDa or less, or 50 kDa or less.

15. The antibody molecule of claim 1 which is capable of destroying an undifferentiated pluripotent stem cell.

16. The antibody molecule of claim 1 which is cytotoxic to an undifferentiated pluripotent stem cell.

17. The antibody molecule of claim 1 wherein the dimerization domain is a leucine zipper motif.

18. The antibody molecule of claim 1 which is a tetramer.

* * * * *